(12) United States Patent
Hasan et al.

(10) Patent No.: US 7,498,029 B2
(45) Date of Patent: Mar. 3, 2009

(54) PHOTOIMMUNOTHERAPIES FOR CANCER USING COMBINATION THERAPIES

(75) Inventors: Tayyaba Hasan, Boston, MA (US); Mark D. Savellano, Charlestown, MA (US); Mihaela Skobe, New York, NY (US)

(73) Assignee: The General Hospital Corporation, Boston, MA (US)

( * ) Notice: Subject to any disclaimer, the term of this patent is extended or adjusted under 35 U.S.C. 154(b) by 461 days.

(21) Appl. No.: 10/137,029

(22) Filed: May 1, 2002

(65) Prior Publication Data

US 2002/0197262 A1 Dec. 26, 2002

Related U.S. Application Data

(60) Provisional application No. 60/287,767, filed on May 1, 2001, provisional application No. 60/338,961, filed on Dec. 7, 2001.

(51) Int. Cl.
- *A61K 39/395* (2006.01)
- *A61N 5/06* (2006.01)
- *A61K 39/00* (2006.01)

(52) U.S. Cl. .................. 424/143.1; 424/155.1; 607/88; 607/89

(58) Field of Classification Search .................. None
See application file for complete search history.

(56) References Cited

U.S. PATENT DOCUMENTS

| | | | |
|---|---|---|---|
| 4,867,973 A | 9/1989 | Goers et al. | |
| 4,883,790 A | 11/1989 | Levy et al. | |
| 5,484,803 A | 1/1996 | Richter | |
| 5,736,563 A | 4/1998 | Richter | |
| 5,776,966 A | 7/1998 | North | |
| 5,789,433 A | 8/1998 | Chan et al. | |
| 5,798,349 A | 8/1998 | Levy et al. | |
| 5,807,881 A | 9/1998 | Leong et al. | |
| 5,861,499 A | 1/1999 | Rockwell et al. | |
| 5,868,695 A | 2/1999 | Wolf, Jr. et al. | |
| 5,955,311 A | 9/1999 | Rockwell et al. | |
| 6,015,897 A | 1/2000 | Theodore et al. | |
| 6,030,955 A | 2/2000 | Stein et al. | |
| 6,048,736 A | 4/2000 | Kosak | |
| 6,123,923 A | 9/2000 | Unger et al. | |
| 6,217,869 B1 | 4/2001 | Meyer et al. | |
| 6,344,050 B1 | 2/2002 | Chen | |
| 6,602,274 B1 * | 8/2003 | Chen ........................... | 607/88 |
| 6,899,723 B2 * | 5/2005 | Chen ........................... | 607/88 |
| 7,125,542 B2 * | 10/2006 | Miller et al. ............... | 424/9.61 |
| 2002/0026945 A1 * | 3/2002 | Gomer et al. ............... | 128/898 |

FOREIGN PATENT DOCUMENTS

| | | |
|---|---|---|
| WO | WO 95/21868 A1 | 8/1995 |
| WO | WO 00/36983 | 6/2000 |
| WO | WO 00/36983 A1 | 6/2000 |
| WO | WO 00/69459 A1 | 11/2000 |
| WO | WO 01/97814 A1 | 12/2001 |
| WO | WO03/070234 * | 8/2003 |

OTHER PUBLICATIONS

Clark (Protein Engineering of Antibody Molecules for Prophylactic and Therapeutic Applications in Man, 1993.*
Abstract of Moor et al (Photochemistry and Photobiology, Jun. 1999, vol. 69, p. 9S).*
Rihova (Advanced Drug Delivery Reviews, 1998, vol. 29, pp. 273-289).*
Streitwieser and Heathcock, 'Introduction to Organic Chemistry', 1976, p. 624.*
Moroni et al, Lancet Oncology, 2005, vol. 6, pp. 279-286.*
Dimitroff et al (Investigational New Drugs, 1999, vol. 17, pp. 121-135).*
Bruns et al (Clinical Cancer Research, May 2000, vol. 6, pp. 1936-1948).*
Yang et al (Critical Reviews in Oncology and Hematology, Apr. 2001, vol. 38, pp. 17-23).*
F. Jiang et al., "Enhanced Photodynamic Killing of Target Cells by Either Monoclonal Antibody or Low Density Lipoprotein Mediated Delivery Systems", Journal of Controlled Release, vol. 19, pp. 41-58, 1992.
M. R. Hamblin et al., "Biodistribution of Charged 17.1A Photoimmunoconjugates in a murine model of hepatic metastasis of Colorectal Cancer", British Journal of Cancer, vol. 83, No. 11, pp. 1544-1551, 2000.
Andreopoulos et al. Photoimmobilization of organophosphorous hydrolase within a PEG-based hydrogel. Biotechnol Bioeng. Dec. 5, 1999; 65(5): 579-88.
Brumeanu et al. Purification of antigenized immunoglobulins derivatized with monomethoxypolyethylene glycol. J. Chromatogr A. Apr. 14, 1995; 696(2): 219-25.
Goff et al. "Photoimmunotherapy of Human Ovarian Cells ex Vivo" Cancer Research (1991) 51: 4762-4767.
Heitner et al. "Selection of cell binding and internalizing epidermal growth factor receptor antibodies from a phage display library" Journal of Immunological Methods (2001) 248: 17-30.
Hornung R. et al. "PEG-m-THPC-mediated photodynamic effects on normal rat tissues" Photochem Photobiol Nov. 2000, 72(5): 696-700.

(Continued)

*Primary Examiner*—Karen A Canella
(74) *Attorney, Agent, or Firm*—Edwards Angell Palmer & Dodge LLP; Peter C. Lauro, Esq.

(57) ABSTRACT

The present invention relates to photosensitizer immunoconjugate compositions and combination therapies for use in cancer related photodynamic treatments and diagnostic methods. Photosensitizer immunoconjugates comprising a photosensitizer conjugated to a tumor-specific and/or tumoricidal antibody and processes for the preparation thereof are described. The use of photosensitizer immunoconjugates (PICs) offers improved photosensitizer delivery specificity for diagnostic and therapeutic applications. Combination therapies to co-localize activated photosensitizer compounds and tumoricidal antibodies in tumor tissues are also described.

14 Claims, 25 Drawing Sheets

OTHER PUBLICATIONS

Hornung et al. Minimally-invasive debulking of ovarian cancer in the rat pelvis by means of photodynamic therapy us pegylated photosensitizer PEG-m-THPC. (1999) Br J. Cancer Oct; 81(4): 631-7.

Hamblin et al. "Pegylated poly-L-lysine chlorin-e6 conjugates as photosensitizers" (1997) Photochemistry and Photobiology 65(Spec. Issue): p8S 1997.

Jiang et al. "Development of Technology for linking photosensitizers to a model monoclonal antibody" Journal of Immunological Methods (1990) 134: 139-149.

Rovers et al. "Biodistribution and bioactivity of tetra-pegylated meta-tetra(hydroxypenyl) chlorin compared to tetra(hydroxyphenyl) chlorin in a rat liver tumor model." Photocehm Phobiol. Feb. 2000; 71(2): 211-7.

Ris et al. Photodynamic therapy with mTHPC and polyethylene glycol-derived mTHPC: a comparative study on tumour xenografts. Br J. Cancer Mar. 1999; 79(7-8):1061-6.

Ris et al. "Endobronchial photodynamic therapy: a comparison of mTHPC and polyethylene glycol-derived mTHP human tumor xenografts and tumor-free bronchi of minipigs." Lasers Surg Med. (1998) 23(1): 25-32.

Savellano et al. "Pegylated BPD verteporfin C225 anti-EGF receptor direct covalent linkage photsensitizer immunoconjugates"(1999) Photochemistry and Photobiology 69(Spec Issue): p385 June.

Tsutsumi et al. "Site-specific chemical modification with polyethylene glycol of recombinant immunotoxin anti-Tac (Fv LMB-2) improves antitumor activity and reduces animal toxicity and immunogenicity." Proc. Natl. Acad Sci USA Jul. 18, 2000; 97(15): 8548-53.

Torchilin VP., "Immunoliposomes and PEGylated immunoliposomes: possible use for targeted delivery of imaging age" Immunomethods. Jun. 1994 4(3): 244-258. Review.

Wu D, Pardridge WM. Neuroprotein with noninvasice neurotrophin delivery to the brain. Proc Natl. Acad Sci USA Jan. 5, 1999; 96(1): 254-9.

Molpus et al. "Intraperitoneal photoimmunotherapy of Ovarian Carcinoma Xenografts in Nude Mice using Charged Photoimmunoconjugates" Gynecologic Oncology (2000) 76:397-404.

Hasan et al. "Photodynamic Therapy of Cancer" Principles of Radiation Oncology, Chapter 36, Section 11, 489-502.

Del Governatore et al. "Targeted photodestruction of human colon cancer cells using charged 17.1A chlorin$_{e6}$ immunoconjugates" British Journal of Cancer (2000) 82(1), 56-64.

Hornung R., et al. Highly selective targeting of ovarian cancer with the photosensitizer PEG-m-THPC in a rat model., Photochem Photobiol Oct. 1999; 70(4): 624-9.

Tsutsumi Y et al. "Site-specific chemical modification with polyethylene glycol of recombinant immunotoxin anti-Tac(Fv)-PE38 (LMB-2) improved antitumor activity and reduces animal toxicity and immunogenicity." Proc Natl Acad Sci USA Jul. 18, 2000; 97(15): 8548-53.

Ris HB et al. "Experimental assessment of photodynamic therapy with chlorins for malignant mesothelioma." Eur J. Cardiothorac Surg Oct. 1997; 12(4): 542-8.

Savellano et al. "Pegylated BPD verteporfin C225 anti-EGF receptor direct covalent linkage photsensitizer immunoconjugates" (1999), 27th Annual Meeting of the American Society for Photobiology, Jul. 10-15, 1999.

\* cited by examiner

Figure 1A

| Anti-Cancer Mab/Fab | Growth Inhibition | Epitope Recognition | Tumor Cell Associations |
|---|---|---|---|
| • Edrecolomab (CO17-1A antibody) (Adkins 1998) | • Yes | GA733 antigen, Also known as CO17-1A, EGP, KS1-4, KSA, and Ep-CAM. | Colorectal cancer |
| • IMC-C225 (Modjtahedi 1994) <br><br> • (EMD 72000) (Bier 1998) | • Yes <br><br> • Yes | EGFR receptor | Multiple tumor cell associations, such as cancer of the brain, bladder, prostate, lung, pancreas, breast, head and neck, and ovaries |
| • Anti-human CEA (Abeyounis 1989) <br><br> • 21B2 antibody (Maruyama 2000) | • No <br><br> • No | Carcinoembryonic Antigen (CEA) | CEA-positive human adenocarcinoma cells and human gastric cancers |
| • CC49 (Goel A 2000) | • No | Tumor-associated glycoprotein, (TAG-72) | Colon, colorectal and prostate cancers. |
| • Anti-ganglioside G(D2) antibody Ch14.18 (Ozkaynak M.F. 2000) | • Yes | Ganglioside G(D2) | Neuroblastomas |
| • BIWA 1 (Anti-CD44v6) (Stroomer J.W. 2000) | • No | CD44 variant 6 | Squamous cell carcinoma, head and neck cancers |
| • 2A11 (Johnson B.E. 1995) | • Yes | Gastrin releasing peptide, bombesin, and bombesin-like peptides | Small cell lung carcinomas |

Figure 1B

| Anti-Cancer Mab/Fab | Growth Inhibition | Epitope Recognition | Tumor Cell Associations |
|---|---|---|---|
| • Antibody OC-125 (Eagle 1997)<br>• Monoclonal antibody OvaRex MAb B43.13 (Schultes 1999) | • No<br><br>• Yes | Ovarian cancer-associated antigen CA125 | Ovarian and cervical cancer |
| • Trastuzumab (Herceptin) (Kumar R. 2000) | • Yes | Growth factor receptor HER2 | Breast cancer |
| • Mib-1 (Comin 2000) | • No | Proliferation related antigen Ki-67. | Larynx, head and neck cancer |
| • MLS 102 (Fukui 1991) | • No | Recognizes cancer-associated mucin | Colon cancer |
| • Rituximab (Rituxan) (Grillo-Lopez 2000)<br>• Tositumomab (Bexxar) (Vose 2000) | • Yes<br><br>• No | CD20 | Non-Hodgkin's lymphomas. |
| • F6-734 (Kraeber-Bodere 1999) | • No | Bispecific for CEA/DTPA | Medullary thyroid carcinoma and small-cell lung cancer |
| • ch-Fab-A7 (Otsuji 1996) | • No | Unknown | Colon and pancreatic cancers |
| • 2C3 (Brekken 2000)<br>• rhuMAb VEGF (Gordon 2001) | • Yes<br><br>• Yes | Vascular endothelial growth factor (VEGF) | Tumor cell endothelium |
| • BR96 (Ajani J.A. 2000) | • No | LewisY antigen | Advanced gastric adenocarcinoma. |
| • CAMPATH 1H (Hainsworth 2000) | • Yes | CD52 | Lymphomas |

Figure 1C

| Anti-Cancer Mab/Fab | Growth Inhibition | Epitope Recognition | Tumor Cell Associations |
|---|---|---|---|
| • 2G7 (Arteaga 1993) | • Yes | TGFβ1 receptor | Breast cancer |
| • Anti-human VEGF3 (Flt4/MYYN):AB1875 (Chemicon) | • Yes | VEGF Receptor 3 VEGFR-3 (Flt4) | Lymphatic Vessels |
| • Anti-Flt-4AB3127 (Chemicon) | • Yes | VEGF Receptor 3 VEGFR-3 (Flt4) | Lymphatic Vessels |
| • Alpha IR-3 (Zia 1996) | • Yes | IGF-1 receptor | Non-small cell lung cancers |
| • ABX-EGF (Yang 2001) | • Yes | EGFα | Pancreatic, renal, breast and prostate cancers |
| • SR1 (Lauria 1995) | • Unknown | c-Kit receptor | Leukemias, including acute myelocytic leukemia (AML) |
| • Yb5.B8 (Lerner 1991) | • Unknown | | Same as above |
| • 17F.11 (Buhring 1991) | • Unknown | | Myeloid leukemias |
| • Anti -p75 and -p64 IL-2R (Zambello 1997) | • Yes | p75 and p64 IL-2 Receptor | Lymphomas. |
| • Flt-4 (C-20):sc-321 (Marconcini, 1999) (Fielder, 1997) | • Yes | VEGF Receptor 3 VEGFR-3 (Flt4) | Lymphatic Vessels |
| • Anti-human VEGFR3 (Flt4):AF349 (R&D) | • Yes | VEGF Receptor 3 VEGFR-3 (Flt4) | Lymphatic Vessels |
| • Biotinylated anti-human VEGFR3 (Flt4):BAF349 (R&D) | • Yes | VEGF Receptor 3 VEGFR-3 (Flt4) | Lymphatic Vessels |

Figure 1D

| Anti-Cancer Mab/Fab | Growth Inhibition | Epitope Recognition | Tumor Cell Associations |
|---|---|---|---|
| • Anti-mouse VEGFR3 (Flt4):AF743 (R&D) | • Yes | VEGF Receptor 3 VEGFR-3 (Flt4) | Lymphatic Vessels |
| • Biotinylated anti-mouse VEGFR3 (Flt4):BAF743 (R&D) | • Yes | VEGF Receptor 3 VEGFR-3 (Flt4) | Lymphatic Vessels |
| • Anti-mouse VEGFR3 (Flt4):MAB743 (R&D) | • Yes | VEGF Receptor 3 VEGFR-3 (Flt4) | Lymphatic Vessels |
| • Anti-Mouse FLT-4:FLT (Finnerty, 1993) (Aprelikova, 1992) | • Yes | VEGF Receptor 3 VEGFR-3 (Flt4) | Lymphatic Vessels |
| • Biotin anti-mouse VEGF receptor-3 (Flt-4):AFL4:13-5988 (Kubo, 2000) (Saaristo, 2000) (Paavonen, 2000; (Larrivee, 2000) | • Yes | VEGF Receptor 3 VEGFR3 (Flt4) | Lymphatic Vessels |
| • Functional Grade purified anti-mouse VEGF receptor-3 (Flt-4):ALF4:16-5988 (Kubo, 2000) (Saaristo, 2000) (Paavonen, 2000) (Larrivee, 2000) | • Yes | VEGF Receptor 3 VEGFR3 (Flt4) | Lymphatic Vessels |
| • Anti-Flt4 (VEGF-R3):343009 (Calbiochem) | • Yes | VEGF Receptor 3 VEGFR3 (Flt4) | Lymphatic Vessels |
| • Anti-phospho-VEGF receptor-2/3 (Ab-1):PC460 (Calbiochem) | • Yes | VEGF Receptor 3 VEGFR3 (Flt4) | Lymphatic Vessels |

Step 1:

Purify the BPDNHS ester by silica gel chromatography using ethyl acetate as the eluant.

Step 2:

Step 3:

Step 4:

Centrifuge reaction to remove insoluble material. Purify conjugate by spin column gel filtration in 50% DMSO-50% H$_2$O. Exchange to 100% aqueous solution via dialysis. Concentrate with a centricon. Passage through a 0.2 μm sterilizing filter.

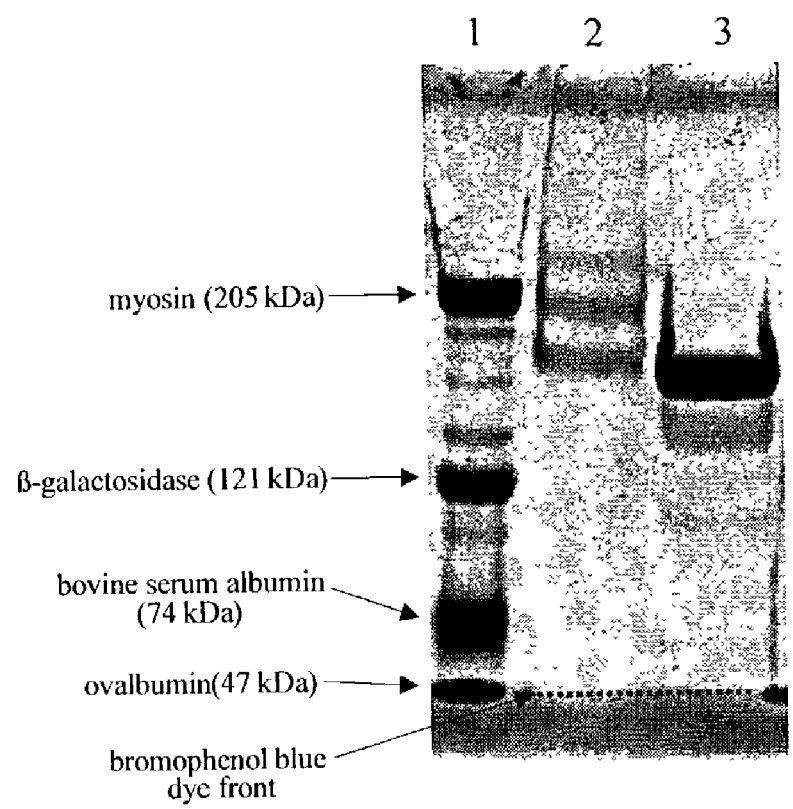

Figure 12
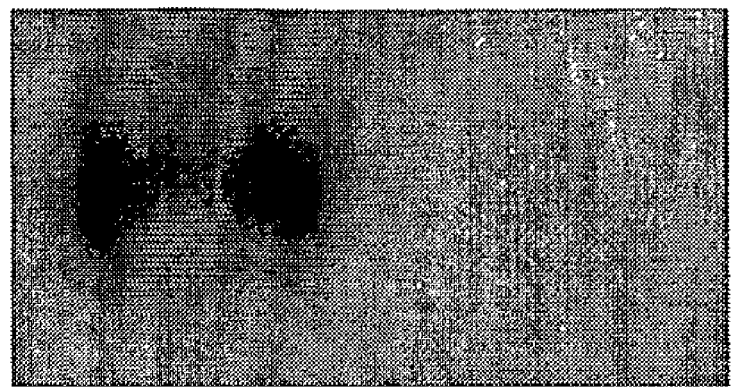
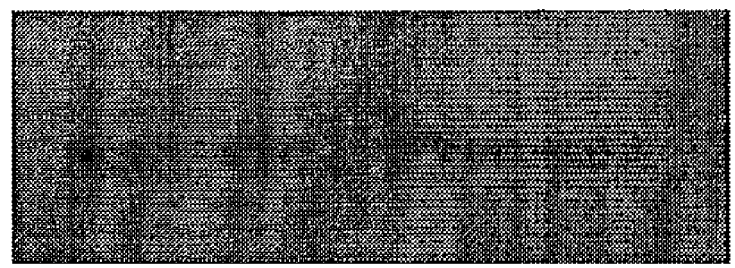

Figure 16
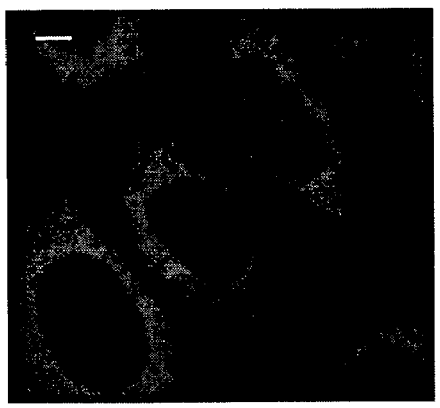
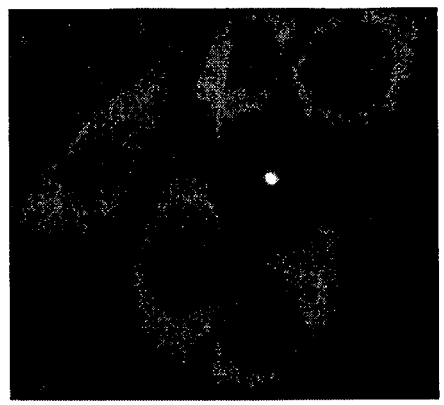
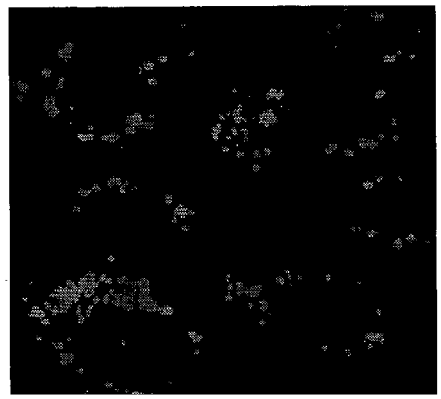
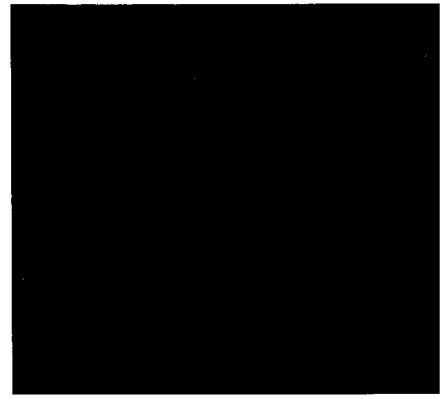

Figure 17
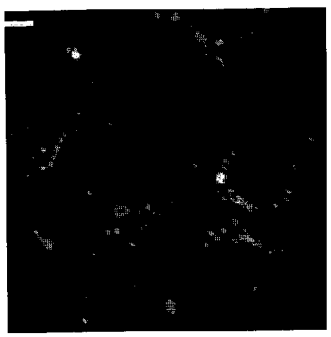
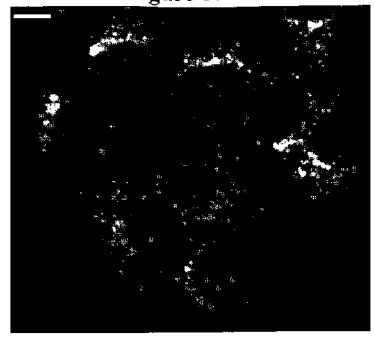
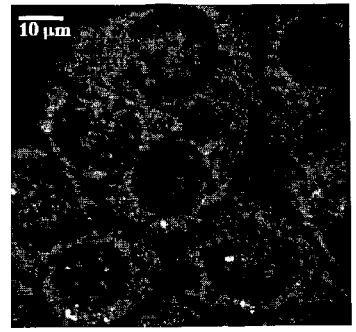
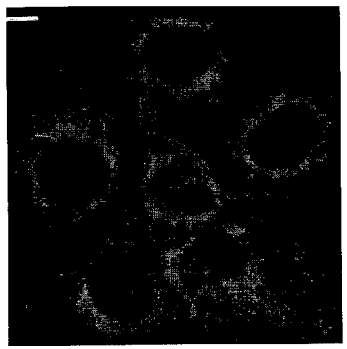

Figure 18

Tumor Burden Reduction Following Photoimmunotherapy
in an Intraperitoneal Murine Model for Human Ovarian Cancer

PHOTOIMMUNOTHERAPIES FOR CANCER USING COMBINATION THERAPIES

RELATED APPLICATIONS/PATENTS & INCORPORATION BY REFERENCE

This application claims priority to U.S. application Ser. No. 60/287,767, filed on May 1, 2001 and to U.S. application Ser. No. 60/338,961, filed on Dec. 7, 2001, both of which are hereby expressly incorporated by reference into this application.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. Documents incorporated by reference into this text may be employed in the practice of the invention.

STATEMENT OF RIGHTS TO INVENTIONS MADE UNDER FEDERALLY SPONSORED RESEARCH

This work was supported by the government, in part, by a grant from the National Institutes of Health, Grant No. RO1 AR40352. The government has certain rights to this invention.

FIELD OF THE INVENTION

The present invention relates to photosensitizer immunoconjugate compositions and combination therapies for use in cancer related photodynamic treatments and diagnostic methods. Other aspects of the invention are described in or are obvious from the following disclosure (and within the ambit of the invention).

BACKGROUND OF THE INVENTION

Photodynamic therapy (PDT) is an emerging modality for the treatment of neoplastic and non-neoplastic diseases. Using photodynamic therapeutic approaches, photosensitizers are localized in target tissues, and subsequently activated with an appropriate wavelength of light. Light activation of the photosensitizers generates active molecular species, such as free radicals and singlet oxygen ($^1O_2$), which are toxic to target cells and tissues. PDT is known to produce tumoricidal effects within malignant tissues. Tumors in virtually every anatomic site have been treated with PDT, and most are responsive to this therapy to some extent.

To date, several thousand patients have been treated with PDT for a variety of neoplasms. Randomized clinical trials of this modality were initiated in 1987, using a purified form of HPD, Photofrin® (Marcus, 1992), (Dougherty et al., 1998). These first randomized trials were sponsored by Quadra Logic Technologies, Inc. (now QLT Phototherapeutics, Vancouver, Canada) and American Cyanamid Co. (Pearl River, N.Y.), and compared the efficacy of PDT with that of other forms of therapy for bladder, esophageal, and lung cancers. Within the past 5 years, significant progress has been made worldwide in obtaining regulatory approval for a variety of indications. Currently, PDT with the photosensitizer Photofrin® is approved in at least 10 countries. Approval for treatment with other photosensitizers has been requested in the United States, Canada, and Europe.

PDT is a binary therapy, having the advantage of inherent dual selectivity. First, selectivity is achieved by an increased concentration of the photosensitizer in target tissue, and second, the irradiation can be limited to a specified volume. Provided that the photosensitizer is non-toxic, only the irradiated areas will be affected, even if the photosensitizer does bind to normal tissues. Selectivity thus obtained may be adequate for certain anatomical sites, such as skin and oral cavity, however, for more complex sites such as the peritoneal cavity, greater selectivity than that achievable with current photosensitizers is necessary, so that colateral damage to normal organs can be minimized. Selectivity can be even further enhanced by attaching photosensitizers to molecular delivery systems that have high affinity for target tissue (Hasan, 1992), (Strong et al., 1994). For example, one way to improve selectivity is to link the photosensitizer to a monoclonal antibody directed against cancer-associated antigens in an approach known as photoimmunotherapy (PIT). The resulting photoimmunoconjugate (PIC) delivers the photosensitizer directly to the tumor cell of interest.

The use of photosensitizer immunoconjugates (PICs) offers improved photosensitizer delivery specificity and could broaden the applicability of photodynamic therapy (PDT). For example, it has been suggested that PDT might be used effectively in the treatment of small diffuse malignancies present in a cavity, such as the peritoneum or bladder, if the photosensitizer could be made to accumulate with high specificity in malignant cells (Hamblin et al., 1996). This would allow photodynamic destruction of diseased cells while sparing adjacent normal tissues of sensitive organs.

Many monoclonal antibodies known in the art possess tumoricidal activity. The combined therapeutic use of a tumoricidal antibody and a photosensitizer compound is referred to herein as photodynamic combination therapy or "combination therapy."Combination therapies advantageously co-localize photosensitizer compounds and tumoricidal antibodies in tumor tissue. Combination therapies would include PICs wherein the monoclonal antibody component has an inhibitory effect on tumor growth. The inhibitory effects of a combination therapy comprising a tumoricidal antibody and a photosensitizer compound on tumor growth were heretofore unknown.

Tumoricidal antibodies, when used as monotherapy for reducing tumor growth, can have associated toxicity. Combination therapies requiring reduced levels of antibody administration can also reduce the occurrence of associated toxicity.

For complicated diseases, such as those involving intraperitoneal cancers, combination therapies are likely to prevail over standard treatment regimes (Duska et al., 1999). Ovarian cancer is one example of an intraperitoneal cancer where combination therapies have the potential to be of great use. Ovarian cancer ranks as the fourth most common malignancy in American women, responsible for more deaths than any other cancer in the female reproductive tract (Greenlee et al., 2000; Ozols, 1994). Only 25% of cases are detected at a localized state, with most patients presenting with late stage disease. Reported 5-year survival for advanced ovarian cancer is 28% (Greenlee et al., 2000). This rather poor prognosis reflects the negligible effect that both advances in surgical technique and chemotherapy have had over the past ten years in the treatment of ovarian cancer. Currently, advanced disease is treated by staging/debulking surgery, followed by chemotherapy. Approximately 50% of patients will have documented positive second look laparotomies following first line treatment (Bolis et al., 1996). Among those women with negative second look laparotomies, 50% will present later with disease recurrence (Bolis et al., 1996). Recurrent disease is rarely curable, since there are currently no effective salvage treatments that affect survival. New treatments are necessary for the management of advanced and recurrent epithelial ovarian cancer; however, new therapeutic approaches have been difficult to develop. Use of PICs and/or combination therapies can offer a new therapeutic approach to the treatment of many cancers, including ovarian cancers.

Although nearly 20 years has past since PICs were first conceived (Mew et al., 1983), no clinically useful PICs yet exist. Improved PICs would not only be of use in combination therapies, but in any application of PDT wherein selective delivery and accumulation of photosensitizers to a target tissue is desired. This would include, for example, diagnostic methods using PICs. Literature reviews of PIC research (Hasan, 1992), (Sternberg et al., 1998), (Yarmush et al., 1993), (Savellano, 2000), have concluded that a major impasse encountered in this field has been the synthesis and purification of functional, well-characterized conjugates.

Several major problems with the design, synthesis, and purification of PICs have not been dealt with satisfactorily in PIC investigations. In particular, many previous studies of PICs did not thoroughly investigate whether the photodynamic effects of the conjugate preparations were due to the specific action of the conjugates or whether they were due to the action of noncovalently-associated free photosensitizer impurities present in the conjugate preparations (Hasan, 1992), (Sternberg et al., 1998), (Savellano, 2000). This issue is one of the most cumbersome problems encountered in PIC research. Due to the hydrophobic and/or highly adsorptive nature of most PDT-type photosensitizers, it has been very difficult to remove unconjugated photosensitizer impurities from PIC preparations. Moreover, for similar reasons, it has been difficult to maintain solubility of the PIC preparations. Whereas the best photosensitizers are usually hydrophobic and lipophilic, antibodies and immunoconjugates must remain water-soluble and disaggregated in order to reach their designated targets in an efficient manner via the circulation.

Thus, for the most part, problems in the art are attributable to the incompatible solubilities of photosensitizers and antibodies. Because previous studies of PICs have not utilized conjugation methods that are capable of circumventing the incompatible solubilities of photosensitizers and antibodies, the conjugate preparations very likely contained significant amounts of aggregated material and noncovalently-associated free photosensitizer impurities. Consequently, interpretation of the observed biological effects of the PICs in these studies has been difficult, especially in in vitro studies, since the effects of the actual conjugates cannot be clearly distinguished from the effects of noncovalently-associated free photosensitizer impurities and/or large aggregates that may have been present in the PIC preparations. In turn, it has been difficult to discern what measures must be taken to improve the overall performance of PIC constructs.

The use of benzoporphyrin derivative (BPD) photosensitizers in PICs is highly desirable. For example, BPD Verteporfin, has been thoroughly characterized, (Richter et al., 1987), (Aveline et al., 1994), and it has been found to be a highly potent photosensitizer for PDT. Investigations using BPD PICs have been extensively reported in the literature (Levy et al., 1989), (Jiang et al., 1990), (Jiang, 1993). However, similar to studies involving other photosensitizers, studies of BPD-based conjugates did not convincingly demonstrate that the photodynamic activity of the PIC preparations was predominantly due to the activity of the conjugates and not due to the activity of free BPD impurity present in the PIC preparations. In addition, the conjugation protocols described in the literature for linking BPD directly to antibodies failed to produce functional, high purity conjugate preparations.

Methods of producing improved PICs through the covalent linkage of photosensitizers to antibodies were heretofore unknown. PICs that are free of undesirable photosensitizer contaminants will further the development of improved photodynamic therapies, including combination therapies, and diagnostic methods.

OBJECT AND SUMMARY OF THE INVENTION

It has now been shown that employing a dual mechanism of action against tumor growth and/or formation by way of a photodynamic combination therapy can synergistically increase the therapeutic efficacy of anti-cancer treatment regimes. Furthermore, combination therapies, as well as selective photodynamic therapies and diagnostic methods, can now utilize improved PICs. It has also now been shown that the incompatible solubilities of photosensitizers and antibodies that are problematic in the art can be overcome through the use of a "two-solvent" system or reaction mixture, and by the incorporation of a solubilizing agent, which results in the production of high purity PICs that are substantially free of noncovalently associated, free photosensitizer, e.g. that contain less than about 15% free photosensitizer impurity, preferably less than about 10%, more preferably less than about 5%.

The two-solvent system is a polar aprotic solvent (e.g., dimethyl sulfoxide (DMSO), tetrahydrofuran and acetonitrile)/aqueous mixture. The relative amounts of polar aprotic solvent and aqueous mixture in the two solvent system (polar aprotic solvent:aqueous mixture) is in the range of about 40% to about 60% by volume polar aprotic solvent: about 60% to about 40% by volume aqueous mixture, such as about 45% to about 55% by volume polar aprotic solvent: about 55% to about 45% by volume aqueous mixture, with preferred amounts of polar aprotic solvent and aqueous mixture in the two solvent system (polar aprotic solvent:aqueous mixture) being about 50% by volume polar aprotic solvent: about 50% by volume aqueous mixture. DMSO is the preferred polar aprotic solvent. The aqueous component may be water, phophate-buffered saline (PBS) or any other approximately neutral buffering solution known in the art.

The invention relates to a purified photosensitizer immunoconjugate composition comprising at least one photosensitizer and at least one solubilizing agent each independently bound to an antibody through a direct covalent linkage.

The invention further relates to a photosensitizer immunoconjugate composition comprising at least one photosensitizer covalently linked to an antibody, wherein the photosensitizer density on the antibody is sufficient to quench photoactivation while the composition is freely circulating throughout the bloodstream of a subject.

The invention further relates to an advantageously substantially pure photosensitizer immunoconjugate comprising at least one photosensitizer bound to an advantageously PEG (polyethylene glycol)ylated antibody, wherein the photosensitizer is covalently bound through an amide linkage to a lysine residue of the antibody.

The invention also involves a process for preparing a substantially pure photosensitizer immunoconjugate comprising purifying a photosensitizer immunoconjugate so that it has aggregates removed therefrom and/or non-covalently associated free photosensitizer removed therefrom; for instance, whereby the photosensitizer immunoconjugate is substantially free of non-covalently associated free photosensitizer.

The PIC can be prepared by conjugating antibodies, advantageously PEGylated antibodies, with a photosensitizer, advantageously an activated photosensitizer such as a photosensitizer ester, e.g. a photosensitizer-NHS ester; and advantageously purifying resulting conjugate, e.g. by removal of aggregates and/or removal of non-covalently associated free photosensitizer, e.g. so that the conjugate is substantially free of non-covalently associated free photosensitizer.

The antibodies can be prepared, for example, by conjugating them with PEG-NHS (N-hydroxysuccinimide) esters in a two solvent reaction mixture such that lysine residues are PEGylated. Preferably, four or fewer lysine residues are PEGylated. The activated photosensitizer can be made by making a reaction mixture comprising the photosensitizer and NHS in a solvent, preferably DMSO, and allowing the mixture to react at a sufficiently low temperature for a period of up to about 10 days. The conjugation of antibodies, for example PEGylated antibodies, and a photosensitizer, such as an activated photosensitizer-NHS ester, can be performed by incubating them in a two solvent reaction mixture for about two hours to form PICs comprising less than about twenty amide linkages between the unPEGylated lysine residues of each antibody and the photosensitizers.

The invention further relates to a soluble photosensitizer immunoconjugate composition comprising at least one photosensitizer and at least one solubilizing agent each independently bound to an antibody through a direct covalent linkage.

The invention further relates to a method of reducing tumor cell growth and/or proliferation in a subject comprising the steps of a) administering a therapeutically effective amount of a photosensitizer immunoconjugate composition comprising at least one photosensitizer and at least one solubilizing agent, each independently bound to an antibody through a direct covalent linkage, wherein the antibody binds with specificity to an epitope present on the surface of a tumor cell; and b) localizing the composition to the tumor cell; and c) light activating the composition to produce phototoxic species; and d) inhibiting the tumor cell growth and/or proliferation.

In another embodiment, the method of reducing tumor cell growth and/or proliferation in a subject is modified by using, instead of the photosensitizer immunoconjugate composition in step a) above, the composition comprises at least one photosensitizer and an antibody, wherein the antibody binds with specificity to an epitope present on the surface of a tumor cell and exerts an inhibitory effect on growth and/or proliferation of the tumor cell.

Alternatively, step a) above can be performed with a photosensitizer immunoconjugate composition comprising at least one photosensitizer directly linked to a first antibody, wherein the antibody binds with specificity to a first epitope present on the surface of a tumor cell, and a second antibody, wherein the antibody binds with specificity to a second epitope present on the surface of a tumor cell and exerts an inhibitory effect on growth of the tumor cell. The second antibody may also be a cocktail of different antibodies that bind to more than one epitope. Antibodies used in this way may be advantageous in that they can target more than one pathway.

In the context of the present invention, a "tumor cell" is a cancer cell or a mass of cancer cells, and can also encompass cells that support the growth and/or propagation of a tumor, such as vasculature and/or stroma. In the context of the present invention, a "cancer cell" comprises a cell undergoing oncogenic proliferation. See also, Kendrew, ed. The Encyclopedia of Molecular Biology (paperback edition, 1995), at 144-145 a definition of "cancer cells", incorporated herein by reference. For instance, therefore, the present invention envisages methods for reducing growth and/or proliferation of a tumor cell in a subject where the composition in step a) above is a photosensitizer and at least one solubilizing agent, each independently bound to an antibody through a direct covalent linkage, wherein the antibody binds with specificity to an epitope present on the surface of a cancer cell or a tumor-supporting cell that is involved in the growth and/or propagation of a cancer cell such as vasculature or blood vessels that supply tumors and/or tumor stroma, but not necessarily macrophages.

Another embodiment of the invention further relates to a method of reducing tumor cell growth and/or proliferation in a subject, wherein the composition of step a) above comprises at least one photosensitizer and at least one solubilizing agent, each independently bound to an antibody through a direct covalent linkage, wherein the antibody binds with specificity to an epitope present on the surface of a tumor cell.

These and other objects and embodiments are described in or are obvious from and within the scope of the invention, from the following Detailed Description.

BRIEF DESCRIPTION OF THE DRAWINGS

FIGS. 1A-D depict a representative sample of antibodies having tumoricidal activity and/or tumor-specific epitope binding activity.

FIG. 3 depicts the various species of a typical C225 PIC preparation.

FIG. 12 depicts a Western blot showing the expression of the human EGFR by the CHO-EGF through probing with its antibody.

FIG. 16 depicts the localization of BPD and C225 PIC in CHO-EGF cells and CHO-ErbB2 cells with confocal laser fluorescence microscopy.

FIG. 17 depicts the localization of BPD and C225 PIC in OVCAR-5 cells with confocal laser fluorescence microscopy.

FIG. 18 depicts inhibition of EGF-induced phosphorylation of the EGFR by treatment with either C225 or C225 PIC, as opposed to no inhibitory effect on EGF-induced phosphorylation of the EGFR by treatment with BPD plus light.

DETAILED DESCRIPTION

Figure 2A:
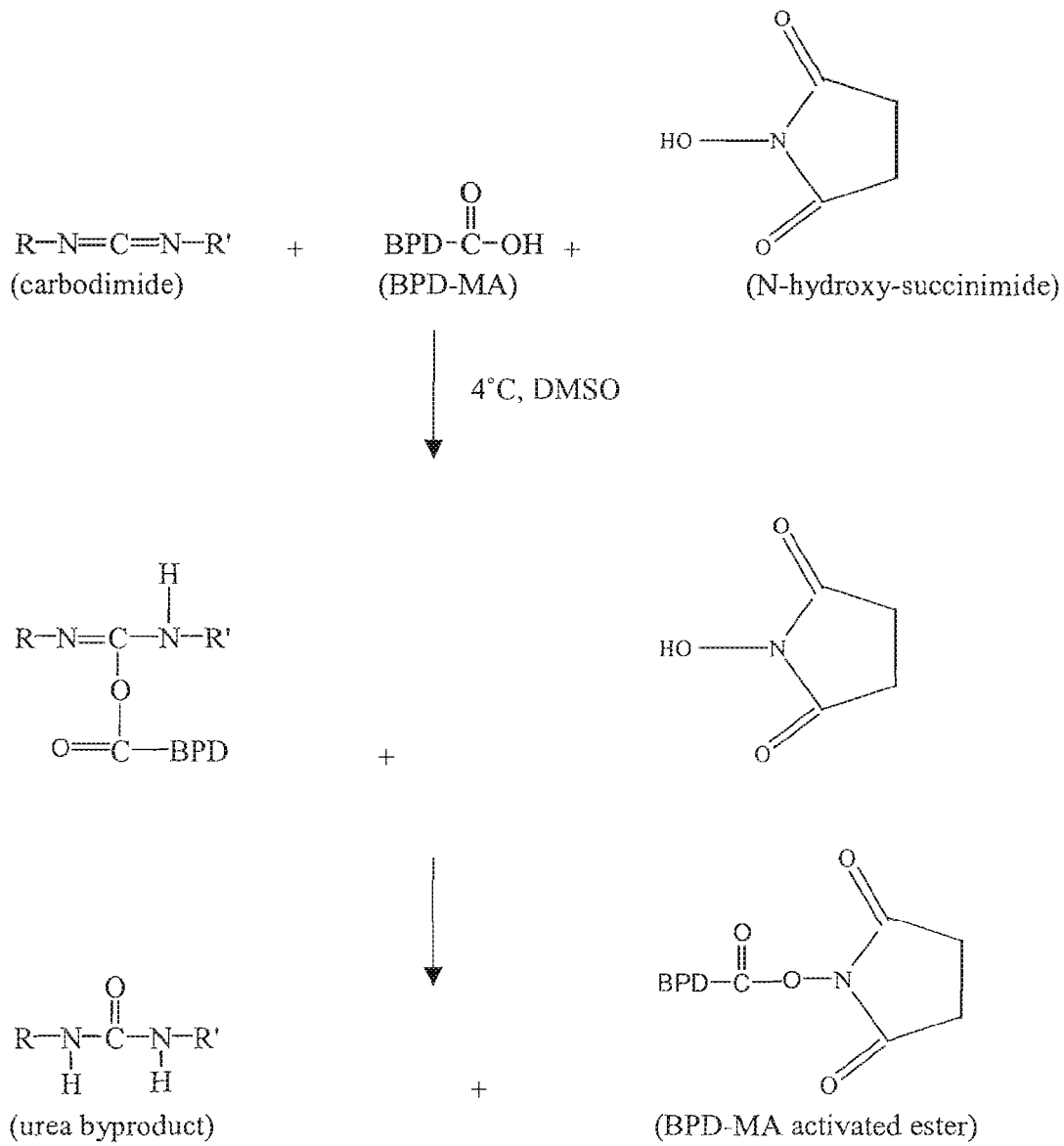
FIGS. 2A-C depict a conjugation reaction scheme for the synthesis and purification of PICs.

In one aspect, the invention relates to compositions of high purity PICs. Accordingly, an embodiment of the invention relates to a purified PIC composition comprising at least one photosensitizer and at least one solubilizing agent each independently bound to an antibody through a direct covalent linkage. Purified PICs of the invention are substantially free of impurities, in particular noncovalently-associated, free photosensitizer impurity is less than about 15%, preferably less than about 10%, most preferably less than about 5%.

The solubilizing agent can comprise, for example, polyethylene glycol (PEG). A wide variety of PEG derivatives are commercially available from Shearwater Polymers, Huntsville, Ala. Suitable PEG derivatives include a 10 kDa two-branched PEG-NHS ester. Preferably, the PIC comprises up to four PEGs per antibody.

In yet another embodiment, the invention relates to a PIC comprising at least one photosensitizer bound to a PEGylated antibody, wherein the photosensitizer is covalently bound through an amide linkage to a lysine residue of the antibody.

As used herein, "photosensitizer" means a chemical compound that produces a biological effect upon photoactivation or a biological precursor of a compound that produces a biological effect upon photoactivation. Photosensitizers of the invention can be any known in the art, including photofrin.RTM, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid benzonaphthoporphyrazines, cationic imminium salts, tetracyclines, lutetium texaphyrin, tin-etio-purpurin, porphycenes, benzophenothiazinium and combinations thereof.

In a preferred embodiment, the photosensitizer is a benzoporphyrin derivative ("BPD"), such as BPD-MA, also commercially known as BPD Verteporfin ("BPD"). U.S. Pat. No. 4,883,790 describes BPDs. BPD is a so-called second-generation compound which lacks the prolonged cutaneous phototoxicity of Photofrin® (Levy, 1994). BPD has been thoroughly characterized (Richter et al., 1987), (Aveline et al., 1994), and it has been found to be a highly potent photosensitizer for PDT.

The photosensitizers can comprise a plurality of the same photosensitizer, each covalently linked to the antibody. In a preferred embodiment, the PIC comprises less than twenty of the same photosensitizer, each covalently linked to the antibody.

The antibody component of the PIC can bind with specificity to an epitope present on the surface of a tumor cell. "Binding with specificity" means that noncancer cells are either not specifically bound by the antibody or are only poorly recognized by the antibody. The antibodies of the invention comprise whole native antibodies, bispecific antibodies; chimeric antibodies; Fab, Fab', single chain V region fragments (scFv) and fusion polypeptides. Preferably, the antibodies of the invention are monoclonal.

The term "antibody" as used in this invention includes intact immunoglobulin molecules as well as fragments thereof, such as Fab and Fab', which are capable of binding the epitopic determinant. Fab fragments retain an entire light chain, as well as one-half of a heavy chain, with both chains covalently linked by the carboxy terminal disulfide bond. Fab fragments are monovalent with respect to the antigen-binding site.

A representative sampling of tumor-specific antibodies is depicted in FIG. 1. For example, antibodies of the invention that bind to tumor cell epitopes include, but are not limited to, IMC-C225, EMD 72000, OvaRex Mab B43.13, 21B2 antibody, anti-human CEA, CC49, anti-ganglioside antibody G(D2) ch14.18, OC-125, F6-734, CO17-1A, ch-Fab-A7, BIWA 1, trastuzumab, rhuMAb VEGF, sc-321, AF349, BAF349, AF743, BAF743, MAB743, AB1875, Anti-Flt-4AB3127, FLT41-A, rituximab, tositumomab, Mib-1, 2C3, BR96, CAMPATH 1H, 2G7, 2A11, Alpha IR-3, ABX-EGF, MDX-447, SR1, Yb5.b8, 17F.11, anti-p75, anti-p64 IL-2R and MLS 102.

A wide variety of tumor-specific antibodies are known in the art, such as those described in U.S. Pat. Nos. 6,197,524, 6,191,255, 6,183,971, 6,162,606, 6,160,099, 6,143,873, 6,140,470, 6,139,869, 6,113,897, 6,106,833, 6,042,829, 6,042,828, 6,024,955, 6,020,153, 6,015,680, 5,990,297, 5,990,287, 5,972,628, 5,972,628, 5,959,084, 5,951,985, 5,939,532, 5,939,532, 5,939,277, 5,885,830, 5,874,255, 5,843,708, 5,837,845, 5,830,470, 5,792,616, 5,767,246, 5,747,048, 5,705,341, 5,690,935, 5,688,657, 5,688,505, 5,665,854, 5,656,444, 5,650,300, 5,643,740, 5,635,600, 5,589,573, 5,576,182, 5,552,526, 5,532,159, 5,525,337, 5,521,528, 5,519,120, 5,495,002, 5,474,755, 5,459,043, 5,427,917, 5,348,880, 5,344,919, 5,338,832, 5,298,393, 5,331,093, 5,244,801, and 5,169,774. See also The Monoclonal Antibody Index Volume 1: Cancer ($3^{rd}$ edition). Accordingly, tumor-specific antibodies of the invention can recognize tumors derived from a wide variety of tissue types, including, but not limited to, breast, prostate, colon, lung, pharynx, thyroid, lymphoid, lymphatic, larynx, esophagus, oral mucosa, bladder, stomach, intestine, liver, pancreas, ovary, uterus, cervix, testes, dermis, bone, blood and brain.

As used in this invention, the term "epitope" means any antigenic determinant on an antigen to which the antibody binds. Epitopic determinants usually consist of chemically active surface groupings of molecules such as amino acids or sugar side chains and usually have specific three dimensional structural characteristics, as well as specific charge characteristics. Epitopes of the invention can be present, for example, on cell surface receptors.

Epitopes to which tumor-specific antibodies bind are also well known in the art. For example, epitopes bound by the tumor-specific antibodies of the invention include, but are not limited to, those known in the art to be present on CA-125, gangliosides G(D2), G(M2) and G(D3), CD20, CD52, CD33, Ep-CAM, CEA, bombesin-like peptides, PSA, HER2/neu, epidermal growth factor receptor, erbB2, erbB3, erbB4, CD44v6, Ki-67, cancer-associated mucin, VEGF, VEGFRs (e.g., VEGFR3), estrogen receptors, Lewis-Y antigen, TGFβ1, IGF-1 receptor, EGFα, c-Kit receptor, transferrin receptor, IL-2R and CO17-1A.

The antibodies of this invention can be prepared in several ways. Methods of producing and isolating whole native antibodies, bispecific antibodies, chimeric antibodies, Fab, Fab', single chain V region fragments (scFv) and fusion polypeptides are known in the art. See, for example, Harlow and Lane (1988) *Antibodies: A Laboratory Manual*, Cold Spring Harbor Laboratory, New York (Harlow and Lane, 1988).

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology", "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

Antibodies are most conveniently obtained from hybridoma cells engineered to express an antibody. Methods of making hybridomas are well known in the art. The hybridoma cells can be cultured in a suitable medium, and spent medium can be used as an antibody source. Polynucleotides encoding the antibody can in turn be obtained from the hybridoma that produces the antibody, and then the antibody may be produced synthetically or recombinantly from these DNA sequences. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Another method of obtaining antibodies is to immunize suitable host animals with an antigen and to follow standard procedures for polyclonal or monoclonal production. Monoclonal antibodies (Mabs) thus produced can be "humanized" by methods known in the art. Examples of humanized antibodies are provided, for instance, in U.S. Pat. Nos. 5,530,101 and 5,585,089.

"Humanized" antibodies are antibodies in which at least part of the sequence has been altered from its initial form to render it more like human immunoglobulins. In one another version, the heavy chain and light chain C regions are replaced with human sequence. In another version, the CDR regions comprise amino acid sequences for recognition of antigen of interest, while the variable framework regions have also been converted to human sequences. See, for example, EP 0329400. In a third version, variable regions are humanized by designing consensus sequences of human and mouse variable regions, and converting residues outside the CDRs that are different between the consensus sequences. The invention encompasses humanized Mabs. The invention also encompasses hybrid antibodies, in which one pair of heavy and light chains is obtained from a first antibody, while the other pair of heavy and light chains is obtained from a different second antibody. Such hybrids may also be formed using humanized heavy and light chains.

Construction of phage display libraries for expression of antibodies, particularly the Fab or scFv portion of antibodies, is well known in the art (Heitner, 2001). The phage display antibody libraries that express antibodies can be prepared according to the methods described in U.S. Pat. No. 5,223,409 incorporated herein by reference. Procedures of the general methodology can be adapted using the present disclosure to produce antibodies of the present invention. The method for producing a human monoclonal antibody generally involves (1) preparing separate heavy and light chain-encoding gene libraries in cloning vectors using human immunoglobulin genes as a source for the libraries, (2) combining the heavy and light chain encoding gene libraries into a single dicistronic expression vector capable of expressing and assembling a heterodimeric antibody molecule, (3) expressing the assembled heterodimeric antibody molecule on the surface of a filamentous phage particle, (4) isolating the surface-expressed phage particle using immunoaffinity techniques such as panning of phage particles against a preselected antigen, thereby isolating one or more species of phagemid containing particular heavy and light chain-encoding genes and antibody molecules that immunoreact with the preselected antigen.

Single chain variable region fragments are made by linking light and heavy chain variable regions by using a short linking peptide. Any peptide having sufficient flexibility and length can be used as a linker in a scFv. Usually the linker is selected to have little to no immunogenicity. An example of a linking peptide is $(GGGGS)_3$, which bridges approximately 3.5 nm between the carboxy terminus of one variable region and the amino terminus of another variable region. Other linker sequences can also be used. All or any portion of the heavy or light chain can be used in any combination. Typically, the entire variable regions are included in the scFv. For instance, the light chain variable region can be linked to the heavy chain variable region. Alternatively, a portion of the light chain variable region can be linked to the heavy chain variable region, or a portion thereof. Compositions comprising a biphasic scFv could be constructed in which one component is a polypeptide that recognizes an antigen and another component is a different polypeptide that recognizes a different antigen, such as a T cell epitope.

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector for the production of scFvs is pcDNA3 (Invitrogen, San Diego, Calif.) in mammalian cells, described above.

Expression conditions should ensure that the scFv assumes functional and, preferably, optimal tertiary structure. Depending on the plasmid used (especially the activity of the promoter) and the host cell, it may be necessary or useful to modulate the rate of production. For instance, use of a weaker promoter, or expression at lower temperatures, may be necessary or useful to optimize production of properly folded scFv in prokaryotic systems; or, it may be preferable to express scFv in eukaryotic cells.

Antibody purification methods may include salt precipitation (for example, with ammonium sulfate), ion exchange chromatography (for example, on a cationic or anionic exchange column preferably run at neutral pH and eluted with step gradients of increasing ionic strength), gel filtration chromatography (including gel filtration HPLC), and chromatography on affinity resins such as protein A, protein G, hydroxyapatite, and anti-immunoglobulin.

In yet another embodiment, the antibody component of the PIC is a tumoricidal antibody. The term "tumoricidal antibody" as used herein refers to an antibody that inhibits tumor cell growth and/or proliferation through epitope binding. Antibodies that possess tumoricidal activity are also known in the art, including IMC-C225, EMD 72000, OvaRex Mab B43.13, anti-ganglioside G(D2) antibody ch14.18, CO17-1A, trastuzumab, rhuMAb VEGF, sc-321, AF349, BAF349, AF743, BAF743, MAB743, AB1875, Anti-Flt-4AB3127, FLT41-A, rituximab, 2C3, CAMPATH 1H, 2G7, Alpha IR-3, ABX-EGF, MDX-447, anti-p75 IL-2R, anti-p64 IL-2R, and 2A11.

In the context of the present invention, a tumor cell is a cancer cell or a mass of cancer cells, which can also encompass cells that support the growth and/or propagation of a cancer cell, such as vasculature and/or stroma, but not necessarily macrophages. For instance, therefore, the present invention envisages compositions and methods for reducing growth of a tumor cell in a subject, wherein tumoricidal antibodies bind with specificity to cell surface epitopes (or epitopes of receptor-binding molecules) of a cancer cell or a cell that is involved in the growth and/or propagation of a cancer cell such as a cell comprising the vasculature of a tumor or blood vessels that supply tumors and/or stromal cells.

In a preferred embodiment, the antibody component of the PIC is IMC-C225, a chimeric therapeutic antibody made to the extracellular domain of the EGFR, which has shown great success in the treatment of head and neck cancer when administered in combination with radiation (Fan and Mendelsohn., 1998). Autocrine activation of the EGFR by EGF and TGF-α is important to tumor cell proliferation, and the EGFR appears to be an excellent target for anti-cancer therapies given that it is overexpressed in several types of tumors such as ovarian, colon, lung, and oral cancer (Perkins, 1997).

PICs of the present invention target tumor cell(s). A tumor cells comprises one or more cancer cells, or a mass of cancer cells, and can also encompass cells that support the growth and/or propagation of a cancer cell, such as vasculature and/or stroma, but not necessarily macrophages. For instance, therefore, the present invention envisages compositions and methods for reducing growth and/or proliferation of a tumor cell in a subject, wherein tumoricidial antibodies bind with specificity to cell surface epitopes (or epitopes of receptor-binding molecules) of a cancer cell or a cell that is involved in the growth and/or propagation of a cancer cell such as a cell within the vasculature of a tumor or blood vessels that supply tumors and/or stromal cells.

For example, the lymphatic system is the primary pathway for the metastasis of most cancers. Activation of lymphatic endothelium by lymphangiogenic factors directly influences tumor progression by promoting tumor cell invasion and migration into the lymphatic vessels. VEGF-C and VEGF-D are members of the vascular endothelial growth factor (VEGF) family of angiogenic growth factors that have been identified as growth factors for lymphatic vessels. The induction of tumor lymphangiogenesis by VEGF-C results in increased infiltration of lymphatic vessels by tumor cells, and the extent of intratumoral lymphangiogenesis directly relates to the extent of tumor metastases. VEGFR-3, the receptor for VEGF-C and VEGF-D, is expressed in all tumor-associated lymphatic vessels and has been implicated in tumor lymphangiogenesis.

In a preferred embodiment, the antibody component of the PIC comprises an antibody to VEGFR-3. Tumoricidial antibodies to VEGFR-3 are known in the art. For example, sc-321 is commercially available from Bioscience (Santa Cruz, Calif.). Tumoricidial antibodies to VEGFR-3 include, but are not limited to AF349, BAF349, AF743, BAF743, MAB743, AB1875, Anti-Flt-4AB3127, and FLT41-A. PICs comprising tumoricidial antibodies to VEGFR-3 can be localized to the lymphatic vessels and selectively activated with light at the tumor site, causing local lymphatic vessel eradication.

In yet another embodiment, the invention relates to a PIC comprising at least one photosensitizer covalently linked to an antibody, wherein the photosensitizer density on the antibody is sufficient to quench photoactivation while the composition is freely circulating throughout the bloodstream of a subject. In this regard, "sufficient to quench photoactivation" means that the photosensitizer molecules are packed densely enough on the antibody to ensure that dequenching cannot occur until PICs are intracellularly localized. Intracellular localization of the PIC occurs through various routes, including receptor-mediated endocytosis. The high-density PICs are dequenched upon intracellular localization into target tumor cells. Intracellular dequenching of the PIC is mediated through hydrolytic and/or enzymatic processes (e.g. lysosomal degradation) and results in enhanced photoactivation upon administration of light. High-density PICs are less susceptible to photodynamic activation outside of target tumor cells, and thereby produce less collateral damage by way of background photoactivation in normal tissues.

In a preferred embodiment, the antibody component of the high-density PIC binds with specificity to a receptor or an epitope of a receptor-binding molecule present on the surface of a tumor cell. Antibodies of this category include, but are not limited to, IMC-C225, EMD 72000, BIWA 1, trastuzumab, rituximab, tositumomab, 2C3, rhuMAb VEGF, sc-321, AF349, BAF349, AF743, BAF743, MAB743, AB1875, Anti-Flt-4AB3127, FLT41-A, CAMPATH 1H, 2G7, alpha IR-3, ABX-EGF, MDX-447, SR1, Yb5.B8, 17F.11, anti-p75 IL-2R and anti-p64 IL-2R. Receptor epitopes or an epitope of a receptor-binding molecule include, but are not limited to those known in the art to be present on CD20, CD52, CD33, HER2/neu, epidermal growth factor receptor, erbB3, erbB4, CD44v6, VEGF, VEGFRs (e.g., VEGFR-3), estrogen receptors, TGFβ1, IGF-1 receptor, EGFα, c-Kit receptor, transferrin receptor, and IL-2R.

In yet another embodiment, binding of the antibody component of the high-density PIC to the receptor epitope or an epitope of a receptor binding molecule inhibits growth and/or proliferation of the tumor cell. Tumoricidal antibodies in this category include, but are not limited to, IMC-C225, EMD 72000, trastuzumab, rituximab, 2C3, rhuMAb VEGF, sc-321, AF349, BAF349, AF743, BAF743, MAB743, AB1875, Anti-Flt-4AB3127, FLT41-A, CAMPATH 1H, 2G7, alpha IR-3, ABX-EGF, MDX-447, anti-p75 IL-2R and anti-p64 IL-2R.

In yet another aspect, the invention relates to processes for producing high purity PIC compositions. To overcome the problems in the art relating to incompatible solubilities of photosensitizers and antibodies, three significant improvements over prior art methods are described herein. First, conjugation of PICs with a solubilizing agent maintained solubility and prevented aggregation of the conjugates in predominantly aqueous solutions. Second, the utilization of a two-solvent system of approximately 50% DMSO/50% aqueous facilitated efficient covalent linkage of photosensitizers to the antibody and in addition, thorough purification of the resulting PICs. Third, high purity, activated photosensitizer-NHS esters were developed to improve conjugation efficiency and avoid undesirable side reactions that diminish the specific binding activity of the antibody. These advances permitted the production of high purity PICs that contained less than about 10% free photosensitizer impurity.

Accordingly, an embodiment of the invention relates to a process for the preparation of photosensitizer immunoconjugates comprising any or all of the following steps:
a) conjugating antibodies with PEG-NHS esters for a duration of about 1.5 hours in a two solvent reaction mixture comprising approximately equal parts DMSO and an aqueous dilute buffered salt solution, wherein about 4 or fewer lysine residues per antibody are PEGylated;
b) preparing activated photosensitizer-NHS esters in a suitable organic solvent for up to about 10 days at a sufficiently low temperature;
c) purifying the activated photosensitizer-NHS esters;
d) adding the purified, activated photosensitizer-NHS esters from step c) into the reaction mixture to obtain a final concentration in the range of about 0.025 to about 0.25 mM;
e) conjugating antibodies, advantageously PEGylated antibodies, with a photosensitizer, advantageously an activated photosensitizer, e.g. a photosensitizer-NHS ester, in the reaction mixture for a duration of about two hours to form photosensitizer immunoconjugates comprising less than about twenty amide linkages between the unPEGylated lysine residues of each antibody and the photosensitizers; and
f) advantageously purifying resulting conjugate, e.g. by removal of aggregates and/or removal of non-covalently associated free photosensitizer, e.g. so that the conjugate is substantially free of non-covalently associated free photosensitizer.

The process can comprise a cocktail of photosensitizers, consisting of multiple varieties. The cocktail can include, for example several photosensitizers known in the art. The process can also comprise a single variety of photosensitizer. Preferably, photosensitizers of the process comprise BPD. The process can likewise comprise a cocktail of tumor-specific antibodies, with or without tumoricidal activity. The process accommodates all antibodies of the invention, including whole native antibodies, bispecific antibodies, chimeric antibodies, humanized antibodies, Fab, Fab', single chain V region fragments (scFv) and fusion polypeptides; subtle adjustments can be made to the amounts of the various reactants that are well within the skill of those in the art. The process can also comprise a single variety of antibody. Preferably, antibodies of the process comprise IMC-C225. Another preferred antibody is ABX-EGF, which is a humanized anti-EGF-R antibody.

In the reaction mixture, a soluble photosensitizer immunoconjugate composition comprising at least one photosensitizer and at least one solubilizing agent each independently bound to an antibody through a direct covalent linkage is maintained. The solubilizing agent can comprise PEG, a PEG derivative, various types of carbohydrates, and/or other synthetic hydrophilic polymers such as N-(2-hydroxypropyl) methacrylamide copolymers and poly(N-isopropylacrylamide) polymers.

Preferably, an antibody is first conjugated with a PEG-NHS ester for a duration of about 1.5 hours in a two solvent reaction mixture comprising about 50% DMSO and 50% aqueous dilute buffered salt solution that is mildly basic in the pH range of about 7 to 8. The aqueous solution can comprise, for example, 25% Dulbecco's phosphate buffered solution without $Ca^{2+}$ or $Mg^{2+}$.

The two-solvent reaction mixture can comprise a polar aprotic solvent other than DMSO (e.g., tetrahydrofuran and acetonitrile), the solvent can be present at a range of about 40-60% by volume, preferably at about 50%. The aqueous component may be water, phophate-buffered saline (PBS,) or any other approximately neutral buffering solution known in the art.

Figure 2B:
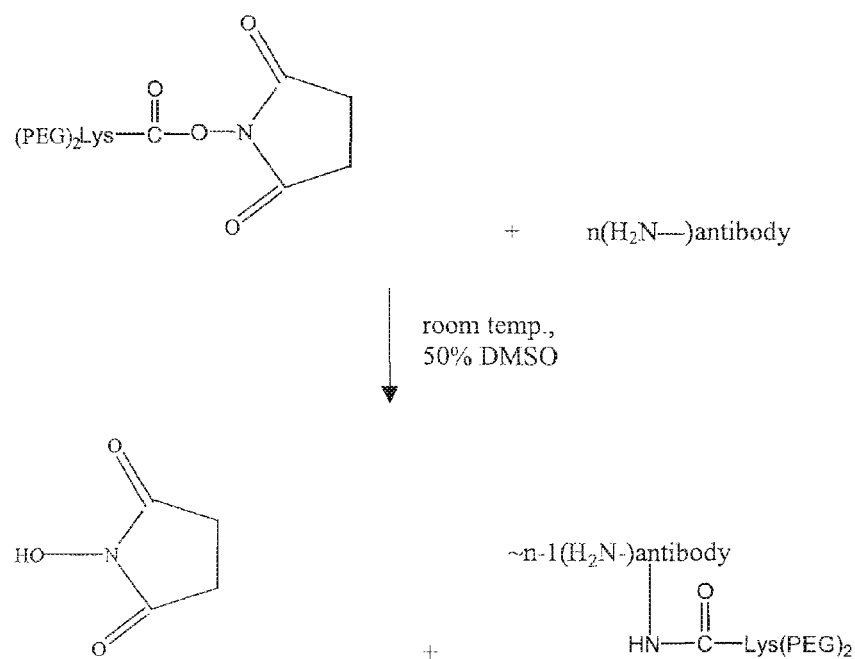
Figure 2C:
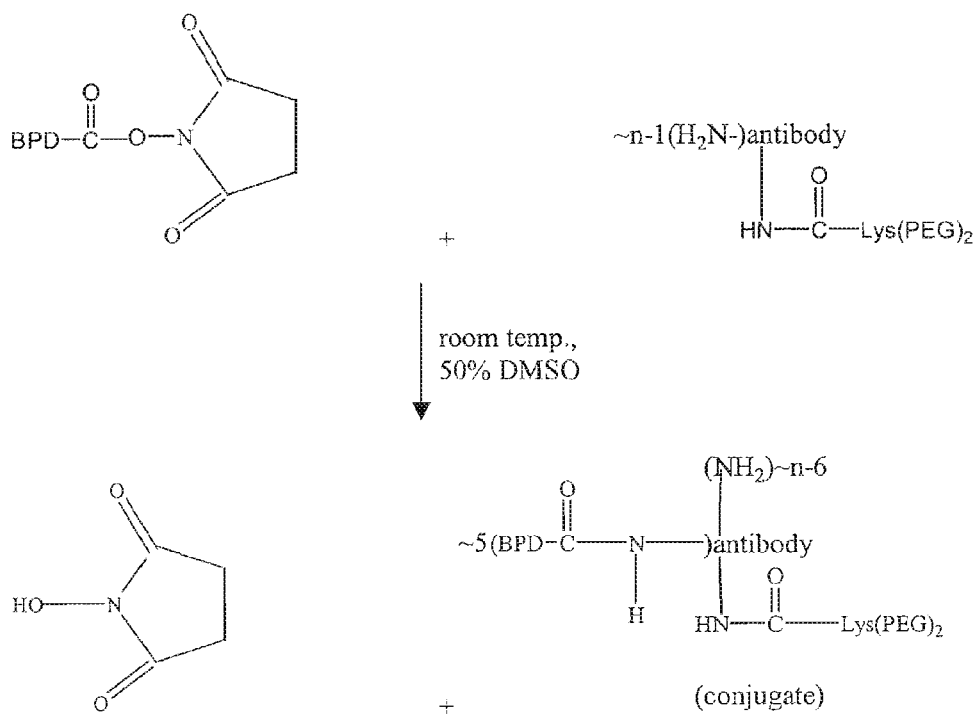

Addition of a suitable amount of solubilizing agent advantageously overcomes PIC aggregation, maintains PIC solubility without disruption of the antibody's antigen binding activity, and reduces reticulo-endothelial system capture of the PIC. For example, unPEGylated PICs gradually form large insoluble aggregates during long-term storage in about 50% DMSO solutions, and it is not possible to transfer concentrated solutions of unPEGylated PICs from about 50% DMSO to purely aqueous solutions without forming large insoluble aggregates. To overcome solubility problems, the antibody component of the PIC should be conjugated to a solubility agent, such as a two-branched PEG-NHS ester prior to labeling with photosensitizer-NHS ester. Moreover, in vitro experiments demonstrated that macrophage uptake of PEGylated PICs is significantly lowered by comparison to macrophage uptake of unPEGylated PICs. FIG. 2 depicts a PEGylation reaction scheme. Advantageously, the PEGylation reaction time can be extended or reduced by up to or no more than about 30 minutes. It is advantageous that the reaction time not be too short, for example, anything considerably less than about 1 hour risks the possibility that the PEGylation reaction does not approach completion, and it is preferred that incomplete PEGylation be avoided.

Preferably, PEG-NHS:antibody molar ratios in the conjugation reaction are approximately 2 to 5. The degree of attachment of PEG to the antibody, which can be accomplished by the reaction of PEG-NHS active ester with antibody lysine residues to form stable, covalent amide bonds, is controlled by regulation of the amount of PEG-NHS ester added to the reaction mixture. Addition of PEG-NHS ester to obtain a final concentration of approximately 0.015 to 0.04 mM results in PEGylation of up to about 4 lysine residues per antibody. About 4 or fewer PEGs per antibody enhances overall PIC solubility while allowing sufficiently high packing of the photosensitizer onto the PIC and at the same time avoiding any significant losses in the antibody's antigen binding activity. Depending on the particular antibody of interest, one of skill in the art could vary the parameters to achieve more or less PEGylation, so long as the antigen binding activity of the PIC is maintained.

The PICs of the process can comprise a plurality of the same photosensitizer, each covalently linked to the antibody. In a preferred embodiment, the PIC comprises the covalent linkage of up to about twenty molecules of the same photosensitizer per antibody. Depending on the particular antibody of interest, one of skill in the art could vary the parameters to achieve more or less photosensitizer conjugation, so long as the antigen binding activity of the PIC is maintained.

Prior to addition into the reaction mix, activated photosensitizer-NHS esters are prepared in DMSO for up to about 10 days at a sufficiently low temperature, not to exceed about 10° C., and most preferably, not to exceed about 4° C. Temperatures below about 4° C. are appropriate, but should not drop below a point where the reaction can no longer be driven. One of skill in the art would readily be able to determine the point at which the reaction reaches completion. These conditions produce photosensitizer-NHS esters in high yield (greater than about 50% yield) without generating significant amounts of undesirable side products.

Activated photosensitizer-NHS esters, preferably N-hydroxysuccinimide active ester derivatives, can be synthesized by various methods. For example, the NHS active ester of BPD can be prepared in DMSO by mixing approximately 6 volumes of about 5 mg/ml BPD in its free mono-acid form (about 6.96 mM) with approximately 5 volumes of freshly prepared about 5 mg/ml NHS (about 43.4 mM) and approximately 5 volumes of freshly prepared about 5 mg/ml EDC (about 26.1 mM). Prior to conjugation, crude photosensitizer-NHS product can be purified by various methods. Specifically, the crude BPD-NHS active ester can be purified by silica gel chromatography with ethyl acetate as the elutant and methylene chloride as the loading solvent. Following evaporation of ethyl acetate from the recovered product, the purified BPD-NHS can then be reconstituted in DMSO for use in conjugation reactions. Preferably, activated photosensitizer-NHS esters are purified prior to their use in conjugations. Using purified photosensitizer-NHS preparations in the conjugation reactions advantageously permits higher photosensitizer:antibody molar loading ratios without sacrificing PIC purity and/or the integrity of the antibody's antigen binding activity.

Following conjugation of the antibody to a solubility agent, the purified, activated photosensitizer-NHS ester is introduced into the conjugation reaction mixture. Use of an approximately 50% DMSO/50% aqueous two-solvent system is advantageous in that it diminishes the tendency of the photosensitizer to aggregate and bind noncovalently to the PIC. During mixing of the various reactants, care should be taken to avoid exposing the antibody to greater than approximately 50% DMSO content, in order to prevent denaturation and/or precipitation of the protein. Use of an approximately 50% DMSO/50% aqueous two-solvent system allows efficient generation of high purity PICs with BPD:antibody molar loading ratios ranging from approximately 2 up to about 11. The yield of the photosensitizer conjugation reaction is approximately 75% for the preparation of PICs with BPD:antibody molar loading ratios of about 2. The photosensitizer conjugation reaction yield drops below approximately 45% for the preparation of PICs with BPD:molar loading ratios greater than about 10. Nevertheless, the observed reaction yields for conjugations that are carried out in the approximately 50% DMSO/50% aqueous two solvent system are substantially higher by comparison to the observed reaction yields for conjugations that are carried out in predominantly aqueous solutions.

Formation of covalent amide linkages between the photosensitizer and the antibody lysine residues can be controlled by regulation of the amount of photosensitiser-NHS ester added to the reaction mixture. Addition of the photosensitizer-NHS ester to obtain a final concentration in the range of about 0.025 to about 0.25 mM results in the formation of up to approximately twenty covalent amide linkages per PIC. The reaction should continue for a duration of at least two hours to ensure that the reaction of the photosensitizer active ester with the antibody lysine groups has gone to completion.

After a total reaction period of about 3.5 hours, the conjugation reaction mixture is purified. Purification can comprise centrifugation of the reaction mixture to remove insoluble material, followed by gel filtration purification. Gel filtration can be carried out, for example, on a Sephadex G-50 (medium particle size, Amersham Pharmacia Biotech Inc., Piscataway, N.J.) spun column (Sambrook, 1989), equilibrated in approximately 50% DMSO/50% de-ionized/distilled $H_2O$. At this stage, the purified PIC can be stored in approximately 50% DMSO/50% aqueous solution at about 4° C. and remain stable at least for several months.

Prior to use the PIC preparations can be diluted with PBS to approximately 5% DMSO content and then concentrated and exchanged to a purely aqueous PBS solution using a 50 kDa Molecular Weight (MW) cut-off Centricon centrifugal filter device. PIC preparations exchanged to purely aqueous PBS can be stored at about 4° C., remaining stable at least for several months.

If deemed necessary, the PIC preparations can be sterile filtered using a 0.2 μm filter membrane. To reduce the loss of the PIC resulting from non-specific PIC adsorption to the filter membrane, approximately 1 mg of serum albumin for every approximately 100 μg of conjugate can be added to the PIC preparations prior to sterile filtering. The addition of serum albumin to the PIC preparations can be carried out by diluting the PIC preparations in approximately 50% DMSO solutions to approximately 5% DMSO content using about 10 mg/ml stock solution of serum albumin in PBS. This mixture can be concentrated and exchanged to a purely aqueous PBS solution using a 50 kDa MW cut-off Centricon centrifugal filter device.

The purity of the PIC preparations can be assessed by SDS-PAGE analysis. With attention to detail and proper handling, it is possible to obtain PIC preparations that contain less than about 10% residual free photosensitizer impurity, or preferably, less than about 5% residual free photosensitizer impurity.

In yet another aspect, the invention relates to combination therapy methods of treatment. The combined therapeutic use of a tumoricidal antibody and a photosensitizer compound is referred to herein as photodynamic combination therapy or "combination therapy." Accordingly, an embodiment of the invention relates to a method of reducing tumor cell growth and/or proliferation in a subject comprising the steps of a) administering a therapeutically effective amount of at least one photosensitizer composition, wherein the photosensitizer composition is taken up by a tumor cell;

b) administering a therapeutically effective amount of an antibody composition, wherein the antibody binds with specificity to an epitope present on the surface of a tumor cell and exerts an inhibitory effect on growth and/or proliferation of the tumor cell;

c) localizing the antibody composition to a tumor cell;

d) light activating the tumor cell to produce phototoxic species; and
e) inhibiting growth and/or proliferation of the tumor cell.

Yet another embodiment of the invention relates to a method of reducing tumor cell growth and/or proliferation in a subject comprising the steps of
a) administering a therapeutically effective amount of a PIC composition comprising at least one photosensitizer and at least one solubilizing agent, each independently bound to an antibody through a direct covalent linkage, wherein the antibody binds with specificity to an epitope present on the surface of a tumor cell;
b) localizing the composition to the tumor cell;
c) light activating the composition to produce phototoxic species; and
d) inhibiting the tumor cell growth and/or proliferation.

A further embodiment of the invention relates to a method of reducing tumor cell growth and/or proliferation in a subject comprising the steps of
a) administering a therapeutically effective amount of a photosensitizer immunoconjugate composition comprising at least one photosensitizer directly linked to a first antibody; wherein the antibody binds with specificity to a first epitope present on the surface of a tumor cell;
b) localizing the photosensitizer immunoconjugate composition to the tumor cell;
c) administering a therapeutically effective amount of a second antibody, wherein the antibody binds with specificity to a second epitope present on the surface of a tumor cell and exerts an inhibitory effect on growth and/or proliferation of the tumor cell;
d) localizing the second antibody to the tumor cell;
e) light activating the tumor cell to produce phototoxic species; and
f) inhibiting growth and/or proliferation of the tumor cell.

The photosensitizer compositions of these methods can be any known in the art. In a preferred embodiment, the photosensitizer used in any one method is BPD.

The PICs of any one method can comprise a cocktail of photosensitizers, consisting of multiple varieties. The cocktail can include, for example several photosensitizers known in the art. The process can also comprise a single variety of photosensitizer. Thus, PICs can comprises a plurality of the same photosensitizer, each covalently linked to the antibody. Preferably, the PICs comprise less than twenty of the same photosensitizer, each covalently linked to the antibody. Preferably, photosensitizers of the PICs comprise BPD.

The PICs of any one method can comprise at least one photosensitizer and at least one solubilizing agent each independently bound to an antibody through a direct covalent linkage. The photosensitizer can be covalently bound, for example, through an amide linkage to a lysine residue of the antibody. The PICs of any one method can further comprise at least one photosensitizer covalently linked to an antibody, wherein the photosensitizer density on the antibody is sufficient to quench photoactivation while the composition is freely circulating throughout the bloodstream of a subject. Advantageously, these high-density PICs are dequenched following intracellular localization. Dequenching can occur, for example, by proteolytic, hydrolytic, or enzymatic intracellular processes, such as lysosomal degradation. For methods of combination therapy comprising administration of a PIC and a tumoricidal antibody, the direct linkage between the first antibody and the photosensitizer can comprise a polymer or a polypeptide. Polymers of interest include, but are not limited to polyamines, polyethers, polyamine alcohols, derivitized to components by means of ketones, acids, aldehydes, isocyanates or a variety of other groups. Polypeptide linkages can comprise, for example poly-L-lysine linkages. (Del Governatore et al., 2000), (Hamblin et al., 2000a), (Molpus et al., 2000).

A wide variety of tumor-specific antibodies are known in the art. The antibody component of the PIC can bind with specificity to an epitope present on the surface of a tumor cell. Tumoricidal antibodies that bind with specificity to an epitope present on the surface of a tumor cell can be administered alone or in combination with a PIC also comprising a tumoricidal antibody recognizing a different epitope (the antibody and PIC should not compete with each other). The PIC composition administered to a subject can comprise a cocktail of tumor-specific antibodies, with or without tumoricidal activity, wherein the antibody component of the PICs, and optionally, the photosensitizer component, is variable from among the PIC of the composition. The cocktail would comprise only antibodies wherein epitope binding is non-competitive.

Methods of this invention are particularly suitable for administration to humans with neoplastic diseases. Especially relevant are melanoma, neuroblastoma, glioma, sarcoma, lymphoma, ovarian, prostate, colorectal and small cell lung cancers. The methods comprise administering an amount of a pharmaceutical composition containing PICs, tumoricidal antibodies and/or photosensitizers effective to achieve the desired effect, be it palliation of an existing tumor mass or prevention of recurrence.

An "individual", "patient" or "subject" is a vertebrate, preferably a mammal, more preferably a human. Mammals include, but are not limited to, humans, farm animals, sport animals, and pets.

The compositions of the invention, including PICs, photosensitizers and tumoricidal antibodies can be administered in a pharmaceutically acceptable excipient, such as water, saline, aqueous dextrose, glycerol, or ethanol. The compositions can also contain other medicinal agents, pharmaceutical agents, adjuvants, carriers, and auxiliary substances such as wetting or emulsifying agents, and pH buffering agents.

Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages is within the skill of one in the art given the parameters herein.

A "therapeutically effective amount" is an amount sufficient to effect a beneficial or desired clinical result. A therapeutically effective amount can be administered in one or more doses. In terms of treatment, an effective amount is an amount that is sufficient to palliate, ameliorate, stabilize, reverse or slow the progression of a cancerous disease (e.g. tumors, dysplaysias, leukemias) or otherwise reduce the pathological consequences of the cancer. A therapeutically effective amount can be provided in one or a series of administrations. In terms of an adjuvant, an effective amount is one sufficient to enhance the immune response to the immunogen. The effective amount is generally determined by the physician on a case-by-case basis and is within the skill of one in the art.

As a rule, the dosage for in vivo therapeutics or diagnostics will vary. Several factors are typically taken into account when determining an appropriate dosage. These factors include age, sex and weight of the patient, the condition being treated, the severity of the condition and the form of the antibody being administered.

The dosage of the PIC compositions and/or tumoricidal antibody compositions can vary from about 0.01 mg/m$^2$ to about 500 mg/m$^2$, preferably about 0.1 mg/m$^2$ to about 200 mg/m$^2$, most preferably about 0.1 mg/m$^2$ to about 10 mg/m$^2$. Ascertaining dosage ranges is well within the skill of one in the art. For example, in phase three clinical studies, IMC-C225 loading in human patients was between 100-500 mg/m$^2$, and maintenance was between 100-250 mg/m$^2$ (Waksal, 1999). The dosage of photosensitizer compositions can range from about 0.1 to 10 mg/kg. Methods for administering photosensitizer compositions are known in the art, and are described, for example, in U.S. Pat. Nos. 5,952,329, 5,807,881, 5,798,349, 5,776,966, 5,789,433, 5,736,563, 5,484,803 and by (Sperduto et al., 1991), (Walther et al., 1997). Such dosages may vary, for example, depending on whether multiple administrations are given, tissue type and route of administration, the condition of the individual, the desired objective and other factors known to those of skill in the art. For instance, the concentration of scFv typically need not be as high as that of native antibodies in order to be therapeutically effective. Administrations can be conducted infrequently, or on a regular weekly basis until a desired, measurable parameter is detected, such as diminution of disease symptoms. Administration can then be diminished, such as to a biweekly or monthly basis, as appropriate.

Compositions of the present invention are administered by a mode appropriate for the form of composition. Available routes of administration include subcutaneous, intramuscular, intraperitoneal, intradermal, oral, intranasal, intrapulmonary (i.e., by aerosol), intravenously, intramuscularly, subcutaneously, intracavity, intrathecally or transdermally, alone or in combination with tumoricidal antibodies. Therapeutic compositions of PICs are often administered by injection or by gradual perfusion.

Compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, compositions are preferably supplied in unit dosage form suitable for administration of a precise amount. Also contemplated by this invention are slow release or sustained release forms, whereby a relatively consistent level of the active compound are provided over an extended period.

Another method of administration is intralesionally, for instance by direct injection directly into the tumor. Intralesional administration of various forms of immunotherapy to cancer patients does not cause the toxicity seen with systemic administration of immunologic agents (Fletcher and Goldstein, 1987), (Rabinowich et al., 1987), (Rosenberg et al., 1986), (Pizza et al., 1984).

For methods of combination therapy comprising administration of a PIC and a tumoricidal antibody or administration of a photosensitizer and a tumoricidal antibody, the order in which the compositions are administered is interchangeable. Concomitant administration is also envisioned.

Methods of the invention are particularly suitable for use in treating and imaging brain cancer. When the site of delivery is the brain, the therapeutic agent must be capable of being delivered to the brain. The blood-brain barrier limits the uptake of many therapeutic agents into the brain and spinal cord from the general circulation. Molecules which cross the blood-brain barrier use two main mechanisms: free diffusion and facilitated transport. Because of the presence of the blood-brain barrier, attaining beneficial concentrations of a given therapeutic agent in the CNS may require the use of specific drug delivery strategies. Delivery of therapeutic agents to the CNS can be achieved by several methods.

One method relies on neurosurgical techniques. In the case of gravely ill patients, surgical intervention is warranted despite its attendant risks. For instance, therapeutic agents can be delivered by direct physical introduction into the CNS, such as intraventricular, intralesional, or intrathecal injection. Intraventricular injection can be facilitated by an intraventricular catheter, for example, attached to a reservoir, such as an Ommaya reservoir. Methods of introduction are also provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes (Neuwelt and Rapoport, 1984), (Baba et al., 1991), (Gennuso et al., 1993).

Further, it may be desirable to administer the compositions locally to the area in need of treatment; this can be achieved, for example, by local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford Pharmaceuticals Inc.

Methods of the invention are also particularly suitable for use in primary treatment of intraperitoneal cancers, such as ovarian and colorectal cancers and cancer of the bladder. Other potential uses include those where combination therapies could be combined with surgical debulking, such as pleural mesothelioma or advanced stage ovarian cancer. Currently, advanced ovarian cancer is treated by staging/debulking surgery, followed by chemotherapy, which is usually a combination of Taxol and platinum-based regimen. Rather than chemotherapy, combination therapy could instead be administered. For example, an administration scheme is envisioned whereby a-PIC composition is administered either before or after maximal debulking and subsequently light activated following the surgical procedure in order to eliminate residual cancer cells. In addition, administration of a photosensitizer or PIC composition, followed by maximal debulking, administration of a tumoricidal antibody, and subsequent light activation is also envisioned.

As used herein, "photoactivation" means a light-induced chemical reaction of a photosensitizer, which produces a biological effect. Photoactivating light can be delivered to the tumor site from a conventional light source or from a laser. Target tissues are illuminated, usually with red light from a laser. Given that red and/or near infrared light best penetrates mammalian tissues, photosensitizers with strong absorbances in the approximately 600 nm to 900 nm range are optimal for PDT. Delivery can be direct, by transillumination, or by optical fiber.

Optical fibers can be connected to flexible devices such as balloons equiped with light scattering medium. Flexible devices can include, for example, laproscopes, arthroscopes and endoscopes.

Following administration of the photosensitizer or PIC composition, it is necessary to wait for the photosensitizer to reach an effective tissue concentration at the tumor site before photoactivation. Duration of the waiting step varies, depending on factors such as route of administration, tumor location, and speed of photosensitizer movement in the body. In addition, where PICs target receptors or receptor binding epitopes, the rate of photosensitizer uptake can vary, depending on the level of receptor expression and/or receptor turnover on the tumor cells. For example, where there is a high level of receptor expression, the rate of PIC binding and uptake is increased. The waiting period should also take into account the rate at which PICs are degraded and thereby dequenched in the target tissue. Determining a useful range of waiting step duration is within ordinary skill in the art and may be optimized by utilizing fluorescence optical imaging techniques.

Following the waiting step, the photosensitizer and/or PIC composition is activated by photoactivating light applied to the tumor site. This is accomplished by applying light of a suitable wavelength and intensity, for an effective length of time, specifically to the lesion site. The suitable wavelength, or range of wavelengths, will depend on the particular photosensitizer(s) used. Wavelength specificity for photoactivation depends on the molecular structure of the photosensitizer. Photoactivation occurs with sub-ablative light doses. Determination of suitable wavelength, light intensity, and duration of illumination is within ordinary skill in the art.

The light for photoactivation can be produced and delivered to the tumor site by any suitable means. For superficial tumors or open surgical sites, suitable light sources include broadband conventional light sources, broad arrays of light emitting diodes (LED), and defocussed laser beams.

For non-superficial lesion sites, including those in intracavitary settings, the photoactivating light can be delivered by optical fiber devices. For example, the light can be delivered by optical fibers threaded through small gauge hypodermic needles. Optical fibers also can be passed through arthroscopes, endoscopes and laproscopes. In addition, light can be transmitted by percutaneous instrumentation using optical fibers or cannulated waveguides.

Photoactivation at non-superficial lesion sites also can be by transillumination. Some photosensitizers can be activated by near infrared light, which penetrates more deeply into biological tissue than other wavelengths. Thus, near infrared light is advantageous for transillumination. Transillumination can be performed using a variety of devices. The devices can utilize laser or non-laser sources, i.e. lightboxes or convergent light beams.

For photoactivation, the wavelength of light is matched to the electronic absorption spectrum of the photosensitizer so that photons are absorbed by the photosensitizer and the desired photochemistry can occur. Except in special situations, where the tumors being treated are very superficial, the range of activating light is typically between approximately 600 and 900 nm. This is because endogenous molecules, in particular hemoglobin, strongly absorb light below about 600 nm and therefore capture most of the incoming photons (Parrish, 1978). The net effect would be the impairment of penetration of the activating light through the tissue. The reason for the 900 nm upper limit is that energetics at this wavelength may not be sufficient to produce $^1O_2$, the activated state of oxygen, which without wishing to necessarily be bound by any one theory, is perhaps critical for successful PDT. In addition, water begins to absorb at wavelengths greater than about 900 nm. While spatial control of illumination provides specificity of tissue destruction, it can also be a limitation of PDT. Target sites must be accessible to light delivery systems, and issues of light dosimetry need to be addressed (Wilson, 1989). In general, the amenability of lasers to fiberoptic coupling makes the task of light delivery to most anatomic sites manageable, although precise dosimetry remains complex and elusive.

The effective penetration depth, $\delta_{eff}$, of a given wavelength of light is a function of the optical properties of the tissue, such as absorption and scatter. The fluence (light dose) in a tissue is related to the depth, d, as: $e^{-d/\delta_{eff}}$. Typically, the effective penetration depth is about 2 to 3 mm at 630 nm and increases to about 5 to 6 nm at longer wavelengths (e.g., 700-800 nm) (Svaasand and Ellingsen, 1983). These values can be altered by altering the biologic interactions and physical characteristics of the photosensitizer. Factors such as self-shielding and photobleaching (self-destruction of the photosensitizer during the PDT) further complicate precise dosimetry. In general, photosensitizers with longer absorbing wavelengths and higher molar absorption coefficients at these wavelengths are more effective photodynamic agents.

PDT dosage depends on various factors, including the amount of the photosensitizer administered, the wavelength of the photoactivating light, the intensity of the photoactivating light, and the duration of illumination by the photoactivating light. Thus, the dose of PDT can be adjusted to a therapeutically effective dose by adjusting one or more of these factors. Such adjustments are within ordinary skill in the art.

In yet another aspect, the invention relates to diagnostic methods utilizing PICs. Accordingly, an embodiment of the invention relates to a method of detecting a tumor cell in a subject comprising the steps of a) administering a photosensitizer immunoconjugate composition comprising at least one photosensitizer and at least one solubilizing agent each independently bound to an antibody through a direct covalent linkage, wherein the antibody binds with specificity to an epitope present on the surface of a tumor cell;

b) localizing the composition to the tumor cell;

c) light activating the composition to illuminate the tumor cell; and d) identifying the tumor cell.

The photosensitizers of this method can be any known in the art. In selecting a photosensitizer for diagnostic purposes, fluorochromic properties of the photosensitizer are of greater importance than photochemical properties. The PICs of this method can comprise a cocktail of photosensitizers, consisting of multiple varieties. The cocktail can include, for example several photosensitizers known in the art. The process can also comprise a single variety of photosensitizer. Thus, PICs can comprise a plurality of the same photosensitizer, each covalently linked to the antibody. Preferably, the PICs comprise less than about twenty of the same photosensitizer, each covalently linked to the antibody. Preferably, photosensitizers of the PICs comprise BPD.

A wide variety of tumor-specific antibodies are known in the art. The antibody component of the PIC can bind with specificity to an epitope present on the surface of a tumor cell. The PIC composition administered to a subject can comprise a cocktail of tumor-specific antibodies, wherein the antibody component of the PICs, and optionally, the photosensitizer component, is variable. The cocktail would comprise only antibodies wherein epitope binding is non-competitive.

The PICs of this method can comprise at least one photosensitizer and at least one solubilizing agent each independently bound to an antibody through a direct covalent linkage. The photosensitizer can be covalently bound, for example, through an amide linkage to a lysine residue of the antibody. The PICs of this method can further comprise at least one photosensitizer covalently linked to an antibody, wherein the photosensitizer density on the antibody is sufficient to quench photoactivation while the composition is freely circulating throughout the bloodstream of a subject. Advantageously, these high-density PICs are dequenched following intracellular localization and degradation by proteolytic enzymes, as previously described herein. PICs of the invention are of high purity, and are thus ideal for diagnostic applications requiring a high degree of specificity.

A wide variety of tumor-specific antibodies are known in the art. The antibody component of the PIC can bind with specificity to an epitope present on the surface of a tumor cell. Compositions embodied in this invention can be assessed for their ability to recognize specifically a tumor cell or tumor cell-specific epitope. Testing can be carried out in vitro, and preferably in vivo. In vivo test compounds are prepared as a suitable pharmaceutical composition and administered to test subjects. Initial studies are preferably done in small animals such as mice or rabbits, optionally next in non-human primates and then ultimately in humans. Such testing is within the skill of one in the art (Del Governatore et al., 2000), (Hamblin et al., 2000a), (Molpus et al., 2000).

Methods of administration and photoactivation for diagnostic applications are as described for combination therapies.

The present invention is additionally described by way of the following illustrative, non-limiting Examples, that provide a better understanding of the present invention and of its many advantages.

EXAMPLES

Example 1

Preparation and Characterization of the PICs.

Efforts over the past two decades to develop clinically useful PICs for use in photodynamic therapy (PDT) have been unsuccessful. The lack of success is due, in part, to the hydrophobic and aggregative properties of porphyrin-type photosensitizers, which invariably present solubility and purity problems. Another shortcoming has been the lack of a proper target antigen. The target antigen must allow delivery of sufficient amounts of photosensitizer to the lesion such that phototoxicity can be achieved using clinically practical light doses. The results presented herein encompass several measures taken to successfully overcome these problems.

Cell Lines and Antibodies

A-431 human epidermoid carcinoma cells and J774A.1 (J774) mouse monocyte-macrophage cells were obtained from American Type Culture Collection (ATCC CRL-1555 and ATCC TIB-67, respectively; Rockville, Md.). 3T3-NR6 (NR6) cells, an EGFR-negative variant cell line derived from the 3T3-Swiss albino embryonic mouse fibroblast cell line (Pruss, 1977) were a generous gift from Dr. A. Wells (Department of Pathology, University of Alabama, Birmingham, Ala.). J774 cells were grown in RPMI 1640 containing 10% heat-inactivated fetal bovine serum. A-431 cells were grown in DMEM containing 4.5 g/L glucose and 10% heat-inactivated fetal bovine serum. NR6 cells were grown in DMEM containing 1.0 g/L glucose and 10% heat-inactivated fetal bovine serum. All cell growth media were supplemented with 100 units/ml penicillin and 100 µg/ml streptomycin. Cells were maintained in an incubator at 37° C. in an atmosphere of 5% carbon dioxide. C225 anti-EGFR chimeric monoclonal antibody was a generous gift from ImClone Systems Incorporated (Somerville, N.J.). Rabbit IgG was obtained from Sigma-Aldrich (St. Louis, Mo.).

Antibodies were prepared as 10 mg/ml stock solutions in phosphate-buffered saline (PBS; essentially, Dulbecco's phosphate-buffered solution (DPBS) without $Ca^{2+}$ and $Mg^{2+}$), pH 7.4. C225 antibody, supplied as a 2 mg/ml stock solution was concentrated to 10 mg/ml and exchanged to PBS using a 50 kDa MW cut-off Centricon centrifugal filter device (Centricon YM-50, Millipore Corp., Bedford, Mass.). Rabbit IgG, supplied as a lyophilized powder, was dissolved in PBS to 10 mg/ml.

Preparation of PEGylated BPD Verteporfin PICs

BPD was a generous gift from QLT PhotoTherapeutics Incorporated (Vancouver, B.C., Canada). The activated NHS ester of BPD was synthesized in DMSO by mixing 6 volumes of 5 mg/ml BPD in its free mono-acid form (6.96 mM) with 5 volumes of freshly prepared 5 mg/ml NHS (43.4 mM) and 5 volumes of freshly prepared 5 mg/ml 1-ethyl-3,3'-dimethyl aminopropyl carbodiimide (EDC) (26.1 mM). In order to obtain the BPD-NHS ester in high yield without generating significant amounts of undesirable side products (Bodanszky, 1993), (Bauminger and Wilchek, 1980), the reaction was maintained at 4° C. for about 10 days. Following the extended reaction period, the mixture was dried down and washed and extracted with water and methylene chloride three times. The extracted crude BPD-NHS product was then purified by silica gel chromatography with ethyl acetate as the elutant and methylene chloride as the loading solvent. Ethyl acetate was evaporated from the recovered product, and the purified BPD-NHS was then reconstituted in DMSO at roughly 2.5 mM concentration, as verified by absorbance measurements. (The extinction coefficient of BPD in DMSO is 36,500 $M^{-1}cm^{-1}$ at 690 nm. It was assumed that BPD and BPD-NHS have similar absorption characteristics in this solvent at this wavelength.) Purified BPD-NHS was stored at or below −20° C. until it was needed for the conjugation reaction.

To overcome the photosensitizer's tendencies to self-aggregate and bind noncovalently to the hydrophobic pockets of proteins, conjugations were conducted in a 50% DMSO/50% aqueous two-solvent system at room temperature. A 50% DMSO/50% aqueous two-solvent system was determined to be optimal for synthesis and purification of PICs. In solubility studies, free BPD transitioned from a predominantly aggregated state to a predominantly disaggregated monomeric state as the solution composition was increased above approximately 40% DMSO. Antibody stability studies in DMSO/aqueous buffered solutions demonstrated that the antibody remains soluble and stabile in aqueous solutions containing DMSO content of up to 50%, and that the antibody aggregates and denatures irreversibly when DMSO content is increased above approximately 60%.

Conjugation reactions were conducted at room temperature. During mixing of the various reactants, care was taken to avoid exposing the antibody to greater than 50% DMSO content, in order to prevent protein denaturation and/or precipitation. First, antibody was conjugated with a 10 kDa two-branched PEG-NHS ester (Shearwater Polymers, Huntsville, Ala.) by reacting 400 µg of antibody (equivalent to 40 µl of a 10 mg/ml stock in PBS) with either 54 µg or 108 µg of the PEG-NHS ester (equivalent to 2 µl or 4 µl of a 27 mg/ml stock in DMSO; stored at −20° C. until needed) in a total volume of approximately 290 µl. (For Fab fragments, combining 560 µg of Fab with 270 µg of PEG-NHS in 143 µl DMSO was determined to be sufficient.) Although it was not necessary to PEGylate the PICs in order to maintain their solubility in 50% DMSO solutions during short-term storage periods of a few days, unPEGylated PICs gradually formed large insoluble aggregates during long-term storage in 50% DMSO solutions. In addition, it was not possible to transfer a concentrated solution of unPEGylated PICs from 50% DMSO to purely aqueous solutions without forming large insoluble aggregates. To overcome these problems, antibody was PEGylated with a special two-branched PEG-NHS ester prior to labeling with BPD-NHS ester. The PEGylation reaction yields a mixture of various species in a typical C225 PIC preparation (FIG. 3). The average PEG:antibody molar ratios of the PICs were approximately 2 to 3.

Following a 1.5 hour reaction period, varying amounts of the BPD-NHS active ester were added to the reaction mixture, ranging from 2 µl up to 30 µl of a 2.5 mM BPD-NHS stock solution in DMSO. (PEGylated Fab fragments were reacted with 1.985 mM BPD-NHS) The reaction was then allowed to proceed for another 2 hours. After a total reaction period of 3.5 hours, the conjugation reaction mixture was centrifuged at 16,000 g for 5 minutes to remove any insoluble material. The crude PIC preparation was then purified on a 3 ml Sephadex G-50 (medium particle size, Amersham Pharmacia Biotech Inc., Piscataway, N.J.) spun column (Sambrook, 1989), equilibrated in 50% DMSO/50% de-ionized/distilled $H_2O$. At this stage, the purified PIC could be stored in 50% DMSO at 4° C. Under these storage conditions, the PIC preparations remained stable at least for several months. Prior to use in cell culture experiments, the PIC preparations were usually diluted with PBS to 5% DMSO content and then concentrated and exchanged to a purely aqueous PBS solution using a 50 kDa MW cut-off Centricon centrifugal filter device. PEGylated PIC preparations that had been exchanged to purely aqueous PBS were stored at 4° C. and remained stable at least for several months.

If deemed necessary, the PIC preparations were sterile filtered using a 0.2 µm filter membrane. However, to reduce the loss of the PIC resulting from non-specific PIC adsorption to the filter membrane, approximately 1 mg of serum albumin for every 100 µg of conjugate was added to the PIC preparations prior to sterile filtering. The addition of serum albumin to the PIC preparations was usually accomplished by diluting the PIC preparations in 50% DMSO solutions to 5% DMSO content using a 10 mg/ml stock solution of serum albumin in PBS. This mixture was then concentrated and exchanged to a purely aqueous PBS solution using a 50 kDa MW cut-off Centricon centrifugal filter device.

Estimation of the BPD:Antibody Molar Loading Ratios of the PICs

Ground state absorption spectra were measured using a HP 8453 UV-visible spectrophotometer (Hewlett Packard GmbH, Waldbronn, Germany). To estimate the BPD content of a PIC preparation, the ~690 nm absorbance peak of the PIC was compared to the ~690 nm absorbance peak of free BPD standards in 50% DMSO/50% aqueous solutions. The protein content of the PIC was then measured by a Bradford-type protein assay (Bio-Rad Laboratories, Hercules, Calif.). Alternatively, the protein content of the PIC was estimated by subtracting away the BPD contribution to the PIC absorbance at 280 nm. This approximate measure of the protein contribution to the PIC absorbance could then be compared to the 280 nm absorbance of unmodified antibody standard samples.

Figure 4:
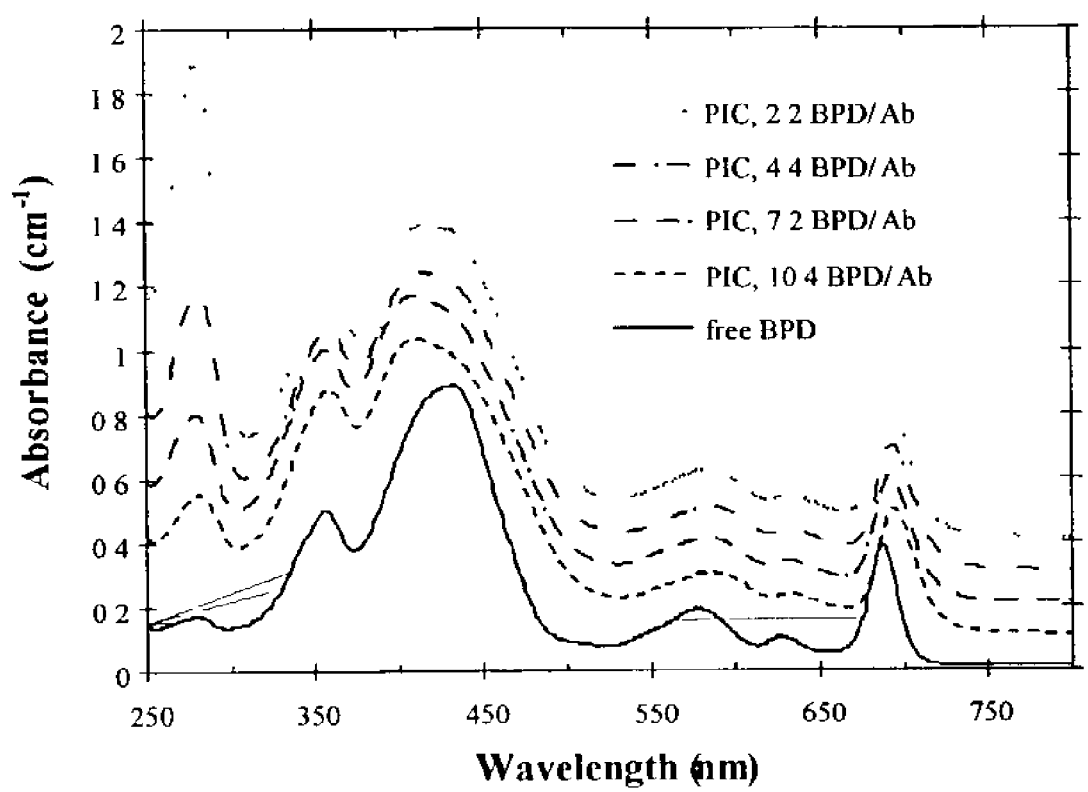
FIG. 4 depicts the absorbance spectra of a series of C225 PICs with varying BPD:Ab molar loading ratios.

Use of a 50% DMSO/50% aqueous two-solvent system allowed the preparation of high purity PICs with BPD:Ab molar loading ratios ranging from approximately 2 up to 11. The purity of the PIC preparations, assessed by SDS-PAGE analysis, was always less than 3 to 8% residual free photosensitizer impurity. Typical absorbance spectra of a series of C225 PICs with varying BPD:Ab molar loading ratios are shown in FIG. 4. The spectra show that the protein absorption peak at 280 nm gradually decreases in the expected manner relative to the photosensitizer absorption peaks as the PIC loading ratio increases. The photosensitizer conjugation reaction yield for the preparation of PICs with BPD:Ab molar loading ratios of 2 was approximately 75%. The photosensitizer conjugation reaction yield dropped below 45% for the preparation of PICs with BPD:molar loading ratios greater than 10. Only PIC preparations with residual free photosensitizer impurity of less than about 10% were used in cell studies, in order to investigate the activity of the PICs rather than the activity of free photosensitizer impurity present in the PIC preparations.

SDS-PAGE Analysis of the PICs

PIC preparations were studied using SDS-PAGE analysis. The PICs were analyzed using an SDS-discontinuous buffer system (Mini-PROTEAN II cell electrophoresis unit, Bio-Rad Laboratories, Hercules, Calif.), based on the method of Laemmli (Laemmli, 1970), (Hames and Rickwood, 1996). 12-14% gels under reducing conditions were utilized to resolve the heavy and light chains of the PICs and to assess qualitatively the extent of intra-antibody crosslinking and/or aggregation. In addition, 5% gels under non-reducing conditions were utilized to resolve the various levels of PEGylation of the PICs, to assess qualitatively the extent of inter-antibody aggregation, and to quantify the residual amounts of free photosensitizer impurity in the final PIC preparations. Gels were imaged and analyzed using a computerized CCD camera gel-viewing system (ChemiImager, Alpha Innotech Corporation, San Leandro, Calif.). PICs and free BPD were seen as green bands with white light transillumination and as red fluorescent bands with UV light excitation. The UV light source was filtered with 2 cm of 250 g/L $CuSO_4.5H_2O$ to remove the background infrared radiation of the lamps, and the red fluorescent bands on the gel were detected using a long wavelength pass filter (>620 nm). Following fluorescence imaging, gels were Coomassie stained and imaged using white light transillumination in order to visualize antibody protein content and protein marker bands.

Figure 5:
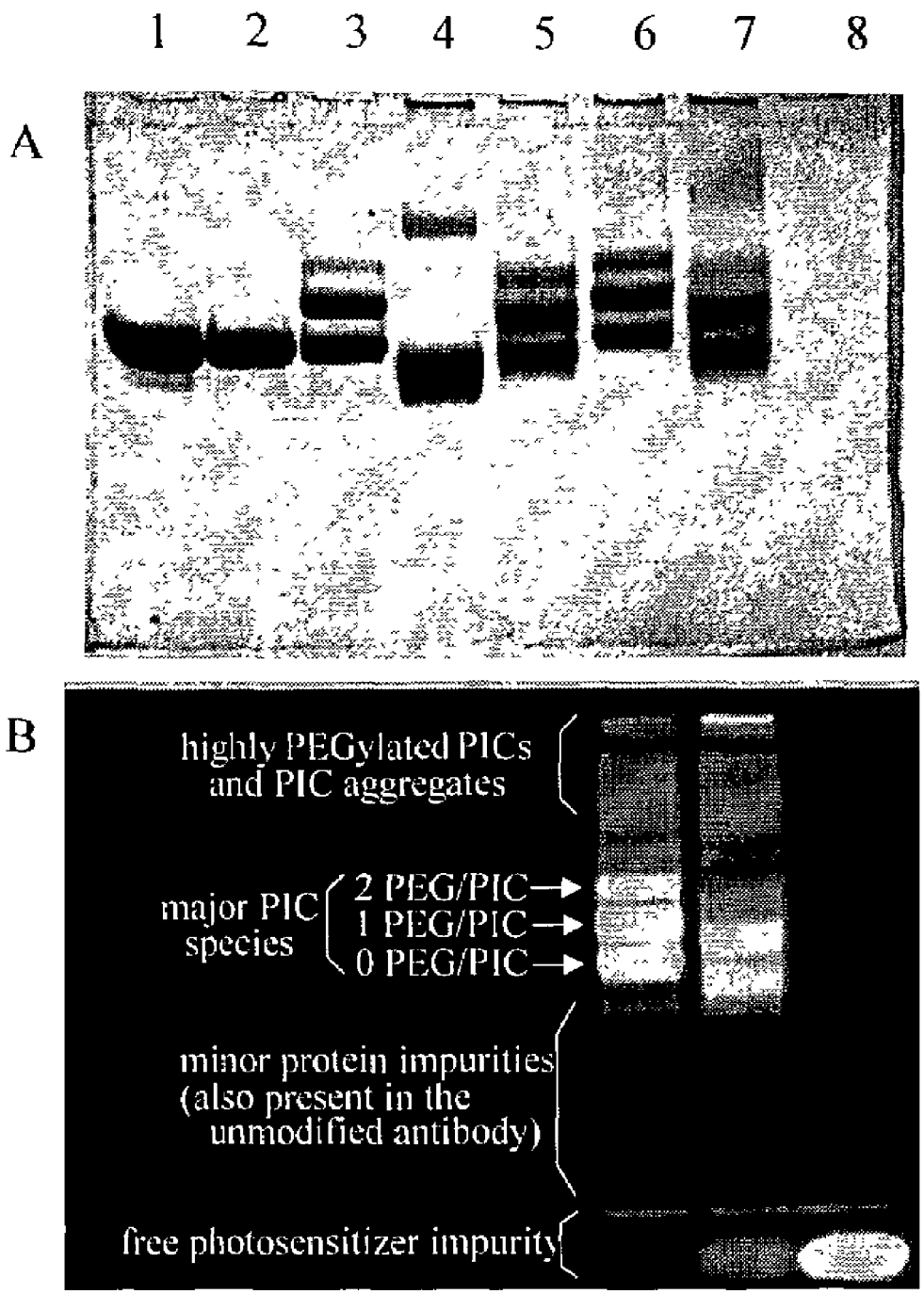
FIG. 5 depicts the antibody migration characteristics on a non-reducing SDS-PAGE gel following various treatments.

The overall process of producing the PICs involved several reaction and purification steps. The structural integrity of the antibody was investigated at all stages of the conjugation procedure (FIG. 5). Treatment of C225 with 50% DMSO did not affect the antibody's structural integrity in any way (Lane 2). PEGylation essentially resulted in splitting of the single major protein band of the original unmodified antibody into a ladder of 3 major PIC protein bands of roughly equal or higher molecular weight (Lane 3). Unmodified antibody has an estimated molecular weight of 170 kDa and the major PIC protein bands have apparent molecular weights of 179 kDa, 198 kDa, and 218 kDa (FIG. 5). The apparent spacing of the PIC protein bands is roughly 20 kDa, whereas the molecular weight of the two-branched PEG is known to be 10 kDa. This indicates that the migration characteristic of PEGylated antibody on SDS-PAGE gels is somewhat different than that of unPEGylated globular protein standards. The major PIC protein bands most likely correspond to 0, 1, and 2 PEG moieties per PIC molecule. It is noteworthy that a significant fraction of the species present in the PIC preparations consisted of unPEGylated PIC, and yet the PIC preparations as a whole remained soluble in purely aqueous solutions. More highly PEGylated PICs and other heavy molecular weight aggregates were present in the PIC preparations as minor species (FIG. 5B).

Previous photosensitizer conjugate studies utilized unpurified active ester preparations or active ester preparations of unspecified purity (Hamblin et al., 1996), (Mew et al., 1983), (Levy et al., 1989), (Jiang et al., 1990), 19, (Jiang et al., 1991), (Jiang, 1992), (Mew et al., 1985), (Steele, 1988), (Gross and Brandis, 1997), (Hamblin et al., 2000b) in the conjugation reactions. The effects of treating antibody either with a mixture of EDC and NHS or with unpurified crude BPD-NHS active ester were examined and compared with PICs prepared from purified BPD-NHS active ester (Lanes 4-7). Treatment of the antibody with EDC and NHS was performed in the same manner as treatment of the antibody with unpurified crude BPD-NHS active ester, except no BPD was added to the mixture of EDC and NHS. Treatment of the antibody with unpurified crude BPD-NHS active ester was performed in the same manner as treatment of the antibody with purified BPD-NHS active ester, except no efforts were made to purify the crude active ester product. The reaction of the antibody with EDC and NHS yielded a fraction of intermolecularly crosslinked antibody aggregates (Lane 4). Moreover, the non-intermolecularly crosslinked fraction of the antibody that was treated with the EDC/NHS mixture appeared to migrate slightly faster than untreated antibody, and the protein bands were somewhat streaked. These effects appear to be indications of intramolecular antibody crosslinks, which can be expected given that antibodies contain large numbers of lysines in close proximity to glutamic and aspartic acid residues. PEGylation of the antibody prior to treatment with the EDC/NHS mixture greatly suppressed intermolecular crosslinks (Lane 5). PICs prepared from unpurified BPD-NHS exhibited a similar migration pattern to PEGylated antibody treated with the EDC/NHS mixture (Lane7). A significant amount free BPD was present at the bottom of Lane 7. Thus, PICs prepared from unpurified BPD-NHS could not be thoroughly purified even after gel filtration in 50% DMSO. In contrast, PICs prepared from purified BPD-NHS contained significantly less free photosensitizer impurity, and the protein bands were not streaked or downshifted (Lane 6). Purification of the BPD-NHS active ester was helpful for preventing undesirable crosslinking reactions and obtaining high purity PIC preparations containing less than about 10% non-covalently-associated free photosensitizer impurity, especially when high BPD:antibody molar ratios were desired.

Photophysical Characterization of the PICs

In order to assess how conjugation to the antibody affected the ability of BPD to generate phototoxic species, relative fluorescence quantum yields and fluorescence decay signals for free BPD and for the various BPD PIC preparations were measured. Although fluorescence is a photophysical property of the singlet excited state of a photosensitizer, fluorescence quantum yields and decay times generally correlate with a photosensitizer's ability to generate phototoxic species. This correlation stems from the fact that a photosensitizer's phototoxic quantum yield usually correlates with its triplet quantum yield. In turn, a photosensitizer's triplet quantum yield is directly proportional to its singlet excited state lifetime (Savellano, 2000).

Fluorescence properties were measured in 50% DMSO/50% aqueous solutions in order to overcome the tendency of BPD to aggregate in a purely aqueous solution. Relative fluorescence quantum yields for free BPD and for various PIC samples with varying BPD:antibody molar loading ratios were calculated from the ratios of the slopes of fluorescence emission intensity versus absorbance plots. The fluorescence emission intensity versus absorbance plot for a given sample was generated by measuring the emission intensities of a series of dilute solutions prepared from a concentrated stock solution of the sample. Typically 4 to 5 different dilutions of a given sample were prepared in 50% DMSO/50% aqueous solutions with absorbances ranging from 0 to ~0.1 $cm^{-1}$ at the excitation wavelength, 428 nm, which is centered near the absorbance peak maximum of the Soret band of BPD. Fluorescence emission intensity was measured as the area under the fluorescence emission peak in the 650 to 800 nm range. Steady-state fluorescence spectra were acquired using a Spex FluoroMax spectrofluorometer (Spex Industries, Inc., Edison, N.J.). Fluorescence decay signals of free BPD and of various PIC preparations with varying BPD:antibody molar loading ratios were measured using a TimeMaster fluorescence lifetime spectrometer, operated in its StrobeMaster stroboscopic mode (Photon Technology International, Inc., Monmouth Junction, N.J.). The StrobeMaster stroboscopic system is based on a technique described by Bennett (TimeMaster fluorescence lifetime spectrometer reference manual, 1994). The excitation source was a $N_2$ (30%)/He nanosecond lamp. Samples were prepared in 50% DMSO/50% aqueous solutions and were adjusted by dilution to approximately 0.4 $cm^1$ at ~690 nm in order to ensure that all solutions contained roughly equal amounts of BPD content. Before recording fluorescence decay signals, a $BaSO_4$ scattering solution was used to measure the nanosecond lamp temporal profile, i.e., the instrument response function (IRF). The experimental fluorescence decays were then acquired with the emission monochromator set at 700 nm. Because sample solutions were excited with the full $N_2$ (30%)/He lamp spectrum (~300-400 nm), a longpass filter (>579 nm) was placed in front of the emission monochromator to eliminate second order grating effects. The IRF was then used to fit the experimental fluorescence decay signals by an iterative reconvolution procedure, assuming either a monoexponential or a biexponential free fluorescence decay. The fitting procedure was based on the Marquardt algorithm (TimeMaster Pro software user's manual, 1998),(Bevington, 1969).

Measurement of fluorescent properties in 50% DMSO/50% aqueous solutions allowed an investigation of the quenching effects that occur due to covalent anchorage of BPD onto the antibody, as opposed to quenching effects that occur due to noncovalent interactions of BPD. Previous PIC investigations examined the photophysical and photochemical properties of the conjugates in predominantly aqueous solutions, and, therefore, did not distinguish between these two types of quenching effects (Savellano, 2000). It is important or useful to distinguish between these two effects given that in an in vivo setting noncovalent interactions of the photosensitizer are most likely disrupted via interactions with serum proteins, whereas covalent linkage of the photosensitizer onto the antibody cannot be disrupted except by hydrolytic and/or enzymatic processes (e.g. during lysosomal degradation).

Figure 6:
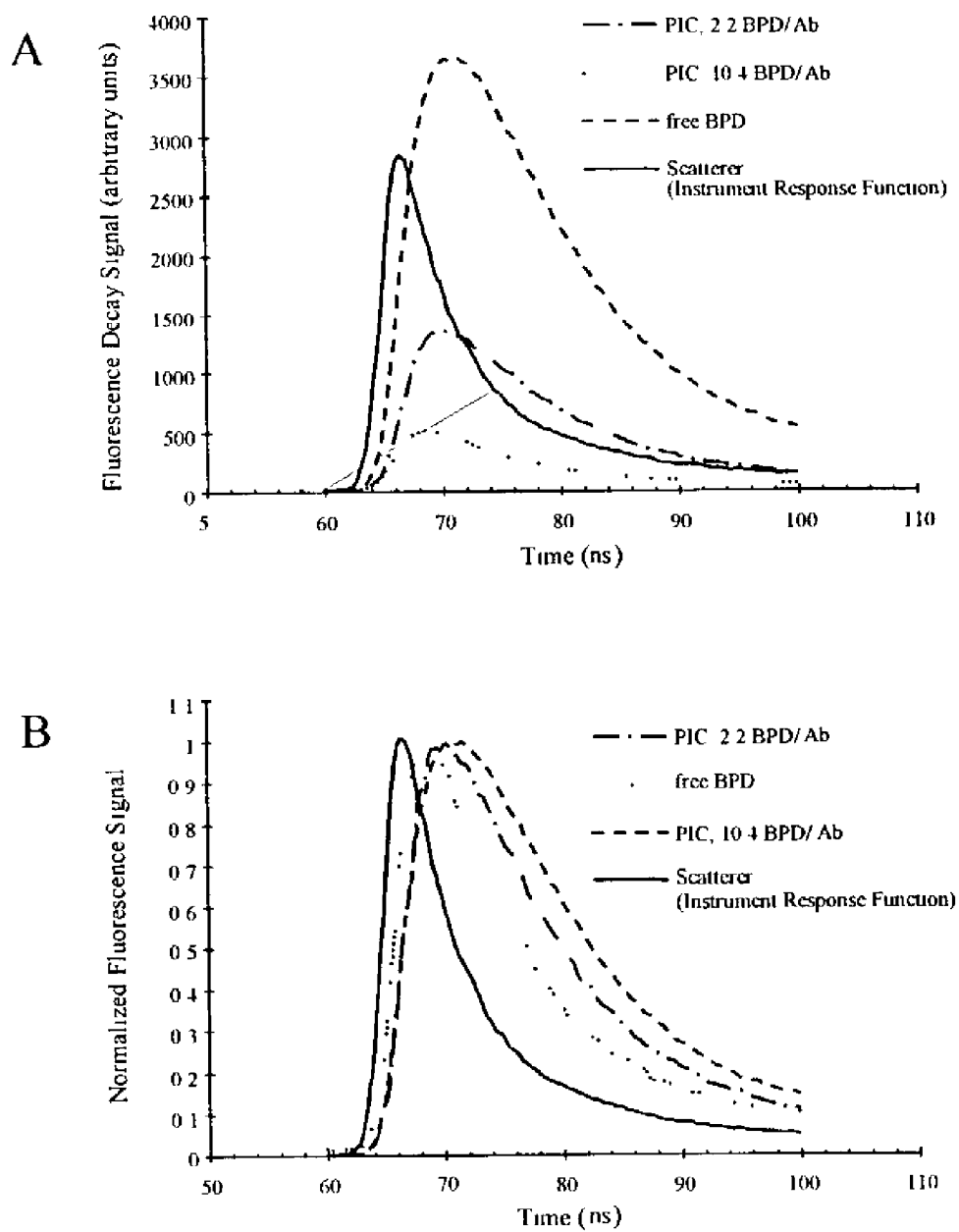
FIG. 6 depicts unnormalized and normalized fluorescence decays that are representative of various PICs and of free BPD.

Unnormalized and normalized fluorescence decays that are representative of the various PICs and of free BPD are shown in FIGS. 6A and 6B. The intensities of the fluorescence decay signals for the PICs were significantly reduced compared to that of free BPD. Moreover, the intensities of the fluorescence decay signals for the PICs decreased as the BPD:Ab molar loading ratios of the PICs was increased (FIG. 6A). The fluorescence decay signals for the PICs were also significantly shorter-lived than that of free BPD, and the fluorescence decay lifetimes for the PICs decreased as the BPD:Ab molar loading ratios of the PICs was increased (FIG. 6B). The fluorescence decay signal of free BPD was best fit by a monoexponential, and the fluorescence decay signals of the PICs were best fit by biexponentials. The weighted-average fluorescence decay lifetimes for free BPD and for PICs with BPD:Ab molar loading ratios of 2.2, 4.4, 7.2, and 10.4 were 6.02 ns, 2.98 ns, 2.10 ns, 1.42 ns, and 1.38 ns, respectively. The relative fluorescence quantum yields for free BPD and for PICs with BPD:Ab molar loading ratios of 2.2, 4.4, 7.2, and 10.4 were 1.00, 0.314, 0.204, 0.152, and 0.111. Thus, it can be seen that relative fluorescence quantum yields correlate well with weighted-average fluorescence decay lifetimes. These observations demonstrate that covalent conjugation of BPD to an antibody effectively results in a substantial static concentration quenching effect.

Absorbance and fluorescence measurements indicated that the intact PIC's photochemistry is quenched compared to free BPD as a result of the dense packing of the photosensitizer onto the targeting moiety. This advantageously allows the PIC to remain quenched while freely distributed in the blood stream. Once the PIC reaches the lysosomal compartment and the degradation process begins, photoactivation can occur without activating the quenched compositions present in the blood stream. Activation of the inventive PICs can therefore be selectively activated within the cells of interest, resulting in enhanced safety for patients undergoing photodynamic therapy.

Example 2

In Vitro Analysis of PICs

Cellular Uptake of PICs

Cellular uptake studies were conducted to evaluate targeting specificity of the PICs. Cells were plated in 2 ml of media in 35 mm tissue culture dishes at densities such that the cells reached ~90% confluence at the end of a three-day growth period. Following an initial period of at least 14 to 20 hours, which allowed for cells to attach and begin dividing, incubation with PICs or free BPD was initiated by replacing the original 2 ml of media with 2 to 4 ml of media containing PIC or free BPD. From this point onward, cells were handled under low light conditions to avoid photosensitizing the cells or photobleaching the photosensitizer. Incubations were done at 37° C. and were begun with respect to the end of the three-day growth period. At the end of the three-day growth period, the media containing PIC or free BPD was removed, and cells were washed twice with 2 ml of PBS. Cell samples were then collected and analyzed. Cells were lifted off culture dishes using either trypsin or a scraper, and 1 ml cell suspensions in culture medium (without any fetal bovine serum) were prepared from each dish. 0.4 ml of each 1 ml cell suspension was solubilized in 2 ml of 1 M NaOH/1% SDS in a disposable fluorimeter cuvette. In order to quantitate the BPD content of the cell suspensions, the fluorescence emission intensities of the solubilized cell suspensions were compared to those of free BPD standards. Fluorescence measurements were performed as previously described. The remaining 0.6 ml of each cell suspension was used to do a cell count using a hemacytometer and to assay for cell protein content by a Bradford-type protein assay. Alternatively, cells were removed from culture dishes by incubating the cells with 100 µl of lysis buffer (5 mM EDTA, 10 mM Tris, 150 mM NaCl, 1% Triton X-100) per dish at 37° C. for 5 to 10 minutes, followed by the addition of 900 µl of de-ionized/distilled $H_2O$ per dish. Any remaining adherent cellular debris was scraped off and pipetted a few times to ensure thorough solubilization of cellular material. This yielded a 1 ml solubilized cell sample from each dish. 0.5 ml of each solubilized cell sample was mixed with 2 ml of 1 M NaOH/1% SDS in a disposable fluorimeter cuvette to measure BPD content via fluorescence quantitation. The remaining 0.5 ml of each solubilized cell sample was used to do a protein assay. To relate protein content to the number of cells, sets of control cell dishes that had not been treated with PIC or free BPD were prepared solely to estimate the conversion parameter, number of cells per mg of cell protein. The value of this parameter, which varied for the different cell lines, was measured in the following manner. First, 1 ml cell suspensions in culture medium, prepared from one set of control cell dishes, were counted using a hemacytometer. Second, 1 ml solubilized cell samples in lysis buffer, prepared from a corresponding set of control cell dishes, were assayed for protein content.

Figure 7:
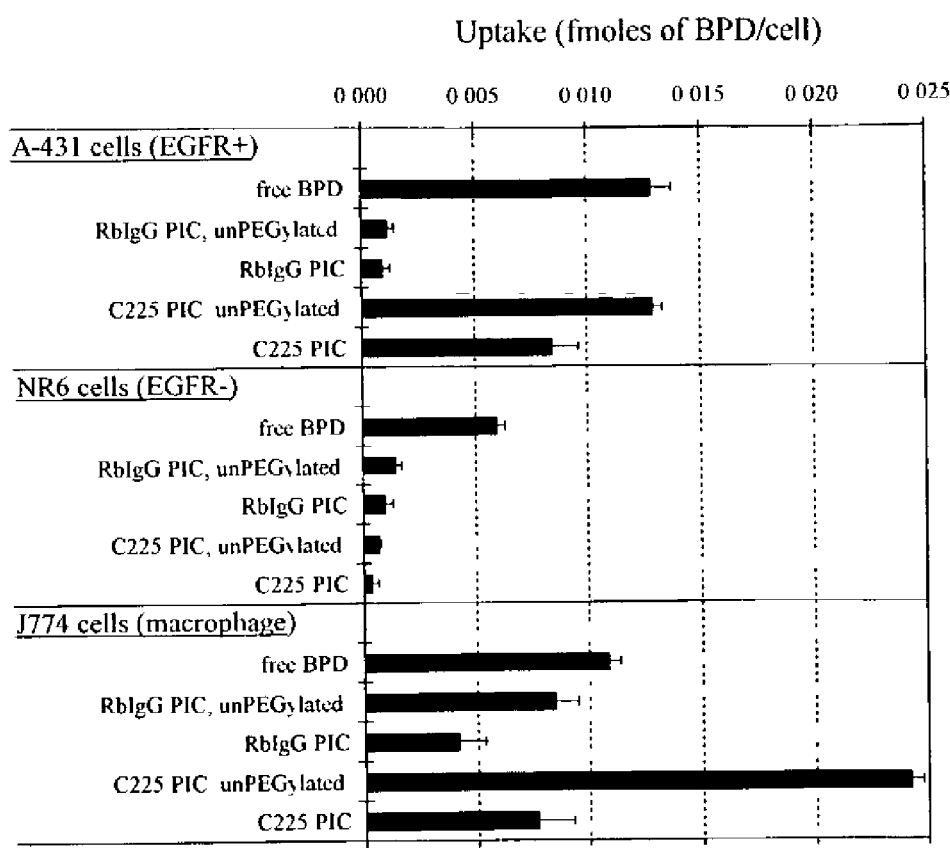
FIG. 7 depicts cellular uptake studies.

For preliminary cellular uptake studies as shown in FIG. 7, the PICs were still prepared using unpurified crude BPD-NHS. This necessitated that the loading of the PICs be limited to a relatively low labeling ratio of 4 BPD per antibody in order to produce PICs of acceptable purity (i.e., less than 10% noncovalently-associated free photosensitizer impurity). Moreover, some of the PIC samples were not PEGylated, in order to observe the different cellular uptake properties of PEGylated and unPEGylated PICs. In fact, PEGylation significantly reduced nonspecific J774 macrophage uptake of the PICs by a factor of approximately 2 to 3 (FIG. 7). This effect is most likely due to the fact that PEGylation dramatically reduced aggregation of the PIC preparations. In addition, the C225 PICs were capable of specifically targeting EGFR-overexpressing cells in the intended manner. The C225 PICs (anti-EGFR) were taken up by the EGFR-overexpressing A-431 cells, but not by the EGFR-negative NR6 cells. Likewise, nonspecific RbIgG PICs were not taken up by either the A-431 cells or by the NR6 cells to any significant extent.

Phototoxicity and Competition Studies

Preliminary phototoxicity studies were conducted using EGFR-overexpressing A-431 cells. An antibody:PEG-NHS molar ratio of approximately 2 was used to prepare the PICs, which allowed the PICs to be transferred to purely aqueous buffer without forming insoluble aggregates. In contrast to the preliminary uptake studies, the PICs were prepared using purified BPD-NHS, which advantageously permitted higher BPD:Ab molar loading ratios (roughly 7 BPD:Ab) without sacrificing PIC purity. However, in delivering as much photosensitizer as possible per PIC carrier, it should be noted that undesirable quenching effects can occur. For example, it is not possible to achieve relatively high BPD:Ab molar loading ratios without appreciably quenching the photophysics and, presumably, the photochemistry of the PICs. This is because photosensitizer molecules must necessarily pack closer to each other on the antibody as the BPD:Ab molar loading ratio of the PIC is increased. Consequently, in order to overcome quenching effects of the PICs, a proper target must be chosen. The EGFR is one such target, given that it is overexpressed by many types of tumor cells, and binding of PICs to the EGFR eventually delivers the PICs to the lysosomal compartment where they are degraded, thereby releasing the photosensitizer in a more photoactive form.

Cells were plated in 2 ml of media in 35 mm tissue culture dishes at densities such that the cells reached approximately 60 to 80% confluence at the end of a three-day growth period. Following an initial period of at least 14 to 20 hours, which allowed for cells to attach and begin dividing, incubation with PICs or free BPD was initiated by replacing the original 2 ml of media with 2 to 4 ml of medium containing PIC or free BPD. Incubations were done at 37° C. and were begun with respect to the end of the three-day growth period. At the end of the three-day growth period, the medium containing PIC or free BPD was removed. Cells were washed once with 2 ml of DPBS, and 2 ml of fresh medium was added back to each dish. Cells were then immediately irradiated with the requisite light dose. Following irradiation, cells were incubated overnight at 37° C. and then assayed for viability by the calorimetric MTT assay (Mosmann, 1983). Except for the intended light dose, care was taken to protect the cells from light exposure at all times.

The radiation source was a dye laser pumped by an argon ion laser (models CR-599 and Innova 100, respectively, Coherent Inc., Palo Alto, Calif.). The laser dye was DCM (4-diacyanomethylene-2-methyl-9p-dimethylaminostyryl-4h-pyran), and the dye laser emission was tuned to 690 nm. Alternatively, a 687 nm laser diode (model SDL 7432, SDL Inc., San Jose, Calif.) was used as the radiation source. In order to achieve homogeneous irradiation of the cells, a fiber and a set of lenses were utilized to project the laser light uniformly across and up through the bottom of each culture dish.

Although the preliminary cellular uptake measurements revealed that total BPD uptake using the C225 PIC was comparable to that achieved using the free photosensitizer after a 14 hour incubation period (FIG. 7), initial phototoxicity experiments showed that high levels of cell killing could not be achieved with the C225 PIC unless the incubation period was prolonged significantly beyond 14 hours. Cellular internalization results in an enhanced photodynamic effect, which can be attributed to dequenching of the PIC through, for example, lysosomal degradation. In contrast, phototoxic cell killing with the free photosensitizer was greater than 90% even for incubation periods much shorter than 6 hours. Therefore, a 40-hour incubation period was utilized for subsequent A-431 cell killing experiments.

Binding of the C225 PICs to the EGFR was competed with varying amounts of the unmodified C225 antibody. Competition experiments were conducted using saturating amounts of C225 PIC co-incubated with equal or greater amounts of unmodified antibody. Typically, the unmodified antibody concentration was varied from 1 to 4 times the concentration of the C225 PIC.

Figure 8:
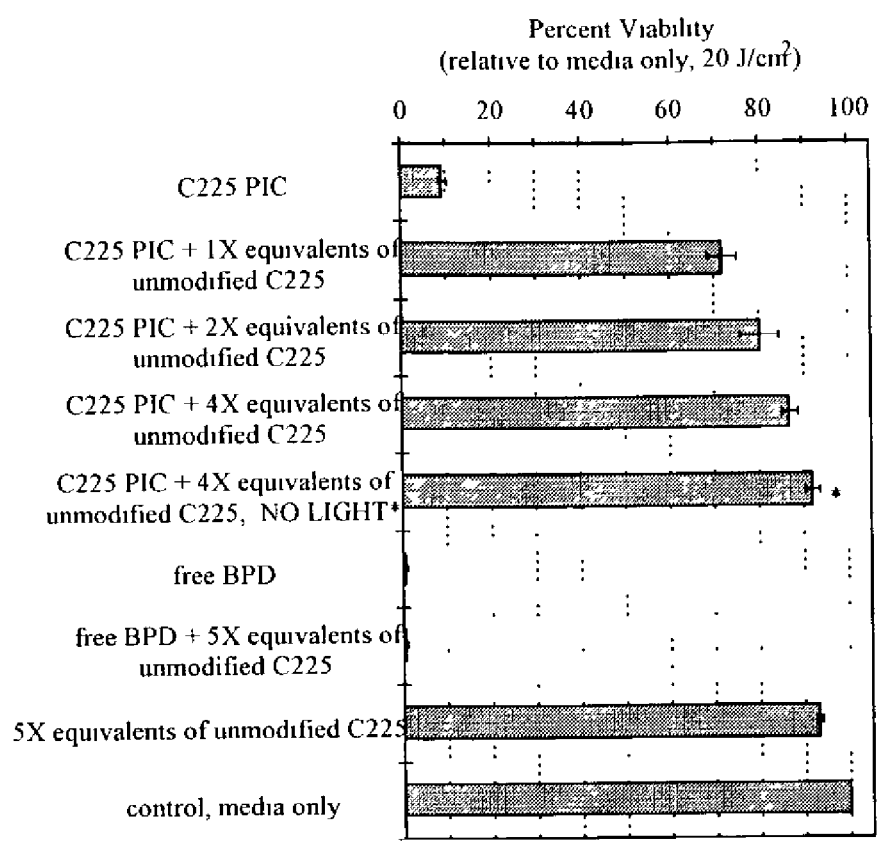
FIG. 8 depicts effective competition of C225 PIC phototoxic effects by co-incubation with unmodified C225 antibody.

A 90% reduction in viability was achieved with the C225 PIC using a light dose of 20 J/Cm.sup.2 (FIG. 8). The phototoxic effects of the PIC were effectively competed by co-incubation with unmodified C225 antibody (FIG. 8). The fact that competition with unmodified C225 antibody reduced the phototoxic effects of the PIC indicates that the PIC's activity is predominantly mediated by its specific binding to the EGFR. Cells treated with unmodified C225 antibody alone exhibited a slight reduction in viability. Similarly, cells treated with the C225 PIC and co-incubated with unmodified C225 antibody but not exposed to light also exhibited a slight reduction in viability. These observations appear to be in agreement with previous results that show that the unmodified C225 antibody by itself possesses growth inhibitory effects (Goldstein et al., 1995). This report compares the biological effects of 225 and its chimeric counterpart, (designated C225) against established A431 tumor xenografts in nude mice. The results of these experiments indicated that C225 was more effective than 225 in inhibiting tumor growth in this model. In addition, many of the animals treated with C225 were tumor free at the end of each treatment protocol. It was determined that the dissociation constant of C225 was about 5- fold lower than 225. This suggested that the increased capacity of C225 to compete with ligand for binding to the EGFR was responsible for its enhanced in vivo antitumor effect. Both 225 and C225 were able to block EGF-induced phosphoryfation of the EGER in A431 cells (Goldstein et al., 1995). In addition, it is important or useful to note that phototoxic cell killing either with free BPD or with free BPD mixed with unmodified C225 resulted in greater than 99% reduction in viability, which was significantly greater killing than that achieved with the C225 PIC. Conjugation of BPO to C225 antibody undoubtedly modifies its cellular uptake kinetics, subcellular localization characteristics, and photophysical properties.

Example 3

In vivo Analysis of Combination EGFR and BPD Verteporfin Therapy

The monoclonal antibody component of a PIC, such as C225, can possess tumoricidal properties that are independent of the photosensitizer compound to which the antibody is linked. The combined therapeutic use of a tumoricidal antibody and a photosensitizer compound defines what is referred to herein as photodynamic combination therapy or "combination therapy." Combination therapies, which would include some PICs, advantageously co-localize activated photosensitizer compounds and tumoricidal antibodies in tumor tissue. Employing a dual mechanism of action against tumor growth and/or formation can increase therapeutic efficacy of the treatment regime.

The effects of combination therapy on tumor inhibition were evaluated in xenograft animal models of intra-peritoneal epithelial ovarian carcinoma. Results obtained in this model system are reasonably predictive of treatment efficacy for the human condition. The following groups were analyzed:

Group 1: No Treatment
Group 2: BPD
Group 3: Light
Group 4: BPD and light (PDT)
Group 5: C225
Group 6: C225 and BPD
Group 7: C225 and light
Group 8: C225, BPD and light (combination)

In addition, combination therapy (group 8) resulted in a significantly increased reduction of tumor burden in comparison to the use of either PDT (group 4) or C225 (group 5) alone.

In humans, recurrent ovarian carcinoma is rarely curable. The success for improving survival rests on early detection and development of more effective treatment modalities. In advanced stages, ovarian cancer is most frequently limited to the peritoneal cavity. Results presented herein indicate that anti-cancer treatments directed to the peritoneal cavity can be successfully approached via minimally invasive, local therapies, such as combination therapies.

Animal Model Studies of Intraperitoneal Combination Therapy

To test the effect of the combination treatment in vivo, a known animal model system was utilized (Molpus et al., 1996a). As discussed above, the xenograft model of intra-peritoneal epithelial ovarian carcinoma has been noted to be desirable for measurement of the effects of PDT (Molpus et al., 1996a). This model manifests tumor derived from human ovarian carcinoma cells with all of the inherent biological properties of human disease. As has been previously described, the model is characterized, as in human patients, by diffuse solid tumor, ascites, parenchymal invasion, lymph-vascular space invasion, and neovascularization (Molpus et al., 1996a). Briefly, athymic Swiss female nude mice, weighing 20-25 grams (6-8 weeks old) were injected intraperitoneally, using a 27-gauge needle, with $31.5 \times 10^6$ NIH:OVCAR-5 cells, suspended in 2 ml PBS. NIH:OVCAR-5 cells were obtained from the Fox Chase Cancer Institute (Philadelphia, Pa.). Cells were grown in RPMI-1640 media (Mediatech Inc, Herndon, Va.) supplemented with 10% heat-inactivated fetal calf serum (GIBCO Life Technologies, Grand Island, N.Y.), and 100 U/ml penicillin and 100 µg/ml streptomycin. The cells were maintained in an incubator at 37° C. in an atmosphere of 5% $CO_2$. At the time of NIH: OVCAR-5 cell injection, mice were given a numeric ear tag. Animals were anesthetized before the cell injection with 0.03 ml of a ketamine/xylazine mixture (ketamine, 120 mg/kg; xylazine, 15 mg/kg).

The mice were maintained in accordance with the guidelines established by the Massachusetts General Hospital Subcommittee on Research Animal Care. They had continual access to food and water, taken ad libitum. Animals were housed in laminar flow racks, under specific pathogen-free conditions. Sacrifices were performed by $CO_2$ inhalation.

Intraperitoneal PDT

Intraperitoneal ("i.p.") PDT in the nude mice was performed as previously described (Molpus et al., 1996a). On day 10 and 20 after tumor cell injection, mice in BPD treatment and/or control groups 2, 4, 6, and 8 were injected with 0.25 mg/kg body weight of liposomal BPD-MA i.p. 90 minutes prior to light exposure. Light was not administered to animals in groups 1, 2, 5, and 6. BPD-MA solutions were prepared immediately prior to use in sterile PBS (total of 1 ml). All work involving BPD-MA was performed in subdued lighting.

Light Treatment

Animals which had to be illuminated were injected with 2 mL of a 0.1% intralipid solution i.p. prior to illumination to enhance light scattering. Animals were anesthetized with 0.03 ml of a ketamine/xylazine mixture (ketamine, 35 mg/ml; xylazine, 5 mg/ml). A solid state diode laser was used for illumination (BWF 690-1, B&W TEK, Newark, Del.), which delivers monochromatic light (690+/-5 nm) to overlap closely the absorption maximum of BPD-MA (690 nm), at a maximum power from the diode of 1 W. Alternatively, an argon-pumped dye laser (Coherent) was used to deliver 690 nm light i.p. via a cylindrically diffusing fiberoptic tip (8.0 mm×0.4 mm). The fiber, connected to the Argon-pumped dye laser or the solid state diode laser was introduced into the peritoneal cavity of a supine anesthetized animal via a centrally placed 22-gauge catheter traversing the abdominal cavity. A total of 20 J of light was delivered, at a fluence rate of 100-200 mw/cm$^2$. Of the total light energy, one fourth (5 J) was delivered to each i.p. quadrant over equivalent time periods. At the completion of the treatment, the mice were allowed to recover in an animal warmer until they awoke and resumed normal activity.

C225 Treatment

On day 11, mice in groups 5, 6, 7, and 8 were given a dose of 0.5 mg C225 i.p in 0.25 ml. This dose was repeated on days 14, 17, and 19 (total of 2.0 mg C225/animal).

Control Groups

Mice were treated with PDT, C225 alone or the combination of the two treatments. Control groups 1, 2, 3, 6, and 7 included mice which received no treatment, only BPD, only light, C225 and BPD, or C225 and light, respectively. Therapeutic groups 4 and 5 were utilized as controls for analysis of the increased therapeutic effects of combination therapy.

Tumoricidal Response

Two endpoints were studied. The first endpoint studied was short-term tumor weight. The second endpoint studied was long-term survival. In the short-term tumor weight studies, animals were sacrificed on day 21 to assess acute treatment effects. Animals were also carefully examined for the presence of distinct extra-abdominal metastasis. Representative tissue samples were examined pathologically via hematoxylin and eosin staining.

Animals were weighed before tumor cell injection, and before sacrifice at day 21. All animals lost weight in the three-week course after tumor cell injection. The weight losses among treatment and/or control groups are summarized in Table 1. The control group and the group treated with light only had the highest weight loss. There was no evidence of statistically significant weight loss in the combination treatment group (group 8), as compared to the control animals. These animals appeared to be relatively free of PDT-associated therapeutic toxicity.

TABLE 1

| Group Number | Weight Loss In Grams |
|---|---|
| 1. No treatment | 2.66 |
| 2. BPD | 2.01 |
| 3. Light | 2.63 |
| 4. BPD and light (PDT) | 2.14 |
| 5. C225 | 2.11 |
| 6. C225 and BPD | 1.96* |
| 7. C225 and light | 1.75* |
| 8. C225, BPD and light | 2.09 |

*$p < 0.05$ in comparison to the no treatment group

Tumoricidal response was assessed by comparing the extent of gross residual disease in treated animals to the extent of disease in untreated controls. Using the distribution pattern of the tumor in the OVCAR-5 human xenograft mouse model, which 20 was previously described (Molpus et al., 1996b), the sites where tumor was consistently present were dissected.

Table 2 depicts the anatomical distribution of tumor burden in control mice, after correcting for the normal tissue weight of each organ. At necropsy (21 days after inoculation with OVCAR-5 cells) all macroscopic disease was systematically resected and the tissue was systematically weighed from the following areas: subgastric omentum (SGO), pelvic omentum bilaterally (PO), the pelvis (P), including ovaries, fallopian tubes and uterus, bowel mesentery (M), and the diaphragm (D). The wet weights of these tissues were determined and the total weight calculated. In the presence of tumor involvement, it became difficult to distinguish non-involved tissue from areas completely encased by metastatic disease. In order to address this issue, the weight of all of these organs in normal, non-injected mice (average 660 mg+/-63) was subtracted from the weights of mice injected with OVCAR-5 cells.

TABLE 2

| Tumor Burden | SGO | PO | P | M | D |
|---|---|---|---|---|---|
| Average (mg) | 119 | 145 | 301 | 126 | 64 |
| Standard Deviation | 68 | 35 | 89 | 46 | 14 |

All groups were statistically different from control ($p<0.0001$) except for group 3, which was treated with light only. The group treated with the combination therapy had statistically significant ($p<0.0001$) less tumor burden than all other groups.

Figure 9:
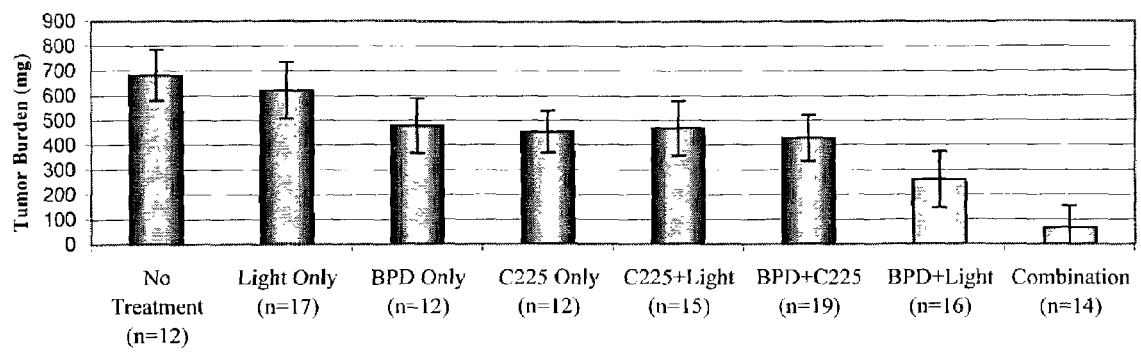
FIG. 9 depicts the average weight of residual carcinoma at the time of necropsy in mice of groups 1 through 8.

To determine the tumor burden (Table 3), we resected organs from nine animals that were not inoculated with tumor and used the average weight to adjust for tumor versus normal organ weight. FIG. 9 and Table 3 show that the PDT and combination therapy reduced tumor burden to 38% and 10%, respectively, of the no treatment control group.

TABLE 3

| Group Number | Tumor Burden (mg) | Survival Fraction | lnSF |
|---|---|---|---|
| 1. No treatment | 683 | 1.00 | 0 |
| 2. BPD | 469 | 0.69 | −0.408397662 |
| 3. Light | 622 | 0.91 | −0.093554767 |
| 4. BPD and light | 261 | 0.38 | −0.961974452 |
| 5. C225 | 454 | 0.66 | −0.408397662 |
| 6. C225 and BPD | 429 | 0.63 | −0.465037941 |
| 7. C225 and light | 478 | 0.70 | −0.356884127 |
| 8. C225, BPD and light | 67 | 0.10 | −2.32180224 |

Notably, for mice treated with combination therapy, the average weight of residual carcinoma at the time of necropsy was 67 mg, as compared to 683 mg in no treatment controls (FIG. 9). This indicates that there was a dramatic, 10-fold decrease in the total tumor burden between the no treatment control and the combination treatment groups. The reduction in overall disease burden collectively reflects the significant decrease in tumor noted at all anatomic sites. In addition, combination therapy (group 8) resulted in a significantly increased reduction of tumor burden in comparison to use of either PDT (group 4) or C225 (group 5) alone.

The method employed for statistical analysis of tumor burden was the Steel-Peckham method. The ln of the survival fraction (lnSF) was calculated (Table 3), and the following formula is used to determine interactive effects between the therapies: $DL=-(lnSF_{XY}-lnSF_X-lnSF_Y)$. If $DL>0$, the interaction is synergistic; if $DL=0$, there is no interaction; and, if $DL<0$, the interaction is antagonistic. Results from various treatment combinations are summarized in Table 4.

TABLE 4

| Formula | DL | Effect |
|---|---|---|
| $-(lnSF_{combo} - lnSF_{PDT} - lnSF_{Ab})$ | 0.95143 | synergistic |
| $-(lnSF_{PDT} - lnSF_{BPD} - lnSF_{hv})$ | 0.493 | synergistic |
| $-(lnSF_{Ab+hv} - lnSF_{Ab} - lnSF_{hv})$ | −0.145 | antagonistic |
| $-(lnSF_{Ab+BPD} - lnSF_{Ab} - lnSF_{BPD})$ | −0.319 | antagonistic |

Combination PDT and C225 based immunotherapy resulted in the highest value (0.95143), indicating that combination therapy produces a synergistic effect when compared to the individual components.

Figure 10:
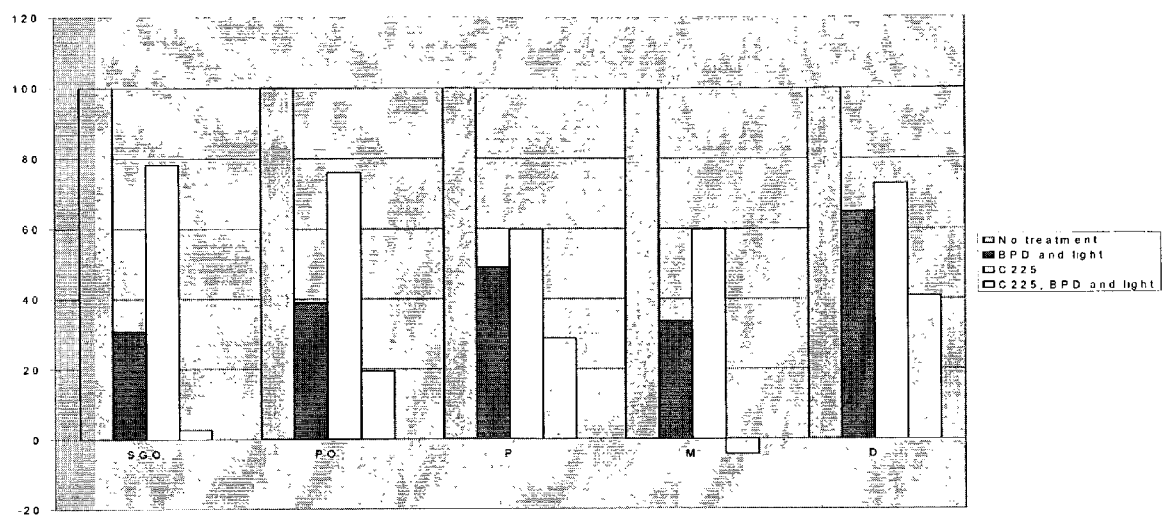
FIG. 10 depicts the site-specific decrease in tumor weight in the subgastric omentum, pelvic omentum bilaterally, the pelvis, including ovaries, fallopian tubes and uterus, bowel mesentery, and the diaphragm of mice in groups 1, 4, 5, and 8.

FIG. 10 depicts the decrease in tumor weight in subgastric omentum, pelvic omentum bilaterally, the pelvis, including ovaries, fallopian tubes and uterus, bowel mesentery, and the diaphragm. The groups treated with and without C225 were combined for analysis, (i.e. BPD+light vs. BPD+light+C225; light vs. light+C225). The bowel mesentery and subgastric omentum had a significantly larger decrease in tumor weight loss than the pelvis (p<0.05) in both groups treated with BPD and light. The reduction in tumor burden noted in the pelvis for the PDT and combination treatment groups was less remarkable than the decrease noted in the mesentery and pelvic omentum in these animals. This result may be attributable to inadequate exposure to direct illumination.

In the groups treated with PDT or combination therapy, the bowel mesentery surprisingly showed a statistically significant reduction in tumor burden. Others studies have failed to achieve encouraging results in the bowel mesentery. Arguably, less tumor reduction is expected after PDT in this area, given direct light shielding, the extensive length of the bowel, and its numerous folds and layers within the peritoneal cavity (Molpus et al., 1996a). The results herein may be due, in part, to improved light delivery. The reduction of tumor volume in the bowel mesentery was the most dramatic in the combination treatment group. This indicates that there can be potentiating effects of C225 in PDT-treated bowel.

Long Term Survival

The second endpoint studied was long term survival. A different group of animals was utilized to investigate survivability. Animals with rapid tumor progression leading to uncontrollable ascites or systemic illness were sacrificed. Animals were sacrificed based on the following parameters: loss of more than 15% body weight, severe pain not relieved by analgesics, self-mutilating behavior, inability or unwillingness to eat or drink, and weight gain of more than 20% body weight. At the time of necropsy, samples were weighed and collected as previously described.

Figure 11:
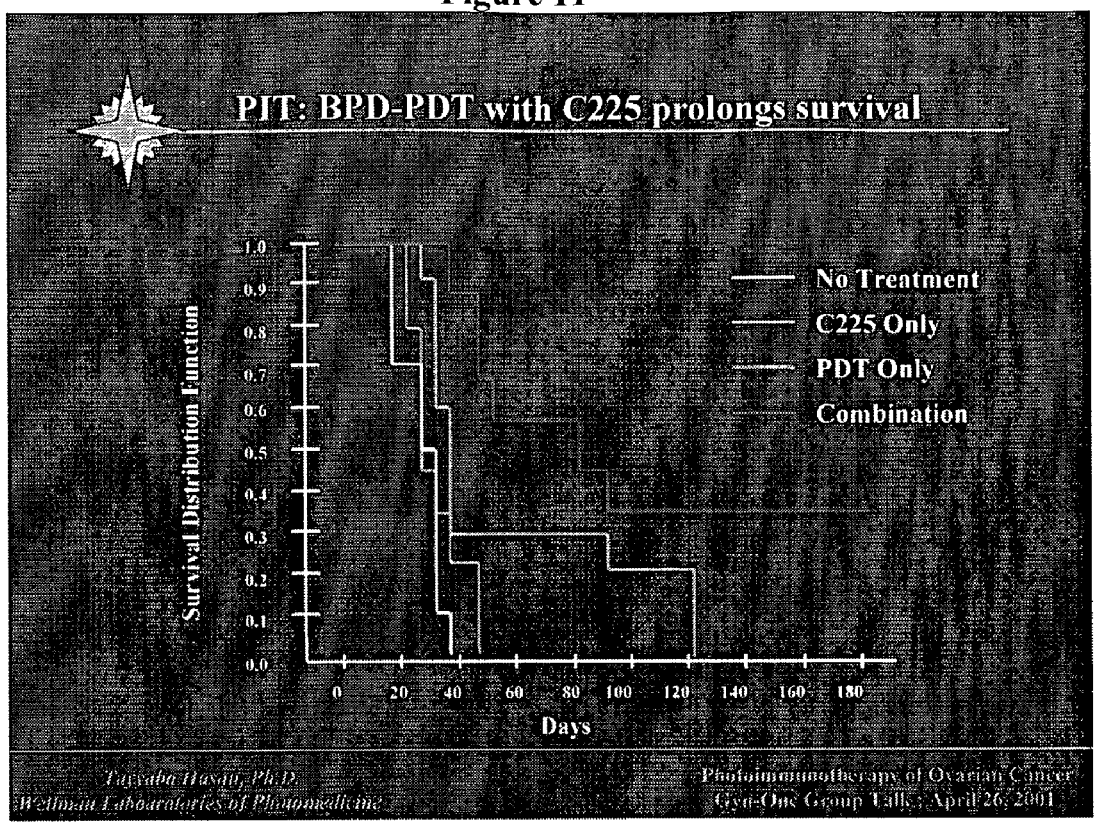
FIG. 11 depicts the Kaplan-Meier curve.

Mice were either untreated (group1), treated with PDT alone (group 4), C225 alone (group 5), or with the combination of C225 and PDT (group 8), as described above. The Kaplan-Meier curve is depicted in FIG. 11. After 6 months (180 days) 3 out of 9 (33%) mice treated with combination therapy were still alive, while 1 mouse out of 9 (10%) treated with PDT alone was still alive. These mice were sacrificed at this time-point. The absence of gross tumor burden was noted in three cases. In one mouse, treated with PDT alone, there was tumor in the internal organs. The days on which 50% of the mice have died per group are tabulated in Table 5.

TABLE 5

| Group Number | 50% alive |
|---|---|
| 1. Control | 28 (CI 21-35) |
| 4. BPD + light (PDT) | 36 (CI 32-90) |
| 5. C225 alone | 26 (CI 25-37) |
| 8. Combination treatment | 80 (CI 47-180) |

Comparison of survival curves indicated that there was no statistical significance between the survival rates of untreated mice or the mice receiving C225 alone (group 5). However, groups receiving either PDT or combination therapy had significantly longer survival rates than control animals. The difference between PDT and combination therapy was significant (P=0.052 in Log-rank test). Thus, there was a significant increase in the survival advantage of mice receiving combination therapy.

Results from the long-term survival studies indicated that there were no deaths or significant co-morbidities secondary to treatment. This result can be attributable to several factors, including the ability to reduce the number of PDT treatments for achieving a significant acute tumoricidal response. Reducing the number of PDT treatments advantageously reduces the exposure of the animals to anesthesia. This is of special clinical relevance since the translation of this treatment to the clinical arena would necessitate a scenario feasible in terms of the patient's exposure to anesthesia to facilitate PDT via laparotomy at primary surgical debulking or laparoscopy at second-look in the setting of microscopic or low-volume recurrent disease.

These results indicate that combination therapy improved the acute response of tumor burden to treatment without accompanying increments in toxicity.

Summary

The results presented herein demonstrate a marked reduction in toxicity of PDT, together with a more dramatic reduction in tumor volume following administration of combination therapy. Combination therapy approaches are thus useful for the management of advanced and recurrent epithelial ovarian cancer.

Example 4

In vitro Analysis of PIC Specificity

Specificity for tumor cell epitopes is an important or useful feature of PICs. PICs advantageously localize to tumor tissues, thereby decreasing the amount of damage to normal tissue that results from non-specific photoactivation of photosensitizers. PICs are also ideal for cancer-related diagnostic methods. Non-specific localization of photosensitizers to normal tissues can produce prohibitive levels of background. Specific targeting of PICs to tumor tissue reduces background and improves diagnostic specificity.

Comparison of C225 PIC to free photosensitizer, BPD, and to C225, in cells with respect to uptake, phototoxicity and subcellular localization revealed that C225 PIC is highly specific for EGFR positive cells. In addition, blockade of EGFR function by C225 PIC was shown to inhibit downstream signaling molecules. C225 PIC inhibition of EGFR function and inhibition of downstream signal transduction cascades indicates that C225 PICs can have inhibitory effects on a variety of EGFR propagated cancers. PICs, such as C225 PIC, are ideally suited for many diagnostic and therapeutic cancer-related applications.

Preparation and Purification of Cell Lines

CHO cells (provided by T. Heitner of the University of California, San Francisco) stably transfected with EGFR full-length receptor ("CHO-EGF") or ErbB2 ("CHO-ERBB2") were utilized to assess binding specificity and functionality of C225 PIC. Cells were grown in Ham's F12 selective media, containing 0.8 µg/ml G418/neomycin, with 10% FCS. The parent cell line (CHO) was grown in non-selective Ham's F12 complete media. The expression of the human EGFR by the CHO-EGF cells was confirmed by Western blot (FIG. 12) probing with the anti-EGFR antibody LA1 (Upstate Biotech, Lake Placid, N.Y.). Negative control CHO-ERBB2 cells did not show expression of the EGFR. Blots were reprobed with anti-actin (Santa Cruz Biotechnology, Santa Cruz, Calif.) to control for equal loading.

EGFR-Positive Cells Specifically Take Up C225 PIC

To compare the uptake of C225 PIC and free BPD in transfected cells as well as in human tumor cells, CHO, CHO-EGF, CHO-ERBB2 and OVCAR-5 cells were studied as previously described (Hamblin et al., 1996). NIH:OVCAR-5 cells were obtained from the Fox Chase Cancer Institute (Philadelphia, Pa.), maintained in RPMI-1640 (Mediatech Inc, Herndon, Va.) and supplemented with 10% heat-inactivated fetal calf serum (FCS, GIBCO Life Technologies, Grand Island, N.Y.), 100 U/ml penicillin and 100 µg/ml streptomycin. Briefly, the cells were incubated for 15 hours with either 140 nM BPD or the equivalent of C225 PIC. A quantitation of the uptake of both free BPD and C225 PIC was achieved by measuring the BPD fluorescence (expressed as µmol of PS/mg cell protein) in cell lysates, prepared in NaOH/SDS after incubation and comparison of this fluorescence to standard curves of BPD.

Figure 13:
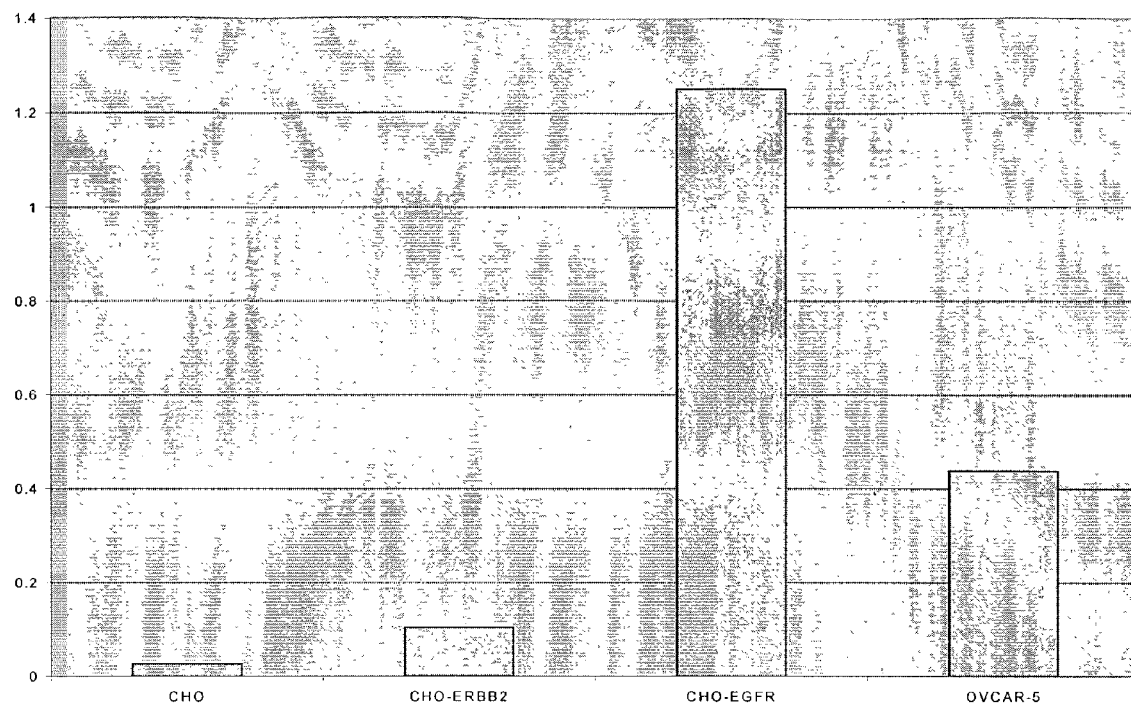
FIG. 13 depicts the relative uptake of C225 PIC and free BPD for different cell types.

The relative uptake, defined as the of C225 PIC uptake to BPD uptake, for the different cell types was determined (FIG. 13). The EGFR negative CHO cells (CHO and CHO-ERBB2) had a very limited uptake of the C225 PIC (ratio 0.027 and 0.103 respectively), while in CHO-EGFR cells, the C225 PIC was taken up to the same extent as free BPD (ratio 1.25). In OVCAR-5 cells, which expressed EGFR to a much lesser extent than the transfected CHO-EGFR cells, the ratio was at least four times higher than in the EGFR negative cells (ratio 0.438). These results indicated an increased uptake of the C225 PIC by EGFR-transfected cells and human tumor cells in comparison to non-transfected or ErbB2-transfected control cells.

Phototoxicity of C225 PIC is Specific for EGFR Expressing Cells

To show the specific uptake and phototoxicity of the C225 PIC conjugate in EGFR positive cells, the following procedures for PDT/PIT and cytotoxicity were applied to the cells. For PDT/PIT, a solid state diode laser (BWF 690-1, B&W TEK, Newark, Del.), which delivered monochromatic light (690+/−5 nm) to overlap closely the absorption maximum of BPD (690 nm) was utilized. This light was focused to a spot of 3.5 cm diameter, which corresponded to a power density of circa 40 mW/cm$^2$. PDT/PIT using either free BPD or C225 PIC conjugate was performed as previously described (Duska et al., 1999). Briefly, OVCAR-5 or CHO cells were plated in 35 mm dishes, incubated with BPD or C225 PIC for 15 hours and subsequently illuminated with different doses of light. MTT assay was performed or cell lysates were prepared for western blotting either 24 or 72 hours after PDT/PIT.

To determine the survival fraction of cells after treatment, the 3-(4,5-dimethylthiazol-2-yl)-2,5-diphenyltetrazolium bromide ("MTT") assay, which measured mitochondrial dehydrogenase activity, was used. Cells were incubated with 0.5 mg/ml MTT for 1 hour to measure its reduction by mitochondrial dehydrogenases. The dehydrogenase activity 24 hours after PDT provided a sensitive method of assessing the number of surviving cells and has been shown to correlate well with other established measures of cytotoxicity, such as the clonogenic assay (Mosmann, 1983). The MTT assay has been used to test for chemosensitivity to anti-cancer drugs (Carmichael et al., 1988), as well as to determine viability after PDT (McHale and McHale, 1988), (Merlin et al., 1992).

Figure 14A:
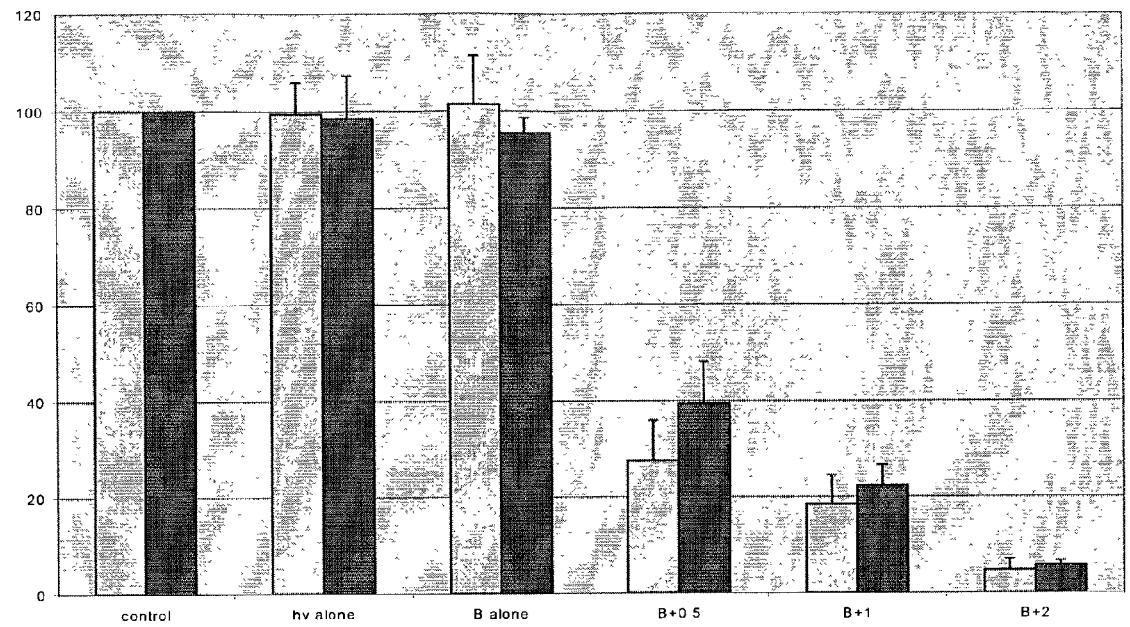
FIG. 14 depicts viability of cells as measured by MTT assay.
Figure 14B:
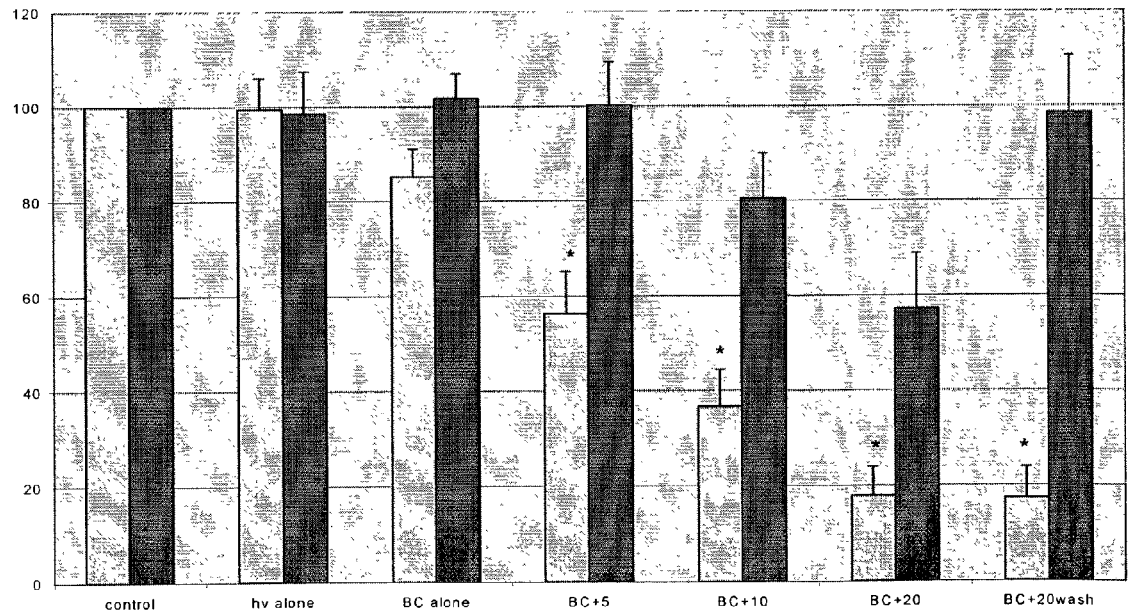

The specific uptake of the C225 PIC conjugate led to a marked phototoxicity in the EGFR positive cells. Free BPD (140 nM) caused a decrease in cell viability as measured by the MTT assay 24 hours after illumination with red light in both CHO-EGF and CHO-ERBB2 cells (FIG. 14A). Both cell types showed less than 20% viability at a light dose of 2 J/cm$^2$. In contrast, C225 PIC (BPD concentration of 140 nM) caused significantly ($p<0.05$) more toxicity upon illumination in the CHO-EGFR cells as compared to the CHO-ERBB2 cells (FIG. 14B). At a dose of 20 J/cm$^2$, viability of the CHO-EGF cells decreased to lower than 20%, while the CHO-ERBB2 cells had a viability of 60% as measured by the MTT assay, 24 hours after illumination. In addition, when the excess C225 PIC was washed away before illumination by a wash-step with culture medium, viability of the CHO-ERBB2 cells was around 90% 24 hours after illumination, while the viability of the CHO-EGF cells remained low at less than 20%.

Phototoxicity of C225 PIC in OVCAR-5 Cells

Figure 15:
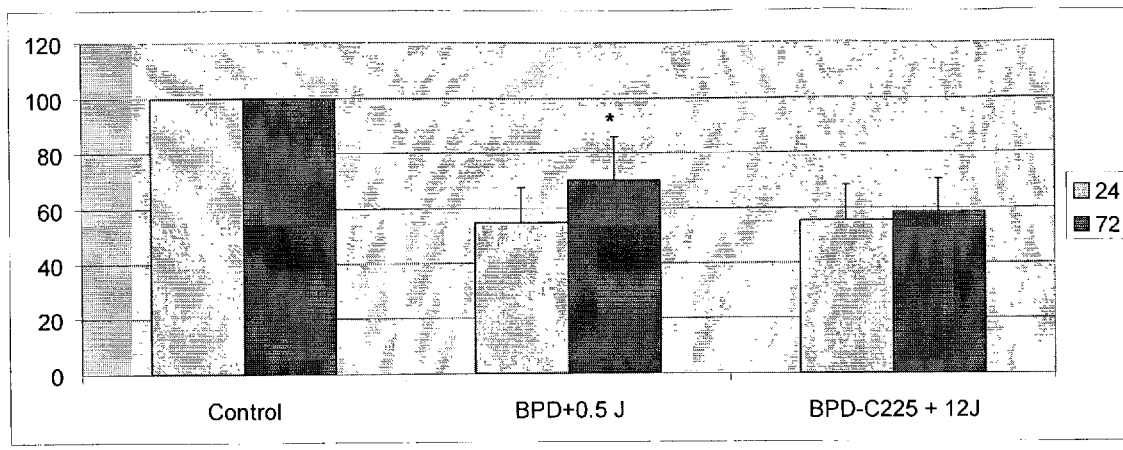
FIG. 15 depicts the viability of OVCAR-5 cells as measured by MTT assay.

The MTT assay was also applied to OVCAR-5 cells to evaluate specific uptake and phototoxicity of C225 PIC. The MTT assay was performed 24 and 72 hours after treatment. The OVCAR-5 cells were less sensitive to phototoxic action by C225 PIC and red light than the CHO-EGFR cells (50% decrease in viability at a light dose of 12 and 6.5 J/cm$^2$ respectively). This effect is attributable to a lower uptake rate of C225 PIC in OVCAR-5 cells, because these cells express lower levels of EGFR. The decrease in viability in OVCAR-5 after treatment with BPD or C225 PIC and light was determined, both at 24 hours and 72 hours (FIG. 15). The light doses were adjusted so that in both treatment groups, only 50% survived after 24 hours. As compared to the control cells at the same time-point, the BPD and light treated cells showed an increased MTT activity (15%) between the 24 and 72 hours time-point. In the C225 PIC and light treated cells, this "rebound" effect was not observed. C225 alone, at a similar concentration as present in the C225 PIC conjugate (20 nM), did not have an effect in the MTT assay, at either 24 or 72 hours.

BPD Localizes in the Mitochondria, C225 PIC in the Lysosomes

To determine the subcellular localization of BPD and the C225 PIC, confocal microscopy studies were performed as published previously (Runnels et al., 1999), (Pogue et al., 2001). Cells were grown on coverslips, incubated for 15 hours with BPD or C225 PIC and cells were mounted on microscope slides in PBS, thus allowing visualization of live cells. Colocalization studies were performed by incubating the cells for the final 15 minutes with either LysoTracker® Green (Molecular Probes, Eugene, Oreg.) or Rhodamine 123 for staining of lysosomes or mitochondria, respectively. A Leica confocal laser scanning microscope consisting of a Leica TCS 4D scanner attached to a Leitz DMBR/E microscope was operated using the TCS-NT software (Leica, Deerfield, Ill.). The 488 nm line of an argon ion laser was used for excitation. The fluorescent signal emitted from the sample was separated into two detection channels by a 580 nm dichroic mirror. The reflected portion in the green range (below 580 nm) passed through a bandpass filter (525-550 nm) before it was collected by the first photomultiplier tube detector. The light that was transmitted in the red range (above 580 nm) was passed through a 590 nm longpass filter and collected by a second detector. The fluorescent images were displayed in green and red "false" color output and electronically combined for visualizing colocalization.

The localization of free BPD and C225 PIC (BPD concentration of 140 nM) after 15 hours incubation with CHO-EGF and CHO-ERBB2 cells was visualized with confocal laser fluorescence microscopy (FIG. 16). Free BPD (red) localized in a similar fashion in both CHO-EGFR and CHO-ERBB2 cells. After incubation with C225 PIC, a distinct pattern of fluorescence was observed in the EGFR positive cells only.

The subcellular localization of the C225 PIC conjugate was studied in greater detail in OVCAR-5 cells. The C225 PIC conjugate localized in OVCAR-5 in a similar way as in the CHO-EGFR cells (FIG. 17). The results showed a clear overlap of the LysoTracker with the C225 PIC. Staining resulted in a yellow fluorescence where both C225 PIC and LysoTracker were present. The Rhodamine 123 showed a fluorescence pattern distinct from the C225 PIC fluorescence, but overlapping with free BPD. These results indicated BPD localization in the mitochondria and C225 PIC localization in the lysosomes.

C225 PIC Blocks EGF-Induced EGFR Phosphorylation

To examine the phosphorylation of the EGFR by EGF after PDT/PIT, cells were treated with PDT, PIT or C225, and subsequently EGF-stimulated and then prepared for Western blotting. The following 14 groups were included: no treatment with or without EGF stimulation, C225 PIC with or without EGF, C225 PIC+light with or without EGF, BPD alone with or without EGF, BPD+light with or without EGF, light alone with or without EGF, and C225 with or without EGF. The concentration of BPD or C225 PIC was 140 nM (BPD equivalent). The light dose was chosen so that 50% of the cells were viable after 24 hours as determined by MTT assay. The dose of C225 was 20 nM, based on the amount of C225 conjugated to BPD in C225 PIC (BPD:C225=7:1). Twenty-four hours after photodynamic treatment as described above, OVCAR 5 cells in the groups to be stimulated with EGF were incubated for 15 min with 10 ng/ml EGF in prewarmed culture medium. The groups that were not stimulated with EGF only received prewarmed culture medium. After the 15 minute incubation, cells were kept on ice and cell lysates were collected in RIPA buffer (containing 0.1% SDS and 1% NP-40). After protein determination by a modified Lowry assay (Biorad, Hercules, Calif.), the proteins were run on SDS-PAGE, transferred to a polyvinylidene diflouride (PVDF) membrane (Immobilon-P, Millipore, Bedford, Mass.) and probed with the first antibody. To detect the phosphorylation of the EGFR, the anti-phosphotyrosine antibody 4G10 (New England Biolabs; Beverly, Mass.) was used. A secondary goat anti-mouse antibody, coupled to horseradish peroxidase (Biorad), was used in combination with a chemiluminescence kit (Amersham, Arlington Heights, Ill.) to visualize the specific bands. Western blots were reprobed with anti-actin (Santa Cruz Biotechnology, Santa Cruz, Calif.) to control for equal loading.

C225 has been shown previously to block EGF-induced EGFR phosphorylation. In the present study, the effect of PIT on two different EGF-induced signaling pathways was studied. PDT or PIT was performed at a dose which showed 50% survival after 24 hours in the MTT assay. Cells were stimulated with 10 ng/ml EGF for 15 min, the conditions under which maximum phosphorylation of the EGFR was observed. EGFR phosphorylation by EGF was inhibited by both C225 as well as C225 PIC, with or without light treatment. This inhibition can be observed both at 24 and 72 hours after light treatment. In contrast, BPD plus light did not inhibit EGF-induced phosphorylation of the EGFR (FIG. 18). Cells treated with BPD alone, or 12 J/cm$^2$ light alone, reacted like control cells to the EGF stimulation.

C225 PIC Blocks the Phosphorylation of ERK-1/2 and Akt-1 by EGF

Figure 19A:
FIG. 19 depicts phosphorylation of both Akt-1 and MAPK/ERK by EGF, which was inhibited by treatment with C225 or by treatment with C225 PIC but not by treatment with BPD plus light.
Figure 19B:
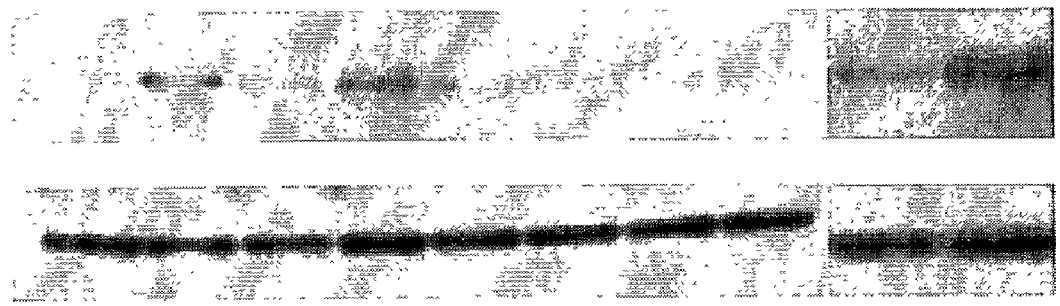

Two important pathways which are regulated by EGFR are the PI3K-Akt/PKB-1 and the Ras-MAPK/ERK pathway. These signaling molecules are implicated in a variety oncogenic pathways. To determine the inhibition of these two downstream signaling molecules (i.e., Akt-1 and MAPK/ERK of the EGFR system), Western blotting procedures were again applied. To detect the phosphorylation of MAPK-1/2 the anti-phospho-MAPK p42/p44 antibody (New England Biolabs) was used, and to detect the phosphorylation of Akt the anti-phospho-Akt (ser 473) antibody (New England Biolabs) was used. EGF (10 ng/ml; 15 min) induced the phosphorylation of both Akt-1 and MAPK/ERK, indicating that in OVCAR-5 cells, activation of these pathways can be induced by EGF (FIG. 19). However, these EGF-induced phosphorylation events were inhibited by C225 alone or C225 PIC, either with or without illumination. On the other hand, BPD plus light did not have an inhibitory effect on the EGF-induced activation of either Akt-1 or MAPK/ERK. Cells treated with BPD alone or 12 J/cm$^2$ light alone responded like control cells to the EGF stimulation. This finding was in accordance with the data on phosphorylation of EGFR, indicating inhibition by C225 of these two downstream pathways.

Example 5

In vivo Analysis of PICs

The conjugation of a monoclonal antibody to a photosensitizer compound by the methods described herein offers improved specificity in photosensitizer delivery. As shown in Example 4, the increased specificity of the PICs improves the use of PDT technology in diagnostic applications. Because the PICs described herein possess both increased specificity and dual potency, an enhanced therapeutic effect results. These findings are of great significance for the treatment of tumor tissues that are otherwise difficult to access. The in vivo effectiveness of PICs in targeting and reducing the proliferation of tumor cells is demonstrated in this example.

Murine Tumor Model for Human Ovarian Cancer

The effects of PIC treatment on tumor burden were evaluated using the intraperitoneal murine model. Animal care and NIH:OVCAR-5 cell culture and intraperitoneal injection were performed as described in Example 3.

Photoimmunoconjugate (PIC)

The PIC was constructed according to the methods of Example 1, with the $Ce_6$ photosensitizer linked directly to the lysine residues on the C225 antibody. Nineteen days post-inoculation of tumor cells, mice were injected with the PIC. Administeration was intraperitoneal, at a dose of 1.0 mg/kg $Ce_6$ equivalent, in 1 cc of Dulbecco's Phosphate Buffered Salt Solution without $Ca^{2+}/Mg^{2+}$ using a 27-gauge needle.

Light Delivery

At 15-18 hours post-PIC injection, animals were irradiated using a 665 nm diode laser and diffusing tip fiber. The animals were anesthetized (105 mg/kg Ketamine, 15 mg/kg Xylazine; i.p.) and a 22-gauge catheter was inserted into the peritoneal cavity. Two cc of a 0.1% Intralipid solution (Intralipid +PBS without $Ca^{2+}/Mg^{2+}$) was injected intraperitoneally via the catheter. A diffusing tip fiber optic was then inserted through the catheter into the peritoneal cavity. A total light dose of 25 $J/cm^2$ was divided equally over four quadrants in the peritoneum to insure uniform light delivery to the various regions of the cavity. The animals were treated with 665 nm light from a diode laser at a fluence rate of either 30 or 180 $mW/cm^2$.

Necropsy

Twenty-four days post-inoculation, the animals were sacrificed and tumor burden was evaluated by two investigators. Tumors were systematically resected and weighed from six major sites: Sub-gastric Omentum, Pelvic Omentum, Pelvis (uterus and adnexae), Bowel Mesentery, Diaphragm, and Peritoneal Wall. Frozen and formalin-fixed samples were kept for histology.

Tumoricidal Response

Figure 20:
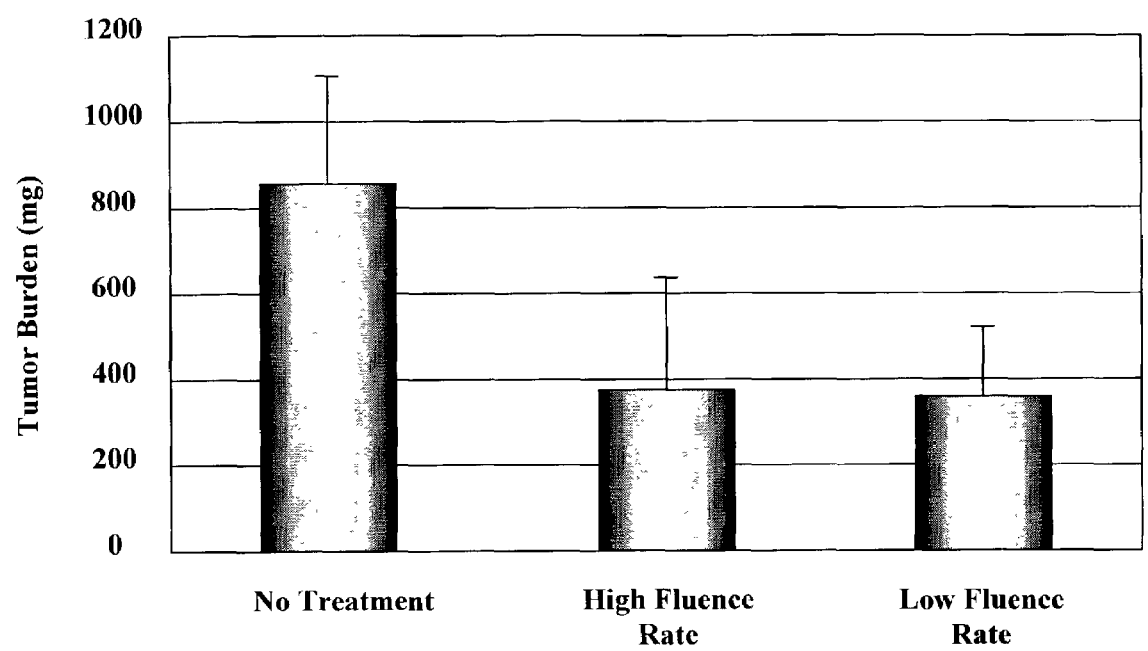
FIG. 20 depicts the average weight of residual carcinoma at the time of necropsy in mice that underwent PIT following the administration of a PIC.

The results (FIG. 20) indicate that PIT reduced the tumor burden to 45% of no treatment controls for both the high (180 $mW/cm^2$) and low (30 $mW/cm^2$) fluence rates. No statistically significant difference in tumor burden was observed between the two PIT treatment groups. A relatively low, sub-curative PDT dose was deliberately chosen to examine factors such as the effect of fluence rate and various combination therapies in an effort to optimize PIT treatment regimens. The results of these in vivo experiments demonstrate that the prior limitations and difficulties associated with the therapeutic use of PICs have been overcome by this invention.

LIST OF REFERENCES

Methods in Enzymology, (Academic Press, Inc.)
TimeMaster fluorescence lifetime spectrometer reference manual. (1994) South Brunswick, N.J.: Photon Technology International, Inc. (South Brunswick, N.J., Photon Technology International, Inc.,)
Fluorescence system user's manual, version 1.2x/TimeMaster Pro software user's manual. (1998) (Monmouth Junction, N.J., Photon Technology International, Inc.)
Aprelikova O., Pajusola K., Partanen J., Armstrong E., Alitalo R., Bailey S. K., McMahon J., Wasmuth J., Huebner K., and Alitalo K. (1992) FLT4, a novel class III receptor tyrosine kinase in chromosome 5q33-qter. Cancer Res. 52, 746-748.
Ausubel, et al. (1987) Current Protocols in Molecular Biology.
Aveline, B., Hasan, T., and Redmond, R. W. (1994) Photophysical and photosensitizing properties of benzoporphyrin derivative monoacid ring A (BPD-MA), Photochem Photobiol 59, 328-35.
Baba, T., Black, K. L., Ikezaki, K., Chen, K. N., and Becker, D. P. (1991) Intracarotid infusion of leukotriene C4 selectively increases blood-brain barrier permeability after focal ischemia in rats., J Cereb Blood Flow Metab 11, 638-43.
Bauminger, S. and Wilchek, M. (1980) The use of carbodiimides in the preparation of immunizing conjugates., Methods Enzymol 70, 151-159.
Bevington, P. R. (1969) Data reduction and error analysis for the physical sciences. (New York, McGraw-Hill)
Bodanszky, M. (1993) Side reactions due to overactivation. In Principles of Peptide Synthesis (New York, Springer-Verlag), pp. 195-196.
Bolis, G., Villa, A., Guarnerio, P., Ferraris, C., Gavoni, N., Giardina, G., Melpignano, M., Scarfone, G., Zanaboni, F., and Parazzini, F. (1996) Survival of women with advanced ovarian cancer and complete pathologic response at second-look laparotomy, Cancer 77, 128-31.
Carmichael, J., Mitchell, J. B., DeGraff, W. G., Gamson, J., Gazdar, A. F., Johnson, B. E., Glatstein, E., and Minna, J. D. (1988) Chemosensitivity testing of human lung cancer cell lines using the MTT assay, Br J Cancer 57, 540-7.
Coligan, et al. (1991) Current Protocols in Immunology.
Del Governatore, M., Hamblin, M. R., Piccinini, E. E., Ugolini, G., and Hasan, T. (2000) Targeted photodestruction of human colon cancer cells using charged 17.1 A chlorin e6 immunoconjugates, Br J Cancer 82, 56-64.
Dougherty, T. J., Gomer, C. J., Henderson, B. W., Jori, G., Kessel, D., Korbelik, M., Moan, J., and Peng, Q. (1998) Photodynamic therapy, J Natl Cancer Inst 90, 889-905.
Duska, L., Hamblin, M., Miller, J., and Hasan, T. (1999) Combination photoimmunotherapy and cisplatin: effects on human ovarian cancer ex vivo, J Natl Cancer Inst 91, 1557-1563.
Fan, Z. and Mendelsohn. (1998) Therapeutic application of anti-growth factor receptor antibodies., J Curr Opin Oncol 10, 67-73.
Fielder, W. Graeven U., Ergun S., Verago S., Kilic N., Stockschlader M., and Hossfeld D. K. (1997) Expression of FLT4 and its ligand VEGF-C in acute myeloid leukemia. Leukemia 11, 1234-1237.
Finnerty, H., Kelleher K., Morris G. E., Bean K., Merberg D. M., Kriz R., Morris J. C., Sookdeo H., Turner K. J., and Wood C. R. (1993) Molecular cloning of murine FLT and FLT4. Oncogene 8, 2293-2298.
Fletcher, M. and Goldstein, A. L. (1987) Recent advances in the understanding of the biochemistry and clinical pharmacology of interleukin-2. Lymphokine Res 6, 45-57.
Freshney, R. I. (1987) Animal Cell Culture.
Gait, M. D. (1984) Oligonucleotide Synthesis.
Gennuso, R., Spigelman, M. K., Chinol, M., Zappulla, R. A., Nieves, J., Vallabhajosula, S., Alberto Paciucci P, Goldsmith, S. J. a., and Holland, J. F. (1993) Effect of blood-brain barrier and blood-tumor barrier modification on central nervous system liposomal uptake, Cancer Invest 11, 118-28.

Goldstein, N. I., Prewett, M., Zuklys, K., Rockwell, P., and Mendelsohn, J. (1995) Biological efficacy of a chimeric antibody to the epidermal growth factor receptor in a human tumor xenograft model, Clin Cancer Res 1, 1311-8.

Greenlee, R. T., Murray, T., Bolden, S., and Wingo, P. A. (2000) Cancer statistics, 2000, CA Cancer J Clin 50, 7-33.

Gross, S., and Brandis, A., Chen, L., Rosenbach-Belkin, V., Roehrs, S., Scherz, A., and Salomon, Y. (1997) Protein-A-mediated targeting of bacteriochlorophyll-IgG to *Staphylococcus aureus*: a model for enhanced site-specific photocytotoxicity., Photochem Photobiol, 66, 872-878.

Hamblin, M. R., Del Governatore, M., Rizvi, I. a., and Hasan, T. (2000a) Biodistribution of charged 17.1 A photoimmunoconjugates in a murine model of hepatic metastasis of colorectal cancer, Br J Cancer 83, 1544-41.

Hamblin, M. R., Miller, J. L. and Ortel, B. (2000b) Scavenger-receptor targeted photodynamic therapy. Photochem Photobiol, 72, 533-540.

Hamblin, M. R., Miller, J. L., and Hasan, T. (1996) Effect of charge on the interaction of site-specific photoimmunoconjugates with human ovarian cancer cells, Cancer Res 56, 5205-10.

Hames, B. D., and Rickwood, D. E. (1996) In Gel Electrophoresis of Proteins: A Practical Approach. (New York, Oxford University Press Inc.), pp. 113-114.

Harlow and Lane (1988) Antibodies: A Laboratory Manual, Cold Spring Harbor Laboratory, New York.

Hasan, T. (1992) Photosensitizer delivery mediated by macromolecular carrier systems. In Photodynamic therapy: Basic principals and clinical applications, T. J. Dougherty and B. W. Henderson. (New York, N.Y., Marcel Dekker), pp. 187-200.

Heitner, T., Moor, A., Garrison, J. L., Marks, C., Hasan, T. and Marks, J. D. (2001) Selection of cell binding and internalizing epidermal growth factor receptor antibodies from a phage display library. J Immunol Methods 248, 17-30.

Jiang, F. N., Allison, B., Liu, D., and Levy, J. G. (1992) Enhanced Photodynamic Killing of Target Cells by Either Monoclonal Antibody or Low Density Lipoprotein Mediated Delivery Systems., J Controlled Release 19, 41-58.

Jiang, F. N., Jiang, S., Liu, D., Richter, A., and Levy, J. G. (1990) Development of Technology for Linking Photosensitizers to a Model Monoclonal Antibody, J Immunol Methods, 134.

Jiang, F. N., Liu, D. J., Neyndorff, H., Chester, M., Jiang, S., and Levy, J. G. (1991) Photodynamic Killing of Human Squamous Cell Carcinoma Cells Using a Monoclonal Antibody-Photosensitizer Conjugate, JNCI 83, 1218-1225.

Jiang, F. N., Richter A. M., Jain, A. K., Levy, J. G., and Smits, C. (1993) Biodistribution of a Benzoporphyrin Derivative-Monoclonal Antibody Conjugate in A549-Tumor-bearing Nude Mice, Biotechnol Ther 4, 43-61.

Kubo H., Fujiwara T., Jussila L., Hashi H., Ogawa M., Shimizu K., Awane M., Sakai Y., Takabayashi A., Alitalo K., Yamaoka Y., and Nishikawa S. I. (2000) Involvement of vascular endothelial growth factor receptor-3 in maintenance of integrity of endothelial cell lining during tumor angiogenesis. Blood 96, 546-553.

Laemmli, U. K. (1970) Cleavage of structural proteins during the assembly of the head of bacteriophage T4, Nature 227, 680-685.

Larrivee, B. and Karsan, A. (2000) Signaling pathways induced by vascular endothelial growth factor (review). Int. J. Mol. Med. 5, 447-456.

Levy, J. G. (1994) Photosensitizers in photodynamic therapy, Semin Oncol 21, 4-10.

Levy, J. G., Dolphin, D., and Chow, J. K. (1989) Wavelength-specific cytotoxic agents. (U.S. Pat. No. 4,883,790)

Marconcini, L., Marchio S., Morbidelli L., Cartocci E., Albini A., Ziche M., Bussolino F., and Oliviero S. (1999) c-fos-induced growth factor/vascular endothelial growth factor D induces angiogenesis in vivo and in vitro. Proc. Natl. Acad. Sci. USA 96, 9671-9676.

Marcus, S. L. (1992) Photodynamic therapy of human cancer. Proc IEEE 80, 869-886.

McHale, A. P., and McHale, L. (1988) Use of a tetrazolium based calorimetric assay in assessing photoradiation therapy in vitro, Cancer Lett 41, 315-21.

Merlin, J. L., Azzi, S., Lignon, D., Ramacci, C., Zeghari, N., and Guillemin, F. (1992) MTT assays allow quick and reliable measurement of the response of human tumor cells to photodynamic therapy, Eur J Cancer 28A.

Mew, D., Wat, C. K., Lum, C. K., Towers, G. H. N., Sun C. H. C., Walter, R. T., Berns, M. W., and Levy, J. G. (1985) Ability of specific monoclonal antibodies and conventional antisera conjugated to hematoporphyrin to label and kill selected cell lines subsequent to light activation. Cancer Res 45, 4380-4386.

Mew, D., Wat, C. K., Towers, G. H., and Levy, J. G. (1983) Photoimmunotherapy: treatment of animal tumors with tumor-specific monoclonal antibody-hematoporphyrin conjugates, J Immunol 130, 1473-7.

Miller, J. M., and Calos, M. P. (1987) Gene Transfer Vectors for Mammalian Cells.

Molpus, K. L;, Hamblin, M. R., Rizvi, I., and Hasan, T-. (2000) Intraperitoneal Photoimmunotherapy of Ovarian Carcinoma Xenografts in Nude Mice Using Charged Photoimmunoconjugates, Gynecol Oncol 76, 397-404.

Molpus, K. L., Kato, D., Hamblin, M. R., Lilge, L., Bamberg, M., and Hasan, T. (1996a) Intraperitoneal photodynamic therapy of human epithelial ovarian carcinomatosis in a xenograft murine model, Cancer Res 56, 1075-82.

Molpus, K. L., Koelliker, D., Atkins, L., Kato, D. T., Buczek-Thomas, J., Fuller, A. F., Jr., and Hasan, T. (1996b) Characterization of a xenograft model of human ovarian carcinoma which produces intraperitoneal carcinomatosis and metastases in mice, Int J Cancer 68, 588-95.

Mosmann, B. T. (1983) Rapid colorimetric assay for cellular growth and survival: application to proliferation and cytotoxicity assays., J Immunol Methods, 65, 55-63.

Mullis (1994) (PCR: The Polymerase Chain Reaction)

Neuwelt, E. A., and Rapoport, S. I. (1984) Modification of the blood-brain barrier in the chemotherapy of malignant brain tumors., Fed Proc 43, 214-9.

Ozols, R. F. (1994) Treatment of ovarian cancer: current status, Semin Oncol 21, 1-9; quiz 10, 58.

Paavonen K., Puolakkainen P., Jussila L., Jahkola T., and Alitalo K. (2000) Vascular endothelial growth factor receptor-3 in lymphangiogenesis in wound healing. Am. J. Pathol. 156, 1499-1504.

Parrish, I. A., Anderson, R. R., Urbach, F. and Pitts, D. (1978) Optical properties of the skin and eyes. UV A: biological effects of ultraviolet radiation with emphasis on human responses to longwave ultraviolet. (New York, N.Y.: Plenum)

Perkins, A. S., and Stern, D. F. In: Cancer: Principles and Practice of Oncology, Eds. Philadelphia: Lippincott-Raven, 79-102, 1997. (1997) In Cancer: Principles and Practice of Oncology, S. H. V. T. DeVita, S. A. Rosenberg, ed. (Philadelphia, Lippincott-Raven,), pp. 79-102.

Pizza, G., Severini, G., Menniti, D., De Vinci, C., and Corrado, F. (1984) Tumour regression after intralesional injection of interleukin 2 (IL-2) in bladder cancer. Preliminary report., Int J Cancer 34, 359-67.

Pogue, B. W., Ortel, B., Chen, N., Redmond, R. W., and Hasan, T. (2001) A photobiological and photophysical-based study of phototoxicity of two chlorins., Cancer Res 61, 717-24.

Pruss, R. M., and Herschman, H. R. (1977) Variants of 3T3 cells lacking mitogenic response to epidermal growth factor., Proc Natl Acad Sci USA 74, 3918-3921.

Rabinowich, H., Cohen, R., Bruderman, I., Z., S., and Klajman, A. (1987) Functional analysis of mononuclear cells infiltrating into tumors: lysis of autologous human tumor cells by cultured infiltrating lymphocytes., Cancer Res 47, 173-7.

Richter, A. M., Kelly, B., Chow, J., Liu, D. J., Towers, G. H. N., Dolphin, D., and Levy, J. G. (1987) Preliminary studies on a more effective phototoxic agent than hematoporphyrin, JNCI 79, 1327-1331.

Rosenberg, S. A., Spiess, P., and Lafreniere, R. (1986) A new approach to the adoptive immunotherapy of cancer with tumor-infiltrating lymphocytes., Science 233, 1318-21.

Runnels, J. M., Chen, N., Ortel, B., Kato, D., and Hasan, T. (1999) BPD-MA-mediated photosensitization in vitro and in vivo: cellular adhesion and betal integrin expression in ovarian cancer cells, Br J Cancer 80, 946-53.

Saaristo A., Partanen T. A., Arola J., Jussila L., Hytonen M., Makitie A., Vento S., Kaipainen A., Malmberg H., and Alitalo K. (2000) Vascular endothelial growth factor-C and its receptor VEGFR-3 in the nasal mucosa and in nasopharyngeal tumors. Am. J. Pathol. 157, 7-14.

Sambrook, e. a. (1989) Molecular Cloning: A Laboratory Manual, Second edn.

Savellano, M. D. (2000) Photodynamic Targeting with Photosensitizer Immunoconjugates., PhD Thesis, Department of Biomedical Engineering, University of Michigan, UMI Dissertations Publishing, In press.

Sperduto, P. W., DeLaney, T. F., Thomas, G., Smith, P., Dachowski, L. J., Russo, A., Bonner, R., and Glatstein, E. (1991) Photodynamic therapy for chest wall recurrence in breast cancer., Int J Radiat Oncol Biol Phys 21, 441-6.

Steele, K. J., Liu, D., Stammers, A. T., Deal, H., Whitney, S., and Levy, J. G. (1988) Suppressor deletion therapy: selective elimination of T suppressor cells using a hematoporphyrin conjugated monoclonal antibody. in Antibody-mediated Delivery Systems (New York, Marcel Dekker, Inc.), pp. 157-189.

Sternberg, E. D., Dolphin, D., and Drückner, C. (1998) Porphyrin-based photosensitizers for use in photodynamic therapy, Tetrahedron 54, 4151-4202.

Strong, L., D. M., Y., and Yarmush, M. L. (1994) Photophysical, biochemical, and pharmacokinetic properties of antibacterial conjugates, Ann N Y Acad Sci 745, 297-320.

Svaasand, L. O., and Ellingsen, R. (1983) Optical properties of human brain, Photochem Photo-biol 38, 293-299.

Waksal, H. W. (1999) Role of an anti-epidermal growth factor receptor in treating cancer, Cancer Metastasis Rev 18, 427-36.

Walther, M. M., Delaney, T. F., Smith, P. D., Friauf, W. S., Thomas, G. F., Shawker, T. H., Vargas, M. P., Choyke, P. L., Linehan, W. M., Abraham, E. H., et al. (1997) Phase I trial of photodynamic therapy in the treatment of recurrent superficial transitional cell carcinoma of the bladder, Urology 50, 199-206.

Weir, D. M. (1996) Handbook of Experimental Immunology.

Wilson, B. C. (1989) Photodynamic therapy: light delivery and dosage for second-generation photosensitizers. Photosensitizing compounds: their chemistry, biology and clinical use., CIBA Found Symp 146, 60-77.

Yarmush, M. L., Thorpe, W. P., Strong, L., Rakestraw, S. L., Toner, M., and Tompkins, R. G. (1993) Antibody targeted photolysis, Critical Reviews in Therapeutic Drug Carrier Systems 10, 197-252.

We claim:

1. A method of achieving a synergistic reduction in tumor burden in a subject having a tumor, the method comprising the steps of
   a) administering a therapeutically effective amount of at least one photosensitizer, wherein the photosensitizer is taken up by a tumor;
   b) administering a therapeutically effective amount of an antibody that binds with specificity to an epidermal growth factor receptor (EGFR), blocks extracellular ligand binding to the EGFR and exerts an inhibitory effect on growth and/or proliferation of the tumor and wherein the photosensitizer and the antibody do not comprise a photoimmunoconjugate;
   c) localizing the antibody to the tumor; and light-activating the tumor cell to produce a phototoxic species, thereby achieving a synergistic reduction in tumor burden in the subject.

2. The method of claim 1, wherein the photosensitizer is selected from the group consisting of photofrin$^{RTM}$, synthetic diporphyrins and dichlorins, phthalocyanines with or without metal substituents, chloroaluminum phthalocyan me with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorine $e_6$, mono-l-aspartyl derivative of chlorine $e_6$, di-l-aspartyl derivative of chlorine $e_6$, tin(IV) chlorine $e_6$, meta-tetrahydroxyphenylchlorin, benzoporphyrin derivatives, benzoporphyrin monoacid derivatives, tetracyanoethylene adducts of benzoporphyrin, dimethyl acetylenedicarboxylate adducts of benzoporphyrin, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, 5- aminolevulinic acid benzonaphthoporphyrazines, cationic imminium salts, tetracyclines, lutetium texaphyrin, tin-etio-purpurin, porphycenes, benzophenothiazinium and combinations thereof.

3. The method of claim 1, wherein the photosensitizer is benzoporphyrin derivative.

4. The method of claim 1, wherein the antibody is ABX-EGF.

5. The method of claim 1, wherein the antibody is IMC-C225.

6. The method of claim 1, wherein light-activating comprises applying a suitable light source selected from the group consisting of a filtered conventional light source, a diode array, and a laser.

7. The method of claim 1, wherein the subject has ovarian cancer.

8. The method of claim 1, wherein the tumor is derived from a tissue selected from the group consisting of breast, prostate, colon, lung, pharnyx, thyroid, lymphoid, larynx, esophagus, oral mucosa, bladder, stomach, intestine, liver, pancreas, ovary, oral mucosa, uterus, cervix, testes, dermis, bone, blood and brain.

9. A method of achieving a synergistic reduction in tumor burden in a subject having a tumor, the method comprising the steps of:
   a) administering a therapeutically effective amount of at least one photosensitizer, wherein the photosensitizer is taken up by a tumor;
   b) administering a therapeutically effective amount of an antibody, wherein the antibody binds with specificity to VEGF and exerts an inhibitory effect on growth and/or proliferation of the tumor; and
   c) light-activating the tumor to produce a phototoxic species, thereby achieving a synergistic reduction in tumor burden in the subject.

10. The method of claim 9, wherein the antibody is rhuMAb VEGF.

11. The method of claim 9, wherein the photosensitizer is selected from the group consisting of photofrin$^{RTM}$, synthetic diporphyrins and dichlorins, phthalocyanines with or without metal substituents, chloroaluminum phthalocyan me with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorine $e_6$, mono-l-aspartyl derivative of chlorine $e_6$, di-l-aspartyl derivative of chlorine $e_6$, tin(IV) chlorine $e_6$, meta-tetrahydroxyphenylchlorin, benzoporphyrin derivatives, benzoporphyri n monoacid derivatives, tetracyanoethylene adducts of benzoporphyri n, dimethyl acetylenedicarboxylate adducts of benzoporphyrin, monoacid ring "a" derivative of benzoporphyrin, sulfonated aluminum PC, sulfonated AIPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, 5- aminolevulinic acid benzonaphthoporphyrazines, cationic imminium salts, tetracyclines, lutetium texaphyrin, tin-etio-purpurin, porphycenes, benzophenothiazinium and combinations thereof.

12. The method of claim 9, wherein the photosensitizer is benzoporphyrin derivative.

13. The method of claim 9, wherein the antibody is a tumoricidal antibody.

14. The method of claim 9, wherein light-activating comprises applying a suitable light source selected from the group consisting of a filtered conventional light source, a diode array, and a laser.

* * * * *

UNITED STATES PATENT AND TRADEMARK OFFICE
Certificate

Patent No. 7,498,029 B2                                                                Patented: March 3, 2009

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Tayyaba Hasan, Boston, MA (US).

Signed and Sealed this Twenty-fifth Day of November 2014.

<div style="text-align:right">

RAM R. SHUKLA
*Supervisory Patent Examiner*
Art Unit 1643
Technology Center 1600

</div>